US008173149B2

(12) United States Patent
Dalal et al.

(10) Patent No.: US 8,173,149 B2
(45) Date of Patent: May 8, 2012

(54) METHOD FOR PRODUCING POROUS β-TRICALCIUM PHOSPHATE GRANULES

(75) Inventors: Paresh S. Dalal, Shrewsbury, MA (US); Godofredo R. Diamaano, Edison, NJ (US); Shailesh C. Kulkarni, Natick, MA (US)

(73) Assignee: Stryker Corporation, Kalamazoo, MI (US)

( * ) Notice: Subject to any disclaimer, the term of this patent is extended or adjusted under 35 U.S.C. 154(b) by 1113 days.

(21) Appl. No.: 12/072,105

(22) Filed: Feb. 21, 2008

(65) Prior Publication Data
US 2009/0110743 A1 Apr. 30, 2009

Related U.S. Application Data

(60) Division of application No. 11/093,429, filed on Mar. 29, 2005, now Pat. No. 7,357,941, which is a division of application No. 09/960,789, filed on Sep. 21, 2001, now Pat. No. 6,949,251, which is a continuation-in-part of application No. 09/798,518, filed on Mar. 2, 2001, now abandoned.

(51) Int. Cl.
*A61F 2/00* (2006.01)
*C12N 11/14* (2006.01)
*C07K 17/14* (2006.01)
*A01N 37/18* (2006.01)
*A61K 31/7088* (2006.01)

(52) U.S. Cl. ............ 424/423; 424/426; 435/176; 514/2; 514/44; 530/811

(58) Field of Classification Search .................. None
See application file for complete search history.

(56) References Cited

U.S. PATENT DOCUMENTS

| | | |
|---|---|---|
| 3,899,556 A | 8/1975 | Heide et al. |
| 4,373,217 A | 2/1983 | Draenert |
| 4,563,432 A | 1/1986 | Ehlert et al. |
| 4,563,489 A | 1/1986 | Urist |
| 4,596,574 A | 6/1986 | Urist |
| 4,600,546 A | 7/1986 | Grundei |
| 4,610,692 A | 9/1986 | Eitenmuller et al. |
| 4,629,464 A | 12/1986 | Takata et al. |
| 4,636,526 A | 1/1987 | Dorman et al. |
| 4,645,503 A | 2/1987 | Lin et al. |
| 4,654,314 A | 3/1987 | Takagi et al. |
| 4,693,986 A | 9/1987 | Vit et al. |
| 4,713,076 A | 12/1987 | Draenert |
| 4,737,411 A | 4/1988 | Graves, Jr. et al. |
| 4,777,153 A | 10/1988 | Sonuparlak et al. |
| 4,781,721 A | 11/1988 | Grundei |
| 4,798,585 A | 1/1989 | Inoue et al. |
| 4,839,215 A | 6/1989 | Starling et al. |
| 4,842,603 A | 6/1989 | Draenert |
| 4,846,838 A | 7/1989 | Takai et al. |
| 4,861,733 A | 8/1989 | White |
| 4,869,906 A | 9/1989 | Dingeldein et al. |
| 4,878,914 A | 11/1989 | Miwa et al. |
| 4,911,720 A | 3/1990 | Collier |
| 4,963,145 A | 10/1990 | Takagi et al. |
| 4,965,039 A | 10/1990 | Schuetz |
| 5,011,495 A | 4/1991 | Hollinger |
| 5,017,518 A | 5/1991 | Hirayama et al. |
| 5,030,396 A | 7/1991 | Saita et al. |
| 5,034,352 A | 7/1991 | Vit et al. |
| 5,055,307 A | 10/1991 | Tsuru et al. |
| 5,059,388 A | 10/1991 | Kihara et al. |
| 5,064,436 A | 11/1991 | Ogiso et al. |
| 5,089,195 A | 2/1992 | Ichitsuka et al. |
| 5,106,626 A | 4/1992 | Parsons et al. |
| 5,135,394 A | 8/1992 | Hakamatsuka et al. |
| 5,152,791 A | 10/1992 | Hakamatsuka et al. |
| 5,171,720 A | 12/1992 | Kawakami |
| 5,207,710 A | 5/1993 | Chu et al. |
| 5,258,029 A | 11/1993 | Chu et al. |
| 5,263,985 A | 11/1993 | Bao et al. |
| 5,279,831 A | 1/1994 | Constantz et al. |
| 5,306,303 A | 4/1994 | Lynch |
| 5,318,779 A | 6/1994 | Hakamatsuka et al. |
| 5,338,356 A | 8/1994 | Hirano et al. |
| 5,338,772 A | 8/1994 | Bauer et al. |

(Continued)

FOREIGN PATENT DOCUMENTS

DE 2620890 11/1977

(Continued)

OTHER PUBLICATIONS

Andriano, K.P. et al., "Preliminary In Vivo Studies on the Osteogenic Potential of Bone Morphogenetic Proteins Delivered from an Absorbable Puttylike Polymer Matrix," *J. Biomed. Mater Re (Appl. Biomater.)* 53:36-43 (2000).

Benoit, M.-A. et al., "Antibiotic-Loaded Plaster of Paris Implants Coated With Poly Lactide-co-glycolide as a Controlled Release Delivery System for the Treatment of Bone Infections," *International Orthopaedics* 21(6):403-408 (1997).

Breitbart, A.S. et al., "Tricalcium Phosphate and Osteogenin: A Bioactive Onlay Bone Graft Substitute," *Plastic and Reconstructive Surgery* 96:699-708 (1995).

Bucholz, R.W. et al., "Hydroxyapatite and Tricalcium Phosphate Bone Graft Substitutes," *Orthopedic Clinics of North America* 18:323-334 (1987).

(Continued)

*Primary Examiner* — David Naff
(74) *Attorney, Agent, or Firm* — McCraken & Frank LLC

(57) ABSTRACT

A porous β-tricalcium phosphate material for bone implantation is provided. The multiple pores in the porous TCP body are separate discrete voids and are not interconnected. The pore size diameter is in the range of 20-500 μm, preferably 50-125 μm. The porous β-TCP material provides a carrier matrix for bioactive agents and can form a moldable putty composition upon the addition of a binder. Preferably, the bioactive agent is encapsulated in a biodegradable agent. The invention provides a kit and an implant device comprising the porous β-TCP, and a bioactive agent and a binder. The invention also provides an implantable prosthetic device comprising a prosthetic implant having a surface region, a porous β-TCP material disposed on the surface region and optionally comprising at least a bioactive agent or a binder. Methods of producing the porous β-TCP material and inducing bone formation are also provided.

15 Claims, 28 Drawing Sheets

U.S. PATENT DOCUMENTS

| | | | |
|---|---|---|---|
| 5,385,887 | A | 1/1995 | Yim et al. |
| 5,422,340 | A | 6/1995 | Ammann et al. |
| 5,464,440 | A | 11/1995 | Johansson |
| 5,492,697 | A | 2/1996 | Boyan et al. |
| 5,520,923 | A | 5/1996 | Tjia et al. |
| RE35,267 | E | 6/1996 | Tsuru et al. |
| 5,522,894 | A | 6/1996 | Draenert |
| 5,531,794 | A | 7/1996 | Takagi et al. |
| 5,571,185 | A | 11/1996 | Schug |
| 5,574,075 | A | 11/1996 | Draenert |
| 5,597,897 | A | 1/1997 | Ron et al. |
| 5,626,861 | A | 5/1997 | Laurencin et al. |
| 5,641,502 | A | 6/1997 | Skalla et al. |
| 5,650,108 | A | 7/1997 | Nies et al. |
| 5,707,962 | A | 1/1998 | Chen et al. |
| 5,717,006 | A | 2/1998 | Daculsi et al. |
| 5,741,329 | A | 4/1998 | Agrawal et al. |
| 5,776,193 | A | 7/1998 | Kwan et al. |
| 5,851,670 | A | 12/1998 | Mitoh et al. |
| 5,866,155 | A | 2/1999 | Laurencin et al. |
| 5,897,953 | A | 4/1999 | Ogawa et al. |
| 5,914,121 | A | 6/1999 | Robey et al. |
| 5,922,025 | A | 7/1999 | Hubbard |
| 5,939,388 | A | 8/1999 | Rosen et al. |
| 5,962,427 | A | 10/1999 | Goldstein et al. |
| 6,010,648 | A | 1/2000 | Yamamoto et al. |
| 6,018,095 | A | 1/2000 | Lerch et al. |
| 6,027,744 | A | 2/2000 | Vacanti et al. |
| 6,030,635 | A | 2/2000 | Gertzman et al. |
| 6,048,964 | A | 4/2000 | Lee et al. |
| 6,051,247 | A | 4/2000 | Hench et al. |
| 6,063,117 | A | 5/2000 | Perry |
| 6,077,989 | A | 6/2000 | Kandel et al. |
| 6,080,801 | A | 6/2000 | Draenert et al. |
| 6,110,503 | A | 8/2000 | Rickey et al. |
| 6,118,043 | A | 9/2000 | Nies et al. |
| 6,136,029 | A | 10/2000 | Johnson et al. |
| 6,165,486 | A | 12/2000 | Marra et al. |
| 6,180,605 | B1 | 1/2001 | Chen et al. |
| 6,180,606 | B1 | 1/2001 | Chen et al. |
| 6,187,046 | B1 | 2/2001 | Yamamoto et al. |
| 6,187,047 | B1 | 2/2001 | Kwan et al. |
| 6,194,006 | B1 | 2/2001 | Lyons et al. |
| 6,201,065 | B1 | 3/2001 | Pathak et al. |
| 6,203,574 | B1 | 3/2001 | Kawamura |
| 6,210,612 | B1 | 4/2001 | Pickrell et al. |
| 6,235,225 | B1 | 5/2001 | Okada et al. |
| 6,235,665 | B1 | 5/2001 | Pickrell et al. |
| 6,261,322 | B1 | 7/2001 | Despres, III et al. |
| 6,280,478 | B1 | 8/2001 | Richter et al. |
| 6,281,257 | B1 | 8/2001 | Ma et al. |
| 6,296,667 | B1 | 10/2001 | Johnson et al. |
| 6,303,297 | B1 | 10/2001 | Lincoln et al. |
| 6,316,091 | B1 | 11/2001 | Richart et al. |
| 6,340,648 | B1 | 1/2002 | Imura et al. |
| 6,346,123 | B1 | 2/2002 | McKay |
| 6,350,462 | B1 | 2/2002 | Hakamatsuka et al. |
| 6,358,532 | B2 | 3/2002 | Starling et al. |
| 6,376,573 | B1 | 4/2002 | White et al. |
| 6,432,437 | B1 | 8/2002 | Hubbard |
| 6,432,919 | B1 | 8/2002 | Wang et al. |
| 6,451,059 | B1 | 9/2002 | Janas et al. |
| 6,479,418 | B2 | 11/2002 | Li et al. |
| 6,511,510 | B1 | 1/2003 | de Bruijn et al. |
| 6,521,246 | B2 | 2/2003 | Sapieszko et al. |
| 6,524,345 | B1 | 2/2003 | Valimaa et al. |
| 6,527,810 | B2 | 3/2003 | Johnson et al. |
| 6,540,784 | B2 | 4/2003 | Barlow et al. |
| 6,592,787 | B2 | 7/2003 | Pickrell et al. |
| 6,599,515 | B1 | 7/2003 | Delmotte |
| 6,667,049 | B2 | 12/2003 | Janas et al. |
| 6,692,761 | B2 | 2/2004 | Mahmood et al. |
| 6,790,233 | B2 | 9/2004 | Brodke et al. |
| 7,037,304 | B2 | 5/2006 | Lyles et al. |
| 7,045,125 | B2 | 5/2006 | Erbe et al. |
| 7,122,057 | B2 | 10/2006 | Beam et al. |
| 7,172,629 | B2 | 2/2007 | McKay |
| 2001/0014667 | A1 | 8/2001 | Chen et al. |
| 2002/0022885 | A1 | 2/2002 | Ochi |
| 2002/0035402 | A1 | 3/2002 | De Bruijn et al. |
| 2002/0082694 | A1 | 6/2002 | McKay |
| 2002/0114795 | A1 | 8/2002 | Thorne et al. |
| 2002/0115742 | A1 | 8/2002 | Trieu et al. |
| 2002/0151466 | A1 | 10/2002 | Hubbard et al. |
| 2002/0193883 | A1 | 12/2002 | Wironen |
| 2003/0009235 | A1 | 1/2003 | Manrique et al. |
| 2003/0031698 | A1 | 2/2003 | Roeder et al. |
| 2003/0069638 | A1 | 4/2003 | Barlow et al. |
| 2003/0152606 | A1 | 8/2003 | Gerber |

FOREIGN PATENT DOCUMENTS

| | | |
|---|---|---|
| DE | 4216496 | 11/1993 |
| DE | 29922585 | 7/2000 |
| DE | 100 63 119 | 8/2001 |
| DE | 10063119 | 8/2001 |
| EP | 0 267 624 | 5/1988 |
| EP | 0 360 244 | 3/1990 |
| EP | 0 987 032 | 3/2000 |
| EP | 1 027 897 | 8/2000 |
| EP | 1 142 597 | 10/2001 |
| GB | 2078696 | 1/1982 |
| GB | 2 323 083 | 9/1998 |
| GB | 2 348 872 | 10/2000 |
| GB | 2354518 | 3/2001 |
| JP | 59101145 | 6/1984 |
| JP | 59131346 | 7/1984 |
| JP | 59171546 | 9/1984 |
| JP | 60142857 | 7/1985 |
| JP | 6141466 | 2/1986 |
| JP | 6145748 | 3/1986 |
| JP | 6168054 | 4/1986 |
| JP | 61127658 | 6/1986 |
| JP | 930526504 | 8/1986 |
| JP | 63046167 | 2/1988 |
| JP | 6430572 | 2/1989 |
| JP | 1108143 | 4/1989 |
| JP | 1126977 | 5/1989 |
| JP | 1230412 | 9/1989 |
| JP | 3191963 | 8/1991 |
| JP | 364482 | 10/1991 |
| JP | 429630 | 5/1992 |
| JP | 5042168 | 2/1993 |
| JP | 5208877 | 8/1993 |
| JP | 566909 | 9/1993 |
| JP | 5237178 | 9/1993 |
| JP | 5305134 | 11/1993 |
| JP | 588687 | 12/1993 |
| JP | 655219 | 7/1994 |
| JP | 6296676 | 10/1994 |
| JP | 6102582 | 12/1994 |
| JP | 7023994 | 1/1995 |
| JP | 7291759 | 11/1995 |
| JP | 9030988 | 2/1997 |
| JP | 11276468 | 10/1999 |
| JP | 2000 262608 | 9/2000 |
| JP | 2001-058885 | 3/2001 |
| JP | 3231135 | 9/2001 |
| WO | WO 86/01113 | 2/1986 |
| WO | WO 87/04110 | 7/1987 |
| WO | WO 87/07495 | 12/1987 |
| WO | WO 93/07835 | 4/1993 |
| WO | WO 93/15721 | 8/1993 |
| WO | WO 93/20859 | 10/1993 |
| WO | WO 94/15652 | 7/1994 |
| WO | WO 94/15653 | 7/1994 |
| WO | WO 95/21634 | 8/1995 |
| WO | WO 97/31661 | 9/1997 |
| WO | WO 97/45147 | 12/1997 |
| WO | WO 97/46178 | 12/1997 |
| WO | WO 98/38949 | 9/1998 |
| WO | WO 98/47485 | 10/1998 |
| WO | WO 99/16478 | 4/1999 |
| WO | WO 99/16479 | 4/1999 |
| WO | WO 99/20319 | 4/1999 |
| WO | WO 99/37246 | 7/1999 |
| WO | WO 00/18443 | 4/2000 |
| WO | WO 00/35511 | 6/2000 |

| WO | WO 00/45870 | 8/2000 |
| WO | WO 00/45871 | 8/2000 |
| WO | WO 00/50104 | 8/2000 |
| WO | WO 01/03709 | 1/2001 |
| WO | WO 01/13970 | 3/2001 |
| WO | WO 01/28603 | 4/2001 |
| WO | WO 01/29189 | 4/2001 |
| WO | WO 01/44141 | 6/2001 |
| WO | WO 01/54746 | 8/2001 |
| WO | WO 01/66163 | 9/2001 |
| WO | WO 02/11781 | 2/2002 |
| WO | WO 02/15881 | 2/2002 |

OTHER PUBLICATIONS

Chow, L.C., "Solubility of Calcium Phosphates," *Monogr Oral Sci. Basel, Karger* 18:94-111 (2001).

Eggli, P.S. et al., "Porous Hydroxyapatite and Tricalcium Phosphate Cylinders with Two Different Pore Size Ranges Implanted in the Cancellous Bone of Rabbits," *Clinical Orthopaedics and Related Research* 232:127-138 (1988).

Frayssinet, P. et al., "High Compressive Strength Macroporous Calcium Phosphate Ceramics for Bone Repair," http://www.utc.fr/esb/esb98/abs_htm/722.html, 1998.

Gerhart, T.N. et al., "In vitro Characterization and Biomechanical Optimization of a Biodegradable Particulate Composite Bone Cement," *Journal of Biomedical Materials Research* 22:1071-1082 (1988).

Gombotz, W.R. et al., "Stimulation of Bone Healing by Transforming Growth Factor-Beta$_1$ Released from Polymeric or Ceramic Implants," *Journal of Applied Biomaterials* 5(2):141-150 (1994).

Hua, W. et al., "New Bone Formation in the in vivo Implantation of Bioceramics," *Chinese Medical Journal* 105:753-757 (1992).

Hutmacher, D.W., "Scaffolds in Tissue Engineering Bone and Cartilage," *Biomaterials* 21: 2529-2543 (2000).

Laffargue, PH. et al., "Evaluation of Human Recombinant Bone Morphogenetic Protein-2-Loaded Tricalcium Phosphate Implants in Rabbits' Bone Defects," *Bone* 25:55S-58S (1999).

Lange, T.A. et al., "Granular Tricalcium Phosphate in Large Cancellous Defects," *Annals of Clinical and Laboratory Science* 16:467-472 (1986).

Metsger, D.S. et al., "Histomorphometric Analysis of Tricalcium Phosphate Ceramic Implanted Into Turkeys," *Bone* 14:243-248 (1993).

Nade, S. et al., "Osteogenesis After Bone and Bone Marrow Transplantation," *Clinical Orthopaedics and Related Research* 181:255-263 (1983).

Nery, E.B. et al., "Tissue Response to Biphasic Calcium Phosphate Ceramic With Different Ratios of HA/βTCP in Periodontal Osseous Defects," *Journal of Periodontology* 63:729-735 (1992).

Ohgushi, H. et al., "Marrow Cell Induced Osteogenesis in Porous Hydroxyapatite and Tricalcium Phosphate: A Comparative Histomorphometric Study of Ectopic Bone Formation," *Journal of Biomedical Materials Research* 24:1563-1570 (1990).

Ohura, K. et al., "Healing of Segmental Bone Defects in Rats Induced by a β-TCP-MCPM Cement Combined with rhBMP-2," *Journal of Biomedical Materials.Research* 44:168-175 (1999).

Soriano, I. et al., "Formulation of Calcium Phosphates/Poly (d,l-lactide) Blends Containing Gentamicin for Bone Implantation," *Journal of Controlled Release* 68:121-134 (2000).

Tancred, D.C. et al., "A Synthetic Bone Implant Macroscopically Identical to Cancellous Bone," *Biomaterials* 19:2303-2311 (1998).

Thoma, K. et al., "Biodegradable Controlled Release Implants Based on β-Tricalcium Phosphate Ceramic," *European Journal Pharmaceutics and Biopharmaceutics* 38:107-112 (1992).

Uchida, A. et al., "Bone Ingrowth into Three Different Porous Ceramics Implanted into the Tibia of Rats and Rabbits," *Journal of Orthopaedic Research* 3:65-77 (1985).

Uchida, A. et al., "The use of Ceramics for Bone Replacement," *The Journal of Bone and Joint Surgery* 66-B:269-275 (1984).

Vaccaro, A.R., "The Role of the Osteoconductive Scaffold in Synthetic Bone Graft," *Orthopedics* 25(5):571-578 (2002).

White, E. et al., "Biomaterial Aspects of Interpore-200 Porous Hydroxyapatite," *Dental Clinics of North America* 30(1):49-67 (1986).

Zheng, Q. et al., "Artificial Bone of Porous Tricalcium Phosphate Ceramics and its Preliminary Clinical Application," *Journal of Tongii Medical University* 12:173-178 (1992).

METHOD FOR PRODUCING POROUS β-TRICALCIUM PHOSPHATE GRANULES

This application is a divisional of U.S. application Ser. No. 11/093,429, filed Mar. 29, 2005, now U.S. Pat. No. 7,357,941, which is a divisional of U.S. application Ser. No. 09/960,789, filed Sep. 21, 2001, now U.S. Pat. No. 6,949,251, which is a continuation-in-part of U.S. application Ser. No. 09/798,518, filed Mar. 2, 2001, now abandoned, the entire disclosures of each of which are incorporated by reference herein.

BACKGROUND OF THE INVENTION

Bone tissue in the human body comprises the largest proportion of the body's connective tissue mass. However, unlike other connective tissues, its matrix consists of physiologically mineralized, tiny crystallites of a basic, carbonate-containing calcium phosphate called hydroxyapatite distributed in an organized collagen structure. Repair of this tissue is a complex process involving a number of cellular functions directed towards the formation of a scaffold and mineralization of the defect followed by an eventual remodeling of the defect site to attain the original structure.

Implantations of calcium phosphate based biomaterials have been found to be generally compatible and conducive to bone repair. Bone repair is influenced by a number of physico-chemical variables associated with calcium phosphate such as the calcium to phosphate molar ratio. Hydroxyapatite and tricalcium phosphate are widely used in bone implants. Hydroxyapatite has the chemical formula $Ca_{10}(PO_4)_6(OH)_2$, and the ratio of calcium to phosphate is about 1.67. Tricalcium phosphate (TCP) has the formula of $Ca_3(PO_4)_2$, and the ratio of calcium to phosphate is about 1.5. Tricalcium phosphate has biological properties of being non-reactive and resorbable. It acts as a scaffolding for bone ingrowth and undergoes progressive degradation and replacement by bone (Lange et al., *Annals of Clinical and Laboratory Science*, 16, pp. 467-472 (1986)). TCP is degraded 10-20 times faster than hydroxyapatite. A TCP implant generally results in superior remodeling than hydroxyapatite during the final stage of bone formation. It is noteworthy that TCP is resorbed by osteoclast cells, whereas, the much slower resorption of hydroxyapatite is effected mainly by foreign-body giant cells. The giant cells have a limit as to the amount of hydroxyapatite they will resorb.

Porous ceramic material is often selected as the matrix for bone implants. When such material is embedded at the implant site, the porous material is resorbed by osteolytic cells which infiltrate the pores. Simultaneously, the bone tissue is regenerated by osteoblasts. A certain pore size is required for osteoblasts to invade the pore of the implant material. Parameters such as crystallinity, solubility, particle size, porosity, pore structure and pore size of the implanted material can greatly influence bone compatibility and bone integration. An inappropriate combination of the above parameters can lead to improper bone repair.

The use of porous ceramics having interconnected pores as an implantable solid material for bone substitutes has been described (see, e.g., U.S. Pat. No. 5,171,720; see also Frayssinet et al., *Biomaterials*, 14, pp. 423-429 (1993)). Such porous ceramics, however, are brittle and are not capable of being easily shaped by the practitioner during an operation.

Excessively large pore size and high porosity of the ceramic material can lead to excessive resorption rates, thus, preventing the matrix from providing a scaffold for the newly synthesized bone. When the rate of resorption is faster than the rate of bone growth, it often leads to an inflammatory response. Small pore size and low porosity of the ceramic material will lead to low resorption rates causing encapsulation of matrix particles in the new bone.

It would thus be desirable to identify a biomaterial which can be applied to a defect site and which can greatly enhance the regenerative process, particularly when used with other bioactive agents such as bone morphogenic proteins and other related factors. In addition, it would be desirable to identify and use a matrix which acts as a mechanically durable carrier for the bioactive agents and is a well-tolerated bone replacement material that favors healing.

SUMMARY OF THE INVENTION

The present invention solves these problems by identifying a porous ceramic material having a composition, pore size, porosity and granule size for improving the regeneration of bone tissue in a living body, and repairing a bone defect in a human or animal. The present invention provides a porous β-tricalcium phosphate (β-TCP) material for use in bone implant applications. The invention provides porous forms of β-TCP granules which are biocompatible and support the development of new bone throughout its structural form.

The invention also provides a composition comprising the porous β-TCP with a bioactive agent such as an antibiotic, a bone morphogenic protein (BMP), or a nucleic acid molecule comprising a sequence encoding BMP in the presence or absence of a morphogenic protein stimulatory factor (MPSF) to improve osteoconductivity. In a preferred embodiment, the bioactive agent is encapsulated in a biodegradable agent. Preferably, the particle size of the biodegradable agent is 20-500 μm. The porous β-TCP material or porous β-TCP/bioactive agent mixture can also be used in conjunction with binders to form a moldable putty composition ready for shaping in the implant site. The invention also provides a kit comprising the porous β-TCP, and at least one or more additional components including a bioactive agent and a binder.

In another aspect, the invention also provides an implantable device comprising the porous β-TCP material, and optionally comprising one or more additional components including a bioactive agent such as a BMP, an antibiotic or a binder. The invention also provides an implantable prosthetic device comprising the porous β-TCP material and optionally comprising one or more additional components including a bioactive agent such as a BMP, an antibiotic or a binder. The prosthetic device or implantable device comprising the porous β-TCP and BMP may optionally comprise a MPSF.

Another object of the invention is to provide a method of producing the porous β-TCP material. The method comprises blending the TCP powder with a pore-forming agent, adding a granulating solution to form a crumbly mass, passing the crumbly mass through a sieve to form granules and sintering the granules to form the porous β-TCP.

The invention also provides a method of inducing bone formation in a mammal comprising the step of implanting in the defect site of a mammal a composition comprising the porous β-TCP and optionally a binder and/or a bioactive agent. The invention describes a method of delivering a bioactive agent at a site requiring bone formation comprising implanting at the defect site of a mammal a composition comprising the porous β-TCP and a bioactive agent, wherein the bioactive agent is optionally encapsulated in a biodegradable agent. The invention also describes a method of delivering a bioactive agent to a site requiring cartilage formation comprising implanting at the defect site of a mammal a composition comprising the bioactive agent and biodegradable agent, wherein the bioactive agent is encapsulated in the biodegradable agent.

DETAILED DESCRIPTION OF THE INVENTION

Figure 1:
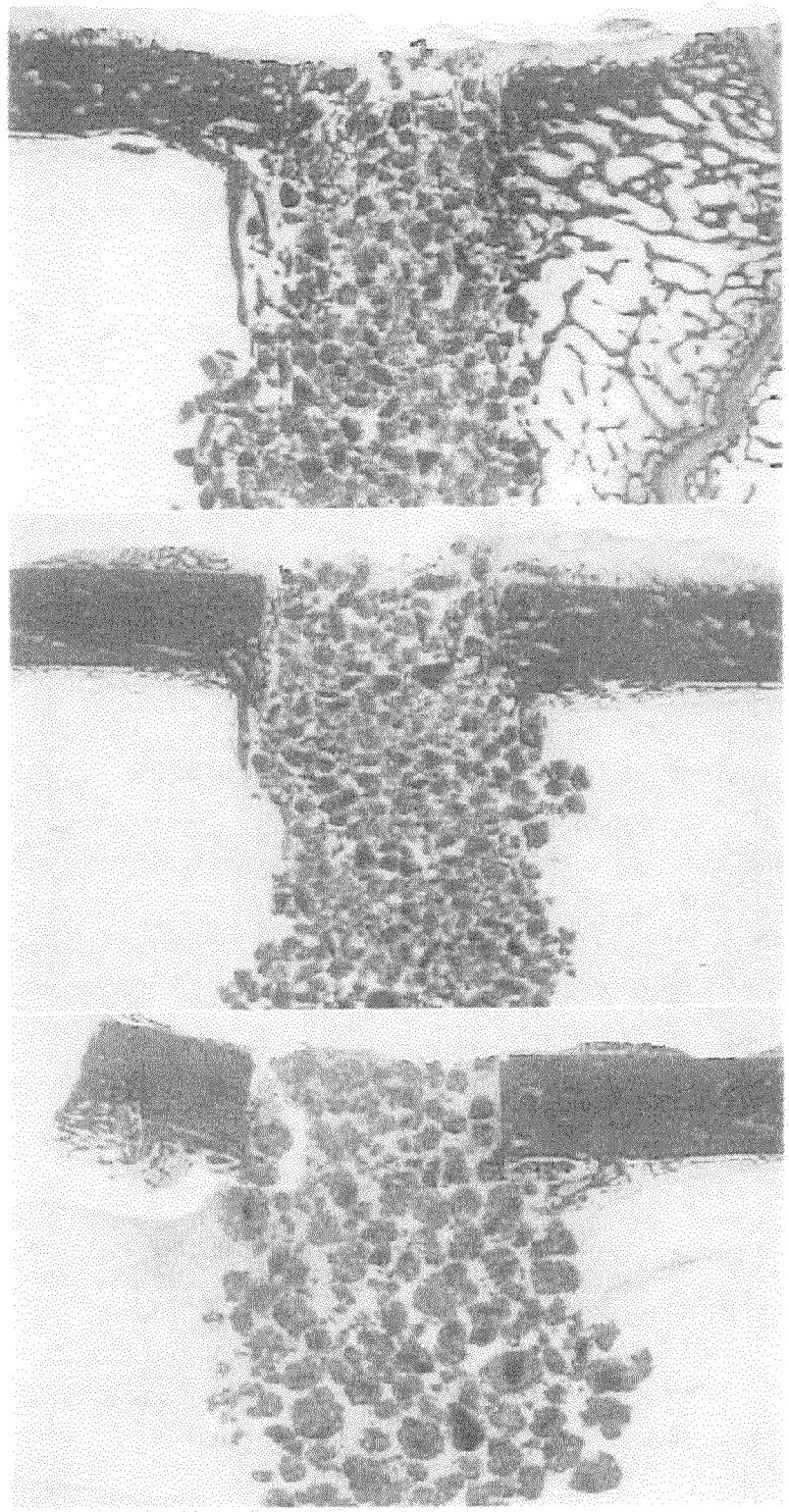
FIG. 1. Histologic image of animal number 297L (left tibia) at 4 weeks with placebo. From top to bottom, the sites are proximal, middle and distal, each containing β-TCP putty 89B, β-TCP putty 89C, β-TCP putty 89F, respectively.

In order that the invention herein described may be fully understood, the following detailed description is set forth.

"Amino acid sequence homology" is understood to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Certain particularly preferred morphogenic polypeptides share at least 60%, and preferably 70% amino acid sequence identity with the C-terminal 102-106 amino acids, defining the conserved seven-cysteine domain of human OP-1, BMP-2, and related proteins.

Amino acid sequence homology can be determined by methods well known in the art. For instance, to determine the percent homology of a candidate amino acid sequence to the sequence of the seven-cysteine domain, the two sequences are first aligned. The alignment can be made with, e.g., the dynamic programming algorithm described in Needleman et al., *J. Mol. Biol.*, 48, pp. 443 (1970), and the Align Program, a commercial software package produced by DNAstar, Inc. The teachings by both sources are incorporated by reference herein. An initial alignment can be refined by comparison to a multi-sequence alignment of a family of related proteins. Once the alignment is made and refined, a percent homology score is calculated. The aligned amino acid residues of the two sequences are compared sequentially for their similarity to each other. Similarity factors include similar size, shape and electrical charge. One particularly preferred method of determining amino acid similarities is the PAM250 matrix described in Dayhoff et al., *Atlas of Protein Sequence and Structure*, 5, pp. 345-352 (1978 & Supp.), which is incorporated herein by reference. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate sequence and the seven-cysteine domain. The geometric mean is the square root of the product of these scores. The normalized raw score is the percent homology.

"Biocompatible" refers to a material that does not elicit detrimental effects associated with the body's various protective systems, such as cell and humoral-associated immune responses, e.g., inflammatory responses and foreign body fibrotic responses. The term biocompatible also implies that no specific undesirable cytotoxic or systemic effects are caused by the material when it is implanted into the patient.

"Binder" refers to any biocompatible material which, when admixed with osteogenic protein and/or the porous matrix promotes bone formation. Certain preferred binders promote such repair using less osteogenic protein than standard osteogenic devices. Other preferred binders can promote repair using the same amount of the osteogenic protein as the standard osteogenic devices while some require more to promote repair. As taught herein, the skilled artisan can determine an effective amount of protein for use with any suitable binder using only routine experimentation. Among the other characteristics of a preferred binder is an ability to render the device: pliable, shapeable and/or malleable; injectable; adherent to bone, cartilage, muscle and other tissues, resistant to disintegration upon washing and/or irrigating during surgery; and, resistant to dislodging during surgery, suturing and post-operatively, to name but a few. Additionally, in certain preferred embodiments, a binder can achieve the aforementioned features and benefits when present in low proportions.

"Biodegradable agent" refers to a resorbable biocompatible material such as a material that degrades gradually at the implant site. The material is capable of encapsulating a bioactive agent to provide time release or sustained release delivery of the bioactive agent. The biodegradable material encompasses natural and synthetic polymers. Examples of biodegradable material are poly(L-lactide) (PLLA), poly(D,L-lactide) (PDLLA), polyglycolide (PGA), poly(lactide-co-glycolide) (PLGA) and co-polymers thereof.

"Bone" refers to a calcified (mineralized) connective tissue primarily comprising a composite of deposited calcium and phosphate in the form of hydroxyapatite, collagen (primarily Type I collagen) and bone cells such as osteoblasts, osteocytes and osteoclasts, as well as to bone marrow tissue which forms in the interior of true endochondral bone. Bone tissue differs significantly from other tissues, including cartilage tissue. Specifically, bone tissue is vascularized tissue composed of cells and a biphasic medium comprising a mineralized, inorganic component (primarily hydroxyapatite crystals) and an organic component (primarily of Type I collagen). Glycosaminoglycans constitute less than 2% of this organic component and less than 1% of the biphasic medium itself, or of bone tissue per se. Moreover, relative to cartilage tissue, the collagen present in bone tissue exists in a highly-organized parallel arrangement. Bony defects, whether from degenerative, traumatic or cancerous etiologies, pose a formidable challenge to the reconstructive surgeon. Particularly difficult is reconstruction or repair of skeletal parts that comprise part of a multi-tissue complex, such as occurs in mammalian joints.

"Bone formation" means formation of endochondral bone or formation of intramembranous bone. In humans, bone formation begins during the first 6-8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts, which now are present at the site. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage, which is subsequently replaced with newly formed bone.

"Bone morphogenic protein (BMP)" refers to a protein belonging to the BMP family of the TGF-β superfamily of proteins (BMP family) based on DNA and amino acid sequence homology. A protein belongs to the BMP family according to this invention when it has at least 50% amino acid sequence identity with at least one known BMP family member within the conserved C-terminal cysteine-rich domain which characterizes the BMP protein family. Members of the BMP family may have less than 50% DNA or amino acid sequence identity overall.

"Conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., supra. Examples of conservative substitutions are substitutions within the following groups: (a)

valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituting amino acid residue in place of an amino acid residue in a given parent amino acid sequence, where antibodies specific for the parent sequence are also specific for, i.e., "cross-react" or "immuno-react", with, the resulting substituted polypeptide sequence.

"Defect" or "defect site" refers to a site requiring bone, joint, cartilage or ligament repair, construction, fusion, regeneration or augmentation. The site may be an orthopedic structural disruption or abnormality, or a site where bone does not normally grow. The defect further can define an osteochondral defect, including a structural disruption of both the bone and overlying cartilage. A defect can assume the configuration of a "void", which is understood to mean a three-dimensional defect such as, for example, a gap, cavity, hole or other substantial disruption in the structural integrity of a bone or joint. A defect can be the result of accident, disease, surgical manipulation, and/or prosthetic failure. In certain embodiments, the defect is a void having a volume incapable of endogenous or spontaneous repair. Such defects in long bone are generally twice the diameter of the subject bone and are also called "critical size" defects. For example, in a canine ulna defect model, the art recognizes such defects to be approximately 3-4 cm. Generally, critical size defects are approximately 1.0 cm, and incapable of spontaneous repair. See, for example, Schmitz et al., *Clinical Orthopaedics and Related Research,* 205, pp. 299-308 (1986); and Vukicevic et al., in *Advances in Molecular and Cell Biology,* 6, pp. 207-224 (1993) (JAI Press, Inc.). In rabbit and monkey segmental defect models, the gap is approximately 1.5 cm and 2.0 cm, respectively. In other embodiments, the defect is a non-critical size segmental defect. Generally, these are capable of spontaneous repair. In certain other embodiments, the defect is an osteochondral defect, such as an osteochondral plug. Such a defect traverses the entirety of the overlying cartilage and enters, at least in part, the underlying bony structure. In contrast, a chondral or subchondral defect traverses the overlying cartilage, in part or in whole, respectively, but does not involve the underlying bone. Other defects susceptible to repair using the instant invention include, but are not limited to, non-union fractures; bone cavities; tumor resection; fresh fractures (distracted or undistracted); cranial, maxillofacial and facial abnormalities, for example, in facial skeletal reconstruction, specifically, orbital floor reconstruction, augmentation of the alveolar ridge or sinus, periodontal defects and tooth extraction socket; cranioplasty, genioplasty, chin augmentation, palate reconstruction, and other large bony reconstructions; vertebroplasty, interbody fusions in the cervical, thoracic and lumbar spine and posteriolateral fusions in the thoracic and lumbar spine; in osteomyelitis for bone regeneration; appendicular fusion, ankle fusion, total hip, knee and joint fusions or arthroplasty; correcting tendon and/or ligamentous tissue defects such as, for example, the anterior, posterior, lateral and medial ligaments of the knee, the patella and achilles tendons, and the like as well as those defects resulting from diseases such as cancer, arthritis, including osteoarthritis, and other bone degenerative disorders such as osteochondritis dessicans.

"Granulating solution" refers to a solution that has a certain degree of consistency and cohesiveness, and enhances the formation of granules.

"Morphogenic protein" refers to a protein having morphogenic activity (see below). Preferably a morphogenic protein of this invention comprises at least one polypeptide belonging to the BMP protein family. Morphogenic proteins may be capable of inducing progenitor cells to proliferate and/or to initiate differentiation pathways that lead to cartilage, bone, tendon, ligament, neural or other types of tissue formation depending on local environmental cues, and thus morphogenic proteins may behave differently in different surroundings. For example, an osteogenic protein may induce bone tissue at one treatment site and neural tissue at a different treatment site.

"Morphogenic protein stimulatory factor (MPSF)" refers to a factor that is capable of stimulating the ability of a morphogenic protein to induce tissue formation from a progenitor cell. The MPSF may have a direct or indirect effect on enhancing morphogenic protein inducing activity. For example, the MPSF may increase the bioactivity of another MPSF. Agents that increase MPSF bioactivity include, for example, those that increase the synthesis, half-life, reactivity with other biomolecules such as binding proteins and receptors, or the bioavailability of the MPSF.

"Osteogenic protein (OP)" refers to a morphogenic protein that is capable of inducing a progenitor cell to form cartilage and/or bone. The bone may be intramembranous bone or endochondral bone. Most osteogenic proteins are members of the BMP protein family and are thus also BMPs. As described elsewhere herein, the class of proteins is typified by human osteogenic protein (hOP-1). Other osteogenic proteins useful in the practice of the invention include osteogenically active forms of OP-1, OP-2, OP-3, BMP-2, BMP-3, BMP-4, BMP-5, BMP-6, BMP-9, DPP, Vg1, Vgr, 60A protein, GDF-1, GDF-3, GDF-5, GDF-6, GDF-7, BMP-10, BMP-11, BMP-13, BMP-15, UNIVIN, NODAL, SCREW, ADMP or NEURAL and amino acid sequence variants thereof. In one currently preferred embodiment, osteogenic protein includes any one of: OP-1, OP-2, OP-3, BMP-2, BMP-4, BMP-5, BMP-6, BMP-9, and amino acid sequence variants and homologs thereof, including species homologs thereof. Particularly preferred osteogenic proteins are those comprising an amino acid sequence having at least 70% homology with the C-terminal 102-106 amino acids, defining the conserved seven cysteine domain, of human OP-1, BMP-2, and related proteins. Certain preferred embodiments of the instant invention comprise the osteogenic protein, OP-1. As further described elsewhere herein, the osteogenic proteins suitable for use with applicants' invention can be identified by means of routine experimentation using the art-recognized bioassay described by Reddi and Sampath (Sampath et al., *Proc. Natl. Acad. Sci.,* 84, pp. 7109-13, incorporated herein by reference)

Proteins useful in this invention include eukaryotic proteins identified as osteogenic proteins (see U.S. Pat. No. 5,011,691, incorporated herein by reference), such as the OP-1, OP-2, OP-3 and CBMP-2 proteins, as well as amino acid sequence-related proteins, such as DPP (from *Drosophila*), Vg1 (from *Xenopus*), Vgr-1 (from mouse), GDF-1 (from humans, see Lee, *PNAS,* 88, pp. 4250-4254 (1991)), 60A (from *Drosophila*, see Wharton et al. *PNAS,* 88, pp. 9214-9218 (1991)), dorsalin-1 (from chick, see Basler et al. *Cell* 73, pp. 687-702 (1993) and GenBank accession number L12032) and GDF-5 (from mouse, see Storm et al. *Nature,* 368, pp. 639-643 (1994)). The teachings of the above references are incorporated herein by reference. BMP-3 is also preferred. Additional useful proteins include biosynthetic morphogenic constructs disclosed in U.S. Pat. No. 5,011,691, incorporated herein by reference, e.g., COP-1, COP-3, COP-4, COP-5, COP-7 and COP-16, as well as other proteins known in the art. Still other proteins include osteogenically active forms of BMP-3b (see Takao, et al. *Biochem. Biophys.*

*Res. Comm.,* 219, pp. 656-662 (1996)). BMP-9 (see WO95/33830), BMP-15 (see WO96/35710), BMP-12 (see WO95/16035), CDMP-1 (see WO94/12814), CDMP-2 (see WO94/12814), BMP-10 (see WO94/26893), GDF-1 (see WO92/00382), GDF-10 (see WO95/10539), GDF-3 (see WO94/15965) and GDF-7 (see WO95/01802). The teachings of the above references are incorporated herein by reference.

"Repair" is intended to mean new bone and/or cartilage formation which is sufficient to at least partially fill the void or structural discontinuity at the defect. Repair does not, however, mean, or otherwise necessitate, a process of complete healing or a treatment which is 100% effective at restoring a defect to its pre-defect physiological/structural/mechanical state.

"Synergistic interaction" refers to an interaction in which the combined effect of two or more agents is greater than the algebraic sum of their individual effects.

Porous β-TCP

This present invention provides a porous β-TCP having a pore size and granule size appropriate for bone formation, bone regeneration, and bone repair at a defect site in a human or animal. The porous β-TCP body described in this invention comprises β-TCP having a multiplicity of pores. Each pore is a single separate void partitioned by walls and is not interconnected. The porous β-TCP body of this invention is distinct from the cancellous or fenestrate structures that contain capillary void paths or interconnections between adjacent pores. The pore diameter size of the porous β-TCP of this invention is in the range of 20-500 μm. In one embodiment, the pore diameter size is in the range of 410-460 μm. In a preferred embodiment, the pore diameter size is 40-190 μm. In another embodiment, the pore diameter size is in the range of 20-95 um. In a more preferred embodiment, the pore diameter is in the range of 50-125 μm. These pores provide residence spaces for the infiltrating osteolytic cells and osteoblasts when the β-TCP material is embedded in the living body. In one embodiment, the pores are spherical and uniformly distributed. Spherical pores having a diameter in the range of 20-500 μm are appropriate for osteoblast infiltration. Spherical pores also provide the porous body with the necessary mechanical strength during the period that new bone is being synthesized, thus preventing the bone from fracturing during this period.

Tricalcium phosphate (TCP) has the formula of $Ca_3(PO_4)_2$, with the Ca/P ratio being about 1.5. TCP powder has an apatite crystal structure. Upon sintering, the apatite structure converts to the rhombic β-TCP structure. At high temperatures, the metastable, α-TCP structure can also form. α-TCP is known to have excessive solubility, which does not permit the rate of resorption to be complementary to the rate of substitution by the hard tissue. In addition, α-TCP is capable of generating harmful inflammatory responses. In a preferred embodiment, the TCP is sintered at high temperatures of 1100-1120° C. Above 1300° C., TCP is converted to the metastable α-TCP. Sintering the TCP reduces its solubility in body fluids, which leads to a corresponding reduction in its chemical activity so that the porous TCP is well tolerated in the body and acute inflammatory reactions are avoided. Therefore, the porous β-TCP is preferably sintered. More preferably the β-TCP comprises β-TCP that is 95-100% pure.

The porous β-TCP material of the present invention may have any shape and size. In one embodiment, the porous β-TCP is granular and has a particle size between 0.1 to 2 mm. In a preferred embodiment, the particle size is 0.5-1.7 mm. In a more preferred embodiment the particle size is 1.0-1.7 mm. In a most preferred embodiment, the particle size is 0.5-1 mm. β-TCP having a granule size of less than 0.1 mm is not appropriate because it will be readily displaced by flowing body fluids. On the other hand, although bone formation is more obvious in larger particles, β-TCP having a granule size greater than 2 mm is also not appropriate because too many or excessively large gaps will form between the granules, thus preventing the effective coalescence of the β-TCP to the newly synthesized bone.

The porosity of the β-TCP influences the resorption rate. If the porosity is too high, the strength of the granules will be decreased. If the porosity is too low, the rate of resorption will be slow. The total porosity is measured using the mercury intrusion parameter method or equivalent methods. In one embodiment, the total porosity is in the range of 5-80%. In another embodiment, the total porosity is in the range of 40-80%. In a more preferred embodiment, the total porosity is 65-75%. In a most preferred embodiment, the total porosity is 70%.

The porous β-TCP of this invention may also be combined with one or more bioactive agents. The bioactive agent may be an agent that enhances bone growth or a substance that is medically useful or combinations thereof. It is envisioned that the bioactive agent can include but is not limited to bone morphogenic proteins, growth factors such as EGF, PDGF, IGF, FGF, TGF-α and TGF-β, cytokines, MPSF, hormones, peptides, lipids, trophic agents and therapeutic compositions including antibiotics and chemotherapeutic agents, insulin, chemoattractant, chemotactic factors, enzymes, enzyme inhibitors. It is also envisioned that bioactive agents such as vitamins, cytoskeletal agents, cartilage fragments, allografts, autografts, living cells such as chondrocytes, bone marrow cells, mesenchymal stem cells, tissue transplants, immunosuppressants may be added to the porous β-TCP.

In one embodiment, the bioactive agent is a bone morphogenic protein. In a preferred embodiment, the bone morphogenic protein is OP-1 (BMP-7), OP-2, OP-3, COP-1, COP-3, COP-4, COP-5, COP-7, COP-16, BMP-2, BMP-3, BMP-3b, BMP-4, BMP-5, BMP-6, BMP-9, BMP-10, BMP-11, BMP-12, BMP-13, BMP-14, BMP-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsalin-1, DPP, Vg-1, Vgr-1, 60A protein, NODAL, UNIVIN, SCREW, ADMP, NEURAL, and TGF-β. In a more preferred embodiment, the morphogenic protein is OP-1.

In another embodiment the morphogenic activity of the bone morphogenic protein is enhanced by the addition of a MPSF. In a preferred embodiment the MPSF is selected from the group consisting of insulin-like growth factor I (IGF-I), estradiol, fibroblast growth factor (FGF), growth hormone (GH), growth and differentiation factor (GDF), hydrocortisone (HC), insulin, progesterone, parathyroid hormone (PTH), vitamin D, retinoic acid and IL-6. In a preferred embodiment, the MPSF is selected from IGF-1, IL-6, FGF, PTH. In a more preferred embodiment, the MPSF is IGF-1.

In another embodiment, the bioactive agent is preferably an antimicrobial or antibiotic including but not limited to erythromycin, bacitracin, neomycin, penicillin, polymyxin B, tetracycline, viomycin, chloromycetin and streptomycin, cefazolin, ampicillin, azactam, tobramycin, clindamycin and gentamycin. The concentrations of the antibiotic to be used are well known in the art. Such antibiotics have been known and used in connection with bone cement materials. See, for example, Hoff et al., *J. Bone Joint Surg.,* 63A, pp. 798, (1981); and Dueland et al., *Clin. Orthop.,* 169, pp. 264-268, (1982). The teachings of these two references are incorporated herein by reference.

In another preferred embodiment, the bioactive agent is a repair cell. In a preferred embodiment, the repair cell is a mammalian cell, more preferably, a human cell of the same type as that of the tissue being repaired or reconstructed. Suitable examples of repair cells include bone cells such as bone marrow stem cells, osteocytes, osteoblasts, osteoclasts and bone progenitor cells. In another embodiment, the cell is transfected with a nucleic acid molecule encoding a BMP.

In yet another preferred embodiment, the bioactive agent is a nucleic acid molecule comprising a sequence encoding a BMP, preferably, OP-1 (SEQ ID NO: 10). In a preferred embodiment, the nucleic acid molecule is a RNA or DNA molecule. The nucleic acid sequence encoding the BMP may be inserted in recombinant expression vectors. Examples of vectors include but are not limited to pBR322, pH717, pH731, pH752, pH754 and pW24. SP6 vectors may be used for in vitro transcription of RNA. Transcription promoters useful for expressing the BMP include but are not limited to the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially. The DNA sequence may also be inserted in the genome of a recombinant virus such as, for example recombinant adenovirus, adeno-associated virus or retrovirus. The repair cell or bone progenitor cell is then transfected or infected with the vector or virus and expresses the BMP protein. The nucleic acid sequence may transiently or stably transfect the repair cell or bone progenitor cell.

In one embodiment, the nucleic acid molecule is directly injected into the implant site. Preferably, the nucleic acid is trapped in a carrier selected from the group consisting of mannitol, sucrose, lactose, trehalose, liposomes, proteoliposomes that contain viral envelope proteins and polylysine-glycoprotein complexes. See, e.g., Ledley, *J. Pediatrics* 110, pp. 1 (1987); Nicolau et al., *Proc. Natl. Acad. Sci. U.S.A.*, 80, pp. 1068 (1983). In another preferred embodiment, the nucleic acid is transfected or infected into target cells such as bone progenitor cells and repair cells that have been removed from the body. The transfected cell or infected cells are then re-implanted into the body.

In a most preferred embodiment, the bioactive agent is encapsulated in a biodegradable agent. As the biodegradable agent is slowly resorbed by the osteoclast cells, the encapsulated bioactive agent is gradually released into the matrix. At the implant site, one may deliver the bioactive agent through a combination of different biodegradable agents, preferably, differing in the rate of resorption, to achieve a multiple boost delivery system. In another preferred embodiment, the biodegradable agent is multi-layered. Each layer comprises a different biodegradable agent, preferably, differing in the rate of resorption. Methods of encapsulating the bioactive agent include but are not limited to the emulsion-solvent evaporation method (Grandfils et al., *Journal of Biomedical Materials Research*, 26, pp. 467-479 (1992)) and the method described in Herbert et al., *Pharmaceutical Research*, 15, pp. 357-361 (1998). The above references are incorporated herein by reference. The latter method is especially suitable for encapsulating proteins. Other methods are described in U.S. Pat. Nos. 6,110,503, 5,654,008 and 5,271,961, which are incorporated herein by reference. In a preferred embodiment, the OP-1 is stabilized by the addition of lactose during the encapsulation process.

The biodegradable agents of this invention may be in bead or microsphere form. The biodegradable agents can be resorbable biocompatible polymers including both natural and synthetic polymers. Natural polymers are typically absorbed by enzymatic degradation in the body, while synthetic resorbable polymers typically degrade by a hydrolytic mechanism. It is preferred that the particle size of the biodegradable agent is 20-500 µm, preferably, 20-140 µm, more preferably 50-140 µm, and most preferably 75-140 µm.

In one embodiment, the biodegradable agent is selected from the group consisting of ethylenevinylacetate, natural and synthetic collagen, poly(glaxanone), poly(phosphazenes), polyglactin, polyglactic acid, polyaldonic acid, polyacrylic acids, polyalkanoates, polyorthoesters, poly(L-lactide) (PLLA), poly(D,L-lactide) (PDLLA), polyglycolide (PGA), poly(lactide-co-glycolide (PLGA), poly(ζ-caprolactone), poly(trimethylene carbonate), poly(p-dioxanone), poly(ζ-caprolactone-co-glycolide), poly(glycolide-co-trimethylene carbonate) poly(D,L-lactide-co-trimethylene carbonate), polyarylates, polyhydroxybutyrate (PHB), polyanhydrides, poly(anhydride-co-imide) and co-polymers thereof, polymers of amino acids, propylene-co-fumarates, a polymer of one or more α-hydroxy carboxylic acid monomers, bioactive glass compositions, admixtures thereof and any derivatives and modifications thereof. Preferably, the modification changes less than 50% of the overall structure of the polymer.

In a preferred embodiment, the biodegradable agent is selected from the group consisting of polyorthoesters, poly (L-lactide)(PLLA), poly(D,L-lactide) (PDLLA), polyglycolide (PGA), poly(lactide-co-glycolide (PLGA), poly(ζ-caprolactone), poly(trimethylene carbonate), poly(p-dioxanone), poly(ζ-caprolactone-co-glycolide), poly(glycolide-co-trimethylene carbonate), poly(D,L-lactide-co-trimethylene carbonate), polyarylates and co-polymers thereof.

In another more preferred embodiment, the biodegradable agent is selected from the group consisting of poly(glaxanone), poly(phosphazenes), ethylenevinylacetate, polyglactin, polyglactic acid, polyaldonic acid, polyacrylic acids, polyalkanoates, co-polymers thereof and natural and synthetic collagen.

In yet another more preferred embodiment the biodegradable agent is selected from the group consisting of polyhydroxybutyrate (PHB), anhydrides including polyanhydrides, poly(anhydride-co-imide) and co-polymers thereof, polymers of amino acids, propylene-co-fumarates, a polymer of one or more -hydroxy carboxylic acid monomers, (e.g. α-hydroxy acetic acid (glycolic acid) and/or α-hydroxy propionic acid (lactic acid)), bioactive glass compositions. α-hydroxy propionic acid can be employed in its d- or l-form, or as a racemic mixture.

In a most preferred embodiment the biodegradable agent is poly(lactide-co-glycolide) (PLGA). Depending upon the desired rate of release of the bioactive agent, the molar ratio of the lactide, glycolide monomers can be adjusted. In a preferred embodiment, the monomer ratio is 50:50. In general, the higher the molecular weight, the slower the biodegradation. Preferably, the molecular weight range of the polymer is from about 5,000 to 500,000 daltons, more preferably 10,000 to 30,000 daltons.

Method of Producing Porous β-TCP

The invention also relates to a method of producing porous β-TCP granules. The TCP used in preparing the porous β-TCP is prepared according to known methods in the art. The TCP is harvested via a spray dryer, preferably to a particle size of less than 10 µm. If the particle size is too large, it will interfere with the formation of pores.

The fine TCP powder is then mixed with a pore-forming agent that decomposes at high temperature into gaseous decomposition products without leaving any solid residue. The pore-forming agents of this invention may be in bead or resin form. In one embodiment, the pore-forming agents are selected from thermally decomposable material such as naphthalene, prepolymers of polyacrylates, prepolymers of polymethacrylates, polymethyl methacrylate, copolymers of methyl acrylate and methyl methacrylate and mixtures thereof, polystyrene, polyethylene glycol, crystalline cellulose powder, fibrous cellulose, polyurethanes, polyethylenes, nylon resins and acrylic resins. In a more preferred embodiment the pore-forming agent is selected from the group consisting of polymethyl methacrylate, polystyrene and polyethylene glycol. It is preferred that the pore-forming agent creates a pore size diameter of 20-500 µm, more preferably 40-190 µm, and most preferably 50-125 µm after sintering.

The proportion and particle size of the pore-forming agent influences the porosity and the pore structure. An excessive amount of the pore-forming agent leads to interconnected pores and a decrease in density of the β-TCP body and hence mechanical strength of the sintered body. A deficiency in the amount of the pore-forming agent may result in the insufficiently developed pore structure. The proportion of pore-forming agent is preferably 10-50% by weight, more preferably 30-40% by weight, most preferably 37.5% by weight.

A granulating solution is then added to the mixture of TCP powder and pore-forming agent to produce a crumbly mass. This improves the sieving procedure that follows. Depending on the desired viscosity to be achieved and the aqueous properties of the dispersing medium, the compound used to form the granulating solution may be selected from the group consisting of polyvinyl pyrrolidone, starch, gelatin, polyvinyl alcohol, polyethylene oxide, hydroxyethyl cellulose, polyvinyl butyral and cellulose acetate butyrate. Preferably, the compound in the granulating solution is selected from the group consisting of polyvinyl pyrrolidone, starch and gelatin.

The crumbly mass is then sieved to select for a range of granule sizes. The size of the granules selected by the sieving process may be in the range of 250-1700 µm, more preferably 1000-1700 µm, most preferably 500-1000 µm. The sieved granules are then dried at 90-110° C., more preferably at 105° C.

The dried granules are then heated to 700-800° C. to remove the pore-forming agent. The temperature is then raised to 1000-1200° C., more preferably 1150° C., for sintering. The sintered granules undergo a slow cooling procedure to attain pure crystalline β-TCP. In a preferred embodiment the temperature is lowered from 1150° C. to 39° C. in 6 hours. After sintering, weight loss and shrinkage takes place in the sample. Pores are formed in the TCP and the pores are surrounded by the skeleton of sintered TCP. The sintered granules are resieved using the same size sieve as previously used and mixed with a binder as previously described to form a moldable putty composition.

Alternatively, the porous β-TCP granules may be prepared by mixing the TCP powder with the pore-forming agent. The mixture is blended to achieve homogeneity and pressed into slugs using a press, rotary tablet machine or chilsonators. The slugs are heated to 700-800° C. to remove the pore-forming agent and sintered at 1000-1100° C., preferably at 1150° C. The porous slugs are then fractured into the appropriate particle size range of 250-1700 µm, more preferably 1000-1700 µm, and most preferably 500-1000 µm. The porous granules are then mixed with a binder to form a moldable putty composition.

Moldable Putty Composition

The porous β-TCP of this invention may be combined with a biocompatible binder to form a moldable putty composition. The moldable putty may be in the form of a paste or a semi-solid having sufficient viscosity. The moldable putty composition enables the positioning and shaping within the voids, defects or other areas in which new bone growth is desired. The cohesiveness of the putty also prevents the problems of particle migration associated with grafting materials for orthopedic, maxillofacial and dental applications.

The binder according to this invention must be biodegradable, biocompatible and have fluid flow properties. The binders contemplated as useful herein include, but are not limited to: art-recognized suspending agents, viscosity-producing agents, gel-forming agents and emulsifying agents. Other candidates are agents used to suspend ingredients for topical, oral or parental administration. Yet other candidates are agents useful as tablet binders, disintegrants or emulsion stabilizers. Still other candidates are agents used in cosmetics, toiletries and food products. Reference manuals such as the USP XXII-NF XVII (*The Nineteen Ninety U.S. Pharmacopeia and the National Formulary* (1990)) categorize and describe such agents. Preferred binders include resorbable macromolecules from biological or synthetic sources including sodium alginate, hyaluronic acid, cellulose derivatives such as alkylcelluloses including methylcellulose, carboxy methylcellulose, carboxy methylcellulose sodium, carboxy methylcellulose calcium or other salts, hydroxy alkylcelluloses including hydroxypropyl methylcellulose, hydroxybutyl methylcellulose, hydroxyethyl methylcellulose, hydroxyethyl cellulose, alkylhydroxyalkyl celluloses including methylhydroxyethyl cellulose, collagen, peptides, mucin, chrondroitin sulfate and the like.

Carboxymethylcellulose (CMC) sodium is a preferred binder. CMC is commercially available from suppliers such as, but not limited to: Hercules Inc., Aqualon® Division, Delaware; FMC Corporation, Pennsylvania; British Celanese, Ltd., United Kingdom; and Henkel KGaA, United Kingdom. Carboxymethylcellulose sodium is the sodium salt of a polycarboxymethyl ether of cellulose with a typical molecular weight ranging from 90,000-700,000. Various grades of carboxymethylcellulose sodium are commercially available which have differing viscosities. Viscosities of various grades of carboxymethylcellulose sodium are reported in *Handbook of Pharmaceutical Excipients* (2nd Edition), American Pharmaceutical Association & Royal Pharmaceutical Society of Great Britain. For example, low viscosity 50-200 cP, medium viscosity 400-800 cP, high viscosity 1500-3000 cP. A number of grades of carboxymethylcellulose sodium are commercially available, the most frequently used grade having a degree of substitution (DS) of 0.7. The DS is defined as the average number of hydroxyl groups substituted per anhydroglucose unit. It is this DS which determines the aqueous solubility of the polymer. The degree of substitution and the standard viscosity of an aqueous solution of stated concentration is indicated on any carboxymethylcellulose sodium labeling. Low viscosity CMC (Aqualon® Division, Hercules, Inc., Wilmington, Del.) is currently preferred. The currently preferred degrees of substitution range from 0.65-0.90 (DS=0.7, Aqualon® Type 7L).

Aside from binders that are flowable at room temperature, binders also include reagents such as gelatin, that are solubilized in warm or hot aqueous solutions, and are transformed into a non-flowable gel upon cooling. The gelatin composition is formulated so that the composition is flowable at temperatures above the body temperature of the mammal for implant, but transitions to relatively non-flowable gel at or slightly above such body temperature.

In one embodiment, the binder of this invention is selected from a class of high molecular weight hydrogels including sodium hyaluronate (~500-3000 kD), chitosan (~100-300 kD), poloxamer (~7-18 kD), and glycosaminoglycan (~2000-3000 kD). In a preferred embodiment, the glycosaminoglycan is N,O-carboxymethylchitosan glucosamine. Hydrogels are cross-linked hydrophilic polymers in the form of a gel which have a three-dimensional network. Hydrogel matrices can carry a net positive or net negative charge, or may be neutral. A typical net negative charged matrix is alginate. Hydrogels carrying a net positive charge may be typified by extracellular matrix components such as collagen and laminin. Examples of commercially available extracellular matrix components include Matrigel™ (Dulbecco's modified eagle's medium with 50 μg/ml gentamicin) and Vitrogen™ (a sterile solution of purified, pepsin-solubilized bovine dermal collagen dissolved in 0.012 N HCL). An example of a net neutral hydrogel is highly crosslinked polyethylene oxide, or polyvinylalcohol.

In another embodiment, the binder of this invention may also be selected from a class of polymers selected from the group comprising polylactic acid, polyglycolic acid, co-polymers of polylactic acid and polyglycolic acid, polyhydroxybutyric acid, polymalic acid, polyglutamic acid, and polylactone. In order to have gradual polymer replacement in the material by in situ tissue ingrowth over a several-day to several-week period, the molecular weight of the polymer should be compatible with the required degradation rate of the polymer.

In another preferred embodiment, the binder is polyethylene glycol. A mixture of low- and high-molecular-weight polyethylene glycols can produce a paste with the proper viscosity. For example, a mixture of polyethylene glycols of molecular weight 400-600 daltons and 1500 daltons at the proper ratio would be effective.

In yet another embodiment, the binder is selected from a class of polysaccharides with an average molecular weight of about 200,000 to 5,000,000 daltons consisting of dextran, dextran sulfate, diethylaminoethyl dextran, dextran phosphate or mixtures thereof. Lower molecular weight polysaccharides have the advantage of a faster dextran absorption rate, resulting in earlier exposure of the porous β-TCP material. If it is desired that dextrans remain in the site for an extended period, dextrans of relatively high molecular weight may be used. Other preferred polysaccharides include starch, fractionated starch, amylopectin, agar, gum arabic, pullullan, agarose, carrageenan, dextrins, fructans, inulin, mannans, xylans, arabinans, glycogens, glucans, xanthan gum, guar gum, locust bean gum, tragacanth gum, karaya gum, and derivatives and mixtures thereof.

In another preferred embodiment, the binder is selected from the group consisting of mannitol, white petrolatum, mannitol/dextran combinations, mannitol/white petrolatum combinations, sesame oil, fibrin glue and admixtures thereof. Fibrin glue is currently a preferred binder, which comprises a mixture of mammalian fibrinogen and thrombin. Human fibrinogen is commercially available in products such as, but not limited to Tissucol® (Immuno AG, Vienna, Austria), Beriplast® (Behringwerke, Marburg, Germany), Biocoll® (Centre de Transfusion Sanguine de Lille, Pours, France) and Transglutine® (CNTS Fractionation Centre, Strasbourg, France). Fibrin glue may also be made of fibrinogen and thrombin from other mammalian sources, such as, for example, bovine and murine sources.

It is preferred that the binder is selected from the group consisting of sodium alginate, hyaluronic acid, sodium hyaluronate, gelatin, collagen, peptides, mucin, chrondroitin sulfate, chitosan, poloxamer, glycosaminoglycan, polysaccharide, polyethylene glycol, methylcellulose, carboxy methylcellulose, carboxy methylcellulose sodium, carboxy methylcellulose calcium, hydroxypropyl methylcellulose, hydroxybutyl methylcellulose, hydroxyethyl methylcellulose, hydroxyethylcellulose, methylhydroxyethyl cellulose, hydroxyethyl cellulose, polylactic acid, polyglycolic acid, co-polymers of polylactic acid and polyglycolic acid, polyhydroxybutyric acid, polymalic acid, polyglutamic acid, polylactone, mannitol, white petrolatum, mannitol/dextran combinations, mannitol/white petrolatum combinations, sesame oil, fibrin glue and admixtures thereof.

More preferably, the binder is selected from the group consisting of sodium alginate, hyaluronic acid, methylcellulose, carboxy methylcellulose, carboxy methylcellulose sodium, carboxy methylcellulose calcium, hydroxypropyl methylcellulose, hydroxybutyl methylcellulose, hydroxyethyl methylcellulose, hydroxyethylcellulose, methylhydroxyethyl cellulose, hydroxyethyl cellulose and admixtures thereof. Most preferably, the binder is selected from the group consisting of sodium alginate, hyaluronic acid, carboxy methylcellulose, carboxy methylcellulose sodium and carboxy methylcellulose calcium.

The minimum amount of binder is the amount necessary to give easy formability and provide sufficient particle cohesion and shape retention during the period of tissue ingrowth. In one embodiment, the weight ratio of porous β-TCP to carboxy methylcellulose sodium is in the range of 1:0.1 to 1:1.25. In a preferred embodiment, the ratio of porous β-TCP to CMC sodium is 1:0.4.

The invention also relates to a kit for bone implant comprising the porous β-TCP material of the invention and at least one additional bioactive agent selected from the group consisting of bone morphogenic proteins and antibiotics. The kit comprising the porous β-TCP material and a bone morphogenic protein may further comprise a morphogenic protein stimulatory factor. In one embodiment, the kit further comprises a binder. In another embodiment, the kit comprises the porous β-TCP material of the invention and a binder.

Bone Morphogenic Protein Family

The BMP family, named for its representative bone morphogenic/osteogenic protein family members, belongs to the TGF-β protein superfamily. Of the reported "BMPs" (BMP-1 to BMP-18), isolated primarily based on sequence homology, all but BMP-1 remain classified as members of the BMP family of morphogenic proteins (Ozkaynak et al., *EMBO J.*, 9, pp. 2085-93 (1990)).

The BMP family includes other structurally-related members which are morphogenic proteins, including the *drosophila* decapentaplegic gene complex (DPP) products, the Vg1 product of *Xenopus laevis* and its murine homolog, Vgr-1 (see, e.g., Massagué, *Annu. Rev. Cell Biol.*, 6, pp. 597-641 (1990), incorporated herein by reference).

The C-terminal domains of BMP-3, BMP-5, BMP-6, and OP-1 (BMP-7) are about 60% identical to that of BMP-2, and the C-terminal domains of BMP-6 and OP-1 are 87% identical. BMP-6 is likely the human homolog of the murine Vgr-1 (Lyons et al., *Proc. Natl. Acad. Sci. U.S.A.*, 86, pp. 4554-59 (1989)); the two proteins are 92% identical overall at the amino acid sequence level (U.S. Pat. No. 5,459,047, incorporated herein by reference). BMP-6 is 58% identical to the *Xenopus* Vg-1 product.

Biochemical Structural and Functional Properties of Bone Morphogenic Proteins

The naturally occurring bone morphogens share substantial amino acid sequence homology in their C-terminal regions (domains). Typically, the above-mentioned naturally occurring osteogenic proteins are translated as a precursor, having an N-terminal signal peptide sequence typically less than about 30 residues, followed by a "pro" domain that is cleaved to yield the mature C-terminal domain of approximately 100-140 amino acids. The signal peptide is cleaved rapidly upon translation, at a cleavage site that can be predicted in a given sequence using the method of Von Heijne *Nucleic Acids Research,* 14, pp. 4683-4691 (1986). The pro domain typically is about three times larger than the fully processed mature C-terminal domain.

Another characteristic of the BMP protein family members is their apparent ability to dimerize. Several bone-derived osteogenic proteins (OPs) and BMPs are found as homo- and heterodimers in their active forms. The ability of OPs and BMPs to form heterodimers may confer additional or altered morphogenic inductive capabilities on morphogenic proteins. Heterodimers may exhibit qualitatively or quantitatively different binding affinities than homodimers for OP and BMP receptor molecules. Altered binding affinities may in turn lead to differential activation of receptors that mediate different signaling pathways, which may ultimately lead to different biological activities or outcomes. Altered binding affinities could also be manifested in a tissue or cell type-specific manner, thereby inducing only particular progenitor cell types to undergo proliferation and/or differentiation.

In preferred embodiments, the pair of morphogenic polypeptides have amino acid sequences each comprising a sequence that shares a defined relationship with an amino acid sequence of a reference morphogen. Herein, preferred osteogenic polypeptides share a defined relationship with a sequence present in osteogenically active human OP-1, SEQ ID NO: 1 (encoded by SEQ ID NO: 10). However, any one or more of the naturally occurring or biosynthetic sequences disclosed herein similarly could be used as a reference sequence. Preferred osteogenic polypeptides share a defined relationship with at least the C-terminal six cysteine domain of human OP-1, residues 335-431 of SEQ ID NO: 1. Preferably, osteogenic polypeptides share a defined relationship with at least the C-terminal seven cysteine domain of human OP-1, residues 330-431 of SEQ ID NO: 1. That is, preferred polypeptides in a dimeric protein with bone morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference sequence, e.g., the C-terminal seven cysteine domain (also referred to herein as the conserved seven cysteine skeleton) of human OP-1, provided that this difference does not destroy bone morphogenic activity. Accordingly, conservative substitutions of corresponding amino acids in the reference sequence are preferred. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al., supra, the teachings of which are incorporated by reference herein.

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative variation" also includes the use of a substituted amino acid in place of an unsubstituted parent amino acid provided that antibodies raised to the substituted polypeptide also immunoreact with the unsubstituted polypeptide.

The osteogenic protein OP-1 has been described (see, e.g., Oppermann et al., U.S. Pat. No. 5,354,557, incorporated herein by reference). Natural-sourced osteogenic protein in its mature, native form is a glycosylated dimer typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptides, having molecular weights of about 14 kDa to 16 kDa, capable of inducing endochondral bone formation in a mammal. Osteogenic proteins may include forms having varying glycosylation patterns, varying N-termini, and active truncated or mutated forms of native protein. As described above, particularly useful sequences include those comprising the C-terminal 96 or 102 amino acid sequences of DPP (from *Drosophila*), Vg1 (from *Xenopus*), Vgr-1 (from mouse), the OP-1 and OP-2 proteins, (see U.S. Pat. No. 5,011,691 and Oppermann et al., incorporated herein by reference), as well as the proteins referred to as BMP-2, BMP-3, BMP-4 (see WO88/00205, U.S. Pat. No. 5,013,649 and WO91/18098, incorporated herein by reference), BMP-5 and BMP-6 (see WO90/11366, PCT/US90/01630, incorporated herein by reference), BMP-8 and BMP-9.

Preferred morphogenic and osteogenic proteins of this invention comprise at least one polypeptide selected from the group consisting of OP-1 (BMP-7), OP-2, OP-3, COP-1, COP-3, COP-4, COP-5, COP-7, COP-16, BMP-2, BMP-3, BMP-3b, BMP-4, BMP-5, BMP-6, BMP-9, BMP-10, BMP-11, BMP-12, BMP-13, BMP-14, BMP-15, BMP-16, BMP-17, BMP-18, GDF-1, GDF-2, GDF-3, GDF-5, GDF-6, GDF-7, GDF-8, GDF-9, GDF-10, GDF-11, GDF-12, MP121, dorsalin-1, DPP, Vg-1, Vgr-1, 60A protein, NODAL, UNIVIN, SCREW, ADMP, NEURAL, TGF-β and amino acid sequence variants and homologs thereof, including species homologs, thereof. Preferably, the morphogenic protein comprises at least one polypeptide selected from the group consisting of OP-1 (BMP-7), BMP-2, BMP-4, BMP-5 and BMP-6; more preferably, OP-1 (BMP-7) and BMP-2; and most preferably, OP-1 (BMP-7).

Publications disclosing these sequences, as well as their chemical and physical properties, include: OP-1 and OP-2 (U.S. Pat. No. 5,011,691; U.S. Pat. No. 5,266,683; Ozkaynak et al., *EMBO J.,* 9, pp. 2085-2093 (1990); OP-3 (WO94/10203 (PCT US93/10520)), BMP-2, BMP-3, BMP-4, (WO88/00205; Wozney et al. *Science,* 242, pp. 1528-1534 (1988)), BMP-5 and BMP-6, (Celeste et al., *PNAS,* 87, 9843-9847 (1991)), Vgr-1 (Lyons et al., *PNAS,* 86, pp. 4554-4558 (1989)); DPP (Padgett et al. *Nature,* 325, pp. 81-84 (1987)); Vg-1 (Weeks, *Cell,* 51, pp. 861-867 (1987)); BMP-9 (WO95/33830 (PCT/US95/07084); BMP-10 (WO94/26893 (PCT/US94/05290); BMP-11 (WO94/26892 (PCT/US94/05288); BMP-12 (WO95/16035 (PCT/US94/14030); BMP-13 (WO95/16035 (PCT/US94/14030); GDF-1 (WO92/00382

(PCT/US91/04096) and Lee et al. *PNAS,* 88, pp. 4250-4254 (1991); GDF-8 (WO94/21681 (PCT/US94/03019); GDF-9; (WO94/15966 (PCT/US94/00685); GDF-10 (WO95/10539 (PCT/US94/11440); GDF-11 (WO96/01845 (PCT/US95/08543); BMP-15 (WO96/36710 (PCT/US96/06540); MP-121 (WO96/01316 (PCT/EP95/02552); GDF-5 (CDMP-1, MP52) (WO94/15949 (PCT/US94/00657) and WO96/14335 (PCT/US94/12814) and WO93/16099 (PCT/EP93/00350)); GDF-6 (CDMP-2, BMP13) (WO95/01801 (PCT/US94/07762) and WO96/14335 and WO95/10635 (PCT/US94/14030)); GDF-7 (CDMP-3, BMP12) (WO95/10802 (PCT/US94/07799) and WO95/10635 (PCT/US94/14030)) The above publications are incorporated herein by reference. In another embodiment, useful proteins include biologically active biosynthetic constructs, including novel biosynthetic morphogenic proteins and chimeric proteins designed using sequences from two or more known morphogens.

In another embodiment of this invention, a morphogenic protein may be prepared synthetically for use in concert with a MPSF to induce tissue formation. Morphogenic proteins prepared synthetically may be native, or may be non-native proteins, i.e., those not otherwise found in nature.

Non-native osteogenic proteins have been synthesized using a series of consensus DNA sequences (U.S. Pat. No. 5,324,819, incorporated herein by reference). These consensus sequences were designed based on partial amino acid sequence data obtained from natural osteogenic products and on their observed homologies with other genes reported in the literature having a presumed or demonstrated developmental function.

Several of the biosynthetic consensus sequences (called consensus osteogenic proteins or "COPs") have been expressed as fusion proteins in prokaryotes. Purified fusion proteins may be cleaved, refolded, combined with at least one MPSF (optionally in a matrix or device), implanted in an established animal model and shown to have bone- and/or cartilage-inducing activity. The currently preferred synthetic osteogenic proteins comprise two synthetic amino acid sequences designated COP-5 (SEQ. ID NO: 2) and COP-7 (SEQ. ID NO: 3)

Oppermann et al., U.S. Pat. Nos. 5,011,691 and 5,324,819, which are incorporated herein by reference, describe the amino acid sequences of COP-5 (SEQ ID NO: 2) and COP-7 (SEQ ID NO: 3) as shown below:

```
COP5    LYVDFS-DVGWDDWIVAPPGYQAFYCHGECPFPLAD
COP7    LYVDFS-DVGWNDWIVAPPGYHAFYCHGECPFPLAD

COP5    HFNSTN--H-AVVQTLVNSVNSKI--PKACCVPTELSA
COP7    HLNSTN--H-AVVQTLVNSVNSKI--PKACCVPTELSA

COP5    ISMLYLDENEKVVLKYNQEMVVEGCGCR
COP7    ISMLYLDENEKVVLKYNQEMVVEGCGCR
```

In these amino acid sequences, the dashes (-) are used as fillers only to line up comparable sequences in related proteins. Differences between the aligned amino acid sequences are highlighted.

The DNA and amino acid sequences of these and other BMP family members are published and may be used by those of skill in the art to determine whether a newly identified protein belongs to the BMP family. New BMP-related gene products are expected by analogy to possess at least one morphogenic activity and thus classified as a BMP.

In one preferred embodiment of this invention, the morphogenic protein comprises a pair of subunits disulfide bonded to produce a dimeric species, wherein at least one of the subunits comprises a recombinant peptide belonging to the BMP protein family. In another preferred embodiment of this invention, the morphogenic protein comprises a pair of subunits that produce a dimeric species formed through non-covalent interactions, wherein at least one of the subunits comprises a recombinant peptide belonging to the BMP protein family. Non-covalent interactions include Van der Waals, hydrogen bond, hydrophobic and electrostatic interactions. The dimeric species may be a homodimer or heterodimer and is capable of inducing cell proliferation and/or tissue formation.

In certain preferred embodiments, bone morphogenic proteins useful herein include those in which the amino acid sequences comprise a sequence sharing at least 70% amino acid sequence homology or "similarity", and preferably 80% homology or similarity, with a reference morphogenic protein selected from the foregoing naturally occurring proteins. Preferably, the reference protein is human OP-1, and the reference sequence thereof is the C-terminal seven cysteine domain present in osteogenically active forms of human OP-1, residues 330-431 of SEQ ID NO: 1. In certain embodiments, a polypeptide suspected of being functionally equivalent to a reference morphogen polypeptide is aligned therewith using the method of Needleman, et al., supra, implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservation substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is OP-1. Bone morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins, including those set forth and identified above. Certain particularly preferred morphogenic polypeptides share at least 60% amino acid identity with the preferred reference sequence of human OP-1, still more preferably at least 65% amino acid identity therewith.

In another embodiment, useful osteogenic proteins include those sharing the conserved seven cysteine domain and sharing at least 70% amino acid sequence homology (similarity) within the C-terminal active domain, as defined herein. In still another embodiment, the osteogenic proteins of the invention can be defined as osteogenically active proteins having any one of the generic sequences defined herein, including OPX (SEQ ID NO: 4) and Generic Sequences 7 (SEQ ID NO: 5) and 8 (SEQ ID NO: 6), or Generic Sequences 9 (SEQ ID NO: 7) and 10 (SEQ ID NO: 8).

The family of bone morphogenic polypeptides useful in the present invention, and members thereof, can be defined by a generic amino acid sequence. For example, Generic Sequence 7 (SEQ ID NO: 5) and Generic Sequence 8 (SEQ ID NO: 6) are 97 and 102 amino acid sequences, respectively, and accommodate the homologies shared among preferred protein family members identified to date, including at least OP-1, OP-2, OP-3, CBMP-2A, CBMP-2B, BMP-3, 60A, DPP, Vg1, BMP-5, BMP-6, Vgr-1, and GDF-1. The amino acid sequences for these proteins are described herein and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 36 (Generic Sequence 7) or position 41 (Generic Sequence 8), thereby encompassing the morphogenically active sequences of OP-2 and OP-3.

```
              Generic Sequence 7
                                      (SEQ ID NO: 5)
              Leu Xaa Xaa Xaa Phe Xaa Xaa
              1                   5

Xaa Gly Trp Xaa Xaa Xaa Xaa Xaa Xaa Pro
           10                      15

Xaa Xaa Xaa Xaa Ala Xaa Tyr Cys Xaa Gly
           20                      25

Xaa Cys Xaa Xaa Pro Xaa Xaa Xaa Xaa Xaa
           30                      35

Xaa Xaa Xaa Asn His Ala Xaa Xaa Xaa Xaa
           40                      45

Xaa Xaa Xaa Xaa Xaa Xaa Xaa Xaa Xaa Xaa
           50                      55

Xaa Xaa Xaa Cys Cys Xaa Pro Xaa Xaa Xaa
           60                      65

Xaa Xaa Xaa Xaa Xaa Leu Xaa Xaa Xaa Xaa
           70                      75

Xaa Xaa Xaa Val Xaa Leu Xaa Xaa Xaa Xaa
           80                      85

Xaa Met Xaa Val Xaa Xaa Cys Xaa Cys Xaa
           90                      95
``` wherein each Xaa independently is selected from a group of one or more specified amino acids defined as follows: "res." means "residue" and Xaa at res.2=(Tyr or Lys); Xaa at res.3=(Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res. 11=(Gln, Leu, Asp, His, Asn or Ser); Xaa at res.12=(Asp, Arg, Asn or Glu); Xaa at res.13=(Trp or Ser); Xaa at res.14=(Ile or Val); Xaa at res.15=(Ile or Val); Xaa at res.16 (Ala or Ser); Xaa at res.18= (Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28= (Glu, Lys, Asp, Gln or Ala); Xaa at res.30=(Ala, Ser, Pro, Gln, Ile or Asn); Xaa at res.31=(Phe, Leu or Tyr); Xaa at res.33= (Leu, Val or Met); Xaa at res.34=(Asn, Asp, Ala, Thr or Pro); Xaa at res.35=(Ser, Asp, Glu, Leu, Ala or Lys); Xaa at res.36= (Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53=(Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76= (Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86=(Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala) and Xaa at res.97=(His or Arg).

Generic Sequence 8 (SEQ ID NO: 6) includes all of Generic Sequence 7 and in addition includes the following sequence (SEQ ID NO: 9) at its N-terminus:

```
                                      SEQ ID NO: 9
              Cys Xaa Xaa Xaa Xaa
              1                 5
```

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res.2=(Tyr or Lys)" in Generic Sequence 7 refers to Xaa at res. 7 in Generic Sequence 8. In Generic Sequence 8, Xaa at res.2=(Lys, Arg, Ala or Gln); Xaa at res.3=(Lys, Arg or Met); Xaa at res.4= (His, Arg or Gln); and Xaa at res. 5=(Glu, Ser, His, Gly, Arg, Pro, Thr, or Tyr).

In another embodiment, useful osteogenic proteins include those defined by Generic Sequences 9 and 10, defined as follows.

Specifically, Generic Sequences 9 and 10 are composite amino acid sequences of the following proteins: human OP-1, human OP-2, human OP-3, human BMP-2, human BMP-3, human BMP-4, human BMP-5, human BMP-6, human BMP-8, human BMP-9, human BMP-10, human BMP-11, *Drosophila* 60A, *Xenopus* Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, dpp, *Drosophila* SCREW, mouse NODAL, mouse GDF-8, human GDF-8, mouse GDF-9, mouse GDF-10, human GDF-11, mouse GDF-11, human BMP-15, and rat BMP3b. Like Generic Sequence 7, Generic Sequence 9 is a 97 amino acid sequence that accommodates the C-terminal six cysteine skeleton and, like Generic Sequence 8, Generic Sequence 10 is a 102 amino acid sequence which accommodates the seven cysteine skeleton.

```
            Generic Sequence 9
                                   (SEQ ID NO: 7)
  Xaa Xaa Xaa Xaa Xaa Xaa Xaa Xaa Xaa Xaa
  1               5                    10

Xaa Xaa Xaa Xaa Xaa Xaa Pro Xaa Xaa Xaa
                  15                   20

Xaa Xaa Xaa Xaa Cys Xaa Gly Xaa Cys Xaa
                  25                   30

Xaa Xaa Xaa Xaa Xaa Xaa Xaa Xaa Xaa Xaa
                  35                   40

Xaa Xaa Xaa Xaa Xaa Xaa Xaa Xaa Xaa Xaa
                  45                   50

Xaa Xaa Xaa Xaa Xaa Xaa Xaa Xaa Xaa Xaa
                  55                   60

Xaa Cys Xaa Pro Xaa Xaa Xaa Xaa Xaa Xaa
                  65                   70

Xaa Xaa Leu Xaa Xaa Xaa Xaa Xaa Xaa Xaa
                  75                   80

Xaa Xaa Xaa Xaa Xaa Xaa Xaa Xaa Xaa Xaa
                  85                   90

Xaa Xaa Xaa Cys Xaa Cys Xaa
                  95
``` wherein each Xaa is independently selected from a group of one or more specified amino acids defined as follows: "res." means "residue" and Xaa at res.1=(Phe, Leu or Glu); Xaa at res.2=(Tyr, Phe, His, Arg, Thr, Lys, Gln, Val or Glu); Xaa at res.3=(Val, Ile, Leu or Asp); Xaa at res.4=(Ser, Asp, Glu, Asn or Phe); Xaa at res.5=(Phe or Glu); Xaa at res.6=(Arg, Gln, Lys, Ser, Gln, Ala or Asn); Xaa at res.7=(Asp, Glu, Leu, Ala or Gln); Xaa at res.8=(Leu, Val, Met, Ile or Phe); Xaa at res.9=(Gly, His or Lys); Xaa at res.10=(Trp or Met); Xaa at res.11=(Gln, Leu, His, Gln, Asn, Asp, Ser or Gly); Xaa at res.12=(Asp, Asn, Ser, Lys, Arg, Glu or His); Xaa at res.13=(Trp or Ser); Xaa at res.14=(Ile or Val); Xaa at res.15=(Ile or Val); Xaa at res.16=(Ala, Ser, Tyr or Trp); Xaa at res.18=(Glu, Lys, Gln, Met, Pro, Leu, Arg, His or Lys); Xaa at res.19=(Gly, Glu, Asp, Lys, Ser, Gln, Arg or Phe); Xaa at res.20=(Tyr or Phe); Xaa at res.21=(Ala, Ser, Gly, Met, Gln, His, Glu, Asp, Leu, Asn, Lys or Thr); Xaa at res.22=(Ala or Pro); Xaa at res.23=(Tyr, Phe, Asn, Ala or Arg); Xaa at res.24=(Tyr, His, Glu, Phe or Arg); Xaa at res.26=(Glu, Asp, Ala, Ser, Tyr, His, Lys, Arg, Gln or Gly); Xaa at res.28=(Glu, Asp, Leu, Val, Lys, Gly, Thr, Ala or Gln); Xaa at res.30=(Ala, Ser, Ile, Asn, Pro, Glu, Asp, Phe, Gln or Leu); Xaa at res.31=(Phe, Tyr, Leu, Asn, Gly or Arg); Xaa at res.32=(Pro, Ser, Ala or Val); Xaa at res.33=(Leu, Met, Glu, Phe or Val); Xaa at res.34=(Asn, Asp, Thr, Gly, Ala, Arg, Leu or Pro); Xaa at res.35=(Ser, Ala, Glu, Asp, Thr, Leu, Lys, Gln or His); Xaa at res.36=(Tyr, His, Cys, Ile, Arg, Asp, Asn, Lys, Ser, Glu or Gly); Xaa at res.37=(Met, Leu, Phe, Val, Gly or Tyr); Xaa at res.38=(Asn, Glu, Thr, Pro, Lys, His, Gly, Met, Val or Arg); Xaa at res.39=(Ala, Ser, Gly, Pro or Phe); Xaa at res.40=(Thr, Ser, Leu, Pro, His or Met); Xaa at res.41=(Asn, Lys, Val, Thr or Gln); Xaa at res.42=(His, Tyr or Lys); Xaa at res.43=(Ala, Thr, Leu or Tyr); Xaa at res.44=(Ile, Thr, Val, Phe, Tyr, Met or Pro); Xaa at res.45=(Val, Leu, Met, Ile or His); Xaa at res.46=(Gln, Arg or Thr); Xaa at res.47=(Thr, Ser, Ala, Asn or His); Xaa at res.48=(Leu, Asn or Ile); Xaa at res.49=(Val, Met, Leu, Pro or Ile); Xaa at res.50=(His, Asn, Arg, Lys, Tyr or Gln); Xaa at res.51=(Phe, Leu, Ser, Asn, Met, Ala, Arg, Glu, Gly or Gln); Xaa at res.52=(Ile, Met, Leu, Val, Lys, Gln, Ala or Tyr); Xaa at res.53=(Asn, Phe, Lys, Glu, Asp, Ala, Gln, Gly, Leu or Val); Xaa at res.54=(Pro, Asn, Ser, Val or Asp); Xaa at res.55=(Glu, Asp, Asn, Lys, Arg, Ser, Gly, Thr, Gln, Pro or His); Xaa at res.56=(Thr, His, Tyr, Ala, Ile, Lys, Asp, Ser, Gly or Arg); Xaa at res.57=(Val, Ile, Thr, Ala, Leu or Ser); Xaa at res.58=(Pro, Gly, Ser, Asp or Ala); Xaa at res.59=(Lys, Leu, Pro, Ala, Ser, Glu, Arg or Gly); Xaa at res.60=(Pro, Ala, Val, Thr or Ser); Xaa at res.61=(Cys, Val or Ser); Xaa at res.63=(Ala, Val or Thr); Xaa at res.65=(Thr, Ala, Glu, Val, Gly, Asp or Tyr); Xaa at res.66=(Gln, Lys, Glu, Arg or Val); Xaa at res.67=(Leu, Met, Thr or Tyr); Xaa at res.68=(Asn, Ser, Gly, Thr, Asp, Glu, Lys or Val); Xaa at res.69=(Ala, Pro, Gly or Ser); Xaa at res.70=(Ile, Thr, Leu or Val); Xaa at res.71=(Ser, Pro, Ala, Thr, Asn or Gly); Xaa at res.72=(Val, Ile, Leu or Met); Xaa at res.74=(Tyr, Phe, Arg, Thr, Tyr or Met); Xaa at res.75=(Phe, Tyr, His, Leu, Ile, Lys, Gln or Val); Xaa at res.76=(Asp, Leu, Asn or Glu); Xaa at res.77=(Asp, Ser, Arg, Asn, Glu, Ala, Lys, Gly or Pro); Xaa at res.78=(Ser, Asn, Asp, Tyr, Ala, Gly, Gln, Met, Glu, Asn or Lys); Xaa at res.79=(Ser, Asn, Glu, Asp, Val, Lys, Gly, Gln or Arg); Xaa at res.80=(Asn, Lys, Thr, Pro, Val, Ile, Arg, Ser or Gln); Xaa at res.81=(Val, Ile, Thr or Ala); Xaa at res.82=(Ile, Asn, Val, Leu, Tyr, Asp or Ala); Xaa at res.83=(Leu, Tyr, Lys or Ile); Xaa at res.84=(Lys, Arg, Asn, Tyr, Phe, Thr, Glu or Gly); Xaa at res.85=(Lys, Arg, His, Gln, Asn, Glu or Val); Xaa at res.86=(Tyr, His, Glu or Ile); Xaa at res.87=(Arg, Glu, Gln, Pro or Lys); Xaa at res.88=(Asn, Asp, Ala, Glu, Gly or Lys); Xaa at res.89=(Met or Ala); Xaa at res.90=(Val, Ile, Ala, Thr, Ser or Lys); Xaa at res.91=(Val or Ala); Xaa at res.92=(Arg, Lys, Gln, Asp, Glu, Val, Ala, Ser or Thr); Xaa at res.93=(Ala, Ser, Glu, Gly, Arg or Thr); Xaa at res.95=(Gly, Ala or Thr); Xaa at res.97=(His, Arg, Gly, Leu or Ser). Further, after res.53 in rBMP3b and mGDF-I0 there is an Ile; after res.54 in GDF-1 there is a T; after res.54 in BMP3 there is a V; after res.78 in BMP-8 and Dorsalin there is a G; after res.37 in hGDF-1 there is Pro, Gly, Gly, Pro.

Generic Sequence 10 (SEQ ID NO: 8) includes all of Generic Sequence 9 (SEQ ID NO: 7) and in addition includes the following sequence (SEQ ID NO: 11) at its N-terminus:

```
                                       SEQ ID NO: 11
  Cys Xaa Xaa Xaa Xaa
  1               5
```

Accordingly, beginning with residue 6, each "Xaa" in Generic Sequence 10 is a specified amino acid defined as for Generic Sequence 9, with the distinction that each residue number described for Generic Sequence 9 is shifted by five in Generic Sequence 10. Thus, "Xaa at res. 1=(Tyr, Phe, His, Arg, Thr, Lys, Gln, Val or Glu)" in Generic Sequence 9 refers to Xaa at res. 6 in Generic Sequence 10. In Generic Sequence 10, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

As noted above, certain currently preferred bone morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the *Drosophila* 60A protein. Accordingly, in certain particularly preferred embodiments, useful morphogenic proteins include active proteins comprising pairs of polypeptide chains within the generic amino acid sequence herein referred to as "OPX" (SEQ ID NO: 4), which defines the seven cysteine skeleton and accommodates the homologies between several identified variants of OP-1 and OP-2. As described therein, each Xaa at a given position independently is selected from the residues occurring at the corresponding position in the C-terminal sequence of mouse or human OP-1 or OP-2.

```
                                              (SEQ ID NO: 4)
Cys Xaa Xaa His Glu Leu Tyr Val Ser Phe Xaa Asp
1               5                   10

Leu Gly Trp Xaa Asp Trp Xaa Ile Ala Pro Xaa Gly
            15          20

Tyr Xaa Ala Tyr Tyr Cys Glu Gly Glu Cys Xaa Phe
25              30                  35

Pro Leu Xaa Ser Xaa Met Asn Ala Thr Asn His Ala
            40              45

Ile Xaa Gln Xaa Leu Val His Xaa Xaa Xaa Pro Xaa
    50              55                  60

Xaa Val Pro Lys Xaa Cys Cys Ala Pro Thr Xaa Leu
                65              70

Xaa Ala Xaa Ser Val Leu Tyr Xaa Asp Xaa Ser Xaa
        75              80

Asn Val Ile Leu Xaa Lys Xaa Arg Asn Met Val Val
85              90                  95

Xaa Ala Cys Gly Cys His
                100
``` wherein Xaa at res.2=(Lys or Arg); Xaa at res.3=(Lys or Arg); Xaa at res.11=(Arg or Gln); Xaa at res.16=(Gln or Leu); Xaa at res.19=(Ile or Val); Xaa at res.23=(Glu or Gln); Xaa at res.26=(Ala or Ser); Xaa at res.35=(Ala or Ser); Xaa at res.39=(Asn or Asp); Xaa at res.41=(Tyr or Cys); Xaa at res.50=(Val or Leu); Xaa at res.52=(Ser or Thr); Xaa at res.56=(Phe or Leu); Xaa at res.57=(Ile or Met); Xaa at res.58=(Asn or Lys); Xaa at res.60=(Glu, Asp or Asn); Xaa at res.61=(Thr, Ala or Val); Xaa at res.65=(Pro or Ala); Xaa at res.71=(Gln or Lys); Xaa at res.73=(Asn or Ser); Xaa at res.75=(Ile or Thr); Xaa at res.80=(Phe or Tyr); Xaa at res.82=(Asp or Ser); Xaa at res.84=(Ser or Asn); Xaa at res.89=(Lys or Arg); Xaa at res.91=(Tyr or His); and Xaa at res.97=(Arg or Lys).

In still another preferred embodiment, useful osteogenically active proteins have polypeptide chains with amino acid sequences comprising a sequence encoded by a nucleic acid that hybridizes, under low, medium or high stringency hybridization conditions, to DNA or RNA encoding reference morphogen sequences, e.g., C-terminal sequences defining the conserved seven cysteine domains of OP-1, OP-2, BMP-2, BMP-4, BMP-5, BMP-6, 60A, GDF-3, GDF-6, GDF-7 and the like. As used herein, high stringent hybridization conditions are defined as hybridization according to known techniques in 40% formamide, 5×SSPE, 5× Denhardt's Solution, and 0.1% SDS at 37° C. overnight, and washing in 0.1×SSPE, 0.1% SDS at 50° C. Standard stringent conditions are well characterized in commercially available, standard molecular cloning texts. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984), the disclosures of which are incorporated herein by reference.

As noted above, proteins useful in the present invention generally are dimeric proteins comprising a folded pair of the above polypeptides. Such morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above.

The bone morphogenic proteins useful in the materials and methods of this invention include proteins comprising any of the polypeptide chains described above, whether isolated from naturally-occurring sources, or produced by recombinant DNA or other synthetic techniques, and includes allelic and phylogenetic counterpart variants of these proteins, as well as muteins thereof, and various truncated and fusion constructs. Deletion or addition mutants also are envisioned to be active, including those which may alter the conserved C-terminal six or seven cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Currently preferred host cells include, without limitation, prokaryotes including *E. coli* or eukaryotes including yeast, or mammalian cells, such as CHO, COS or BSC cells. One of ordinary skill in the art will appreciate that other host cells can be used to advantage. Detailed descriptions of the bone morphogenic proteins useful in the practice of this invention, including how to make, use and test them for osteogenic activity, are disclosed in numerous publications, including U.S. Pat. Nos. 5,266,683 and 5,011,691, the disclosures of which are incorporated by reference herein, as well as in any of the publications recited herein, the disclosures of which are incorporated herein by reference.

Thus, in view of this disclosure and the knowledge available in the art, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating endochondral bone morphogenesis in a mammal.

Morphogenic Protein Stimulatory Factors (MPSF)

A morphogenic protein stimulatory factor (MPSF) according to this invention is a factor that is capable of stimulating the ability of a morphogenic protein to induce tissue formation from a progenitor cell. The MPSF may have an additive effect on tissue induction by the morphogenic protein. Preferably, the MPSF has a synergistic effect on tissue induction by the morphogenic protein.

The progenitor cell that is induced to proliferate and/or differentiate by the morphogenic protein of this invention is preferably a mammalian cell. Progenitor cells include mammalian chondroblasts, myoblasts, osteoblasts, neuroblasts and vascular tissue precursor cells, all earlier developmental precursors thereof, and all cells that develop therefrom (e.g., chondroblasts, pre-chondroblasts and chondrocytes). However, morphogenic proteins are highly conserved throughout evolution, and non-mammalian progenitor dells are also likely to be stimulated by same- or cross-species morphogenic proteins and MPSF combinations. It is thus envisioned that when schemes become available for implanting xenogeneic cells into humans without causing adverse immunological reactions, non-mammalian progenitor cells stimulated by morphogenic protein and a MPSF according to the procedures set forth herein will be useful for tissue regeneration and repair in humans.

One or more MPSFs are selected for use in concert with one or more morphogenic proteins according to the desired tissue type to be induced and the site at which the morphogenic protein and MPSF will be administered. The particular choice of a morphogenic protein(s)/MPSF(s) combination and the relative concentrations at which they are combined may be varied systematically to optimize the tissue type induced at a selected treatment site using the procedures described herein.

The preferred morphogenic protein stimulatory factors (MPSFs) of this invention are selected from the group consisting of hormones, cytokines and growth factors. Most preferred MPSFs for inducing bone and/or cartilage formation in concert with an osteogenic protein comprise at least one compound selected from the group consisting of insulin-like growth factor I (IGF-I), estradiol, fibroblast growth factor (FGF), growth hormone (GH), growth and differentiation factor (GDF), hydrocortisone (HC), insulin, progesterone, parathyroid hormone (PTH), vitamin D ($1,25\text{-}(OH)_2D_3$), retinoic acid and an interleukin, particularly IL-6.

In another preferred embodiment of this invention, the MPSF comprises a compound or an agent that is capable of increasing the bioactivity of another MPSF. Agents that increase MPSF bioactivity include, for example, those that increase the synthesis, half-life, reactivity with other biomolecules such as binding proteins and receptors, or the bioavailability of the MPSF. These agents may comprise hormones, growth factors, peptides, cytokines, carrier molecules such as proteins or lipids, or other factors that increase the expression or the stability of the MPSF.

For example, when the selected MPSF is IGF-I, agents that increase its bioactivity include GH, PTH, vitamin D, and cAMP inducers, which may thus function as MPSFs according to this invention. In addition, almost all of the IGF-I in circulation and the extracellular space is bound by a group of high affinity binding proteins called IGFBPs which can augment or inhibit IGF-I bioactivity (see, e.g., Jones and Clemmons, *Endocrine Reviews*, 16, pp. 3-34 (1995)). Thus IGFBPs and agents which alter the levels of IGFBPs such that the bioactive IGF-I concentration is ultimately increased will also function as a MPSF according to this invention.

These or other agents that increase IGF-I bioactivity may be used alone as the primary MPSF, or one or more may be used as additional MPSFs in combination with IGF-I, to stimulate the tissue inductive activity of the morphogenic protein. One such preferred combination comprising at least two MPSFs for cartilage and bone formation is osteogenic protein OP-1, IGF-I and PTH.

Preferably, the MPSF is present in an amount capable of synergistically stimulating the tissue inductive activity of the morphogenic protein in a mammal. The relative concentrations of morphogenic protein and MPSF that will optimally induce tissue formation when administered to a mammal may be determined empirically by the skilled practitioner using the procedures described herein.

Implant Device

The invention also relates to an implant device for promoting bone formation, regeneration and repair. The implant device comprises the porous β-TCP material of the invention, and optionally at least one bioactive agent.

The implant device comprising the porous β-TCP material serves as a temporary scaffold and substratum for recruitment of migratory progenitor cells, and as a base for their subsequent anchoring and proliferation.

In a preferred embodiment, the implant device comprises the porous β-TCP matrix and a bioactive agent, which is dispersed or absorbed in the matrix. It is envisioned that the bioactive agent can include but is not limited to bone morphogenic proteins, growth factors such as EGF, PDGF, IGF, FGF, TGF-α and TGF-β, cytokines, MPSF, hormones, peptides, lipids, trophic agents and therapeutic compositions including antibiotics and chemotherapeutic agents, insulin, chemoattractant, chemotactic factors, enzymes, enzyme inhibitors. It is also envisioned that bioactive agents such as vitamins, cytoskeletal agents, autograft, allograft, cartilage fragments, living cells such as chondrocytes, bone marrow cells, mesenchymal stem cells, tissue transplants, immunosuppressants may be added to the porous β-TCP.

The porous β-TCP matrix provides a sustained delivery or support system for the bioactive agent, which is released over time at the implantation site as the matrix material is slowly absorbed. In a preferred embodiment, the bioactive agent is encapsulated in the biodegradable agent. The resorption of the biodegradable agent and the gradual release of the bioactive agent provides a sustained release system. The dosage and rate of delivery of the bioactive agent may be controlled based on the nature of the porous matrix, the nature of the biodegradable agent and the nature of the binding interaction between the bioactive agent encapsulated in the biodegradable agent, the porous matrix and biodegradable agent. In a preferred embodiment, the bioactive agent is a bone morphogenic protein or a nucleic acid molecule that encodes BMP. In a most preferred embodiment, the BMP is OP-1.

In a preferred embodiment, the bioactive agent is a BMP. In a more preferred embodiment, the BMP is OP-1. The porous β-TCP matrix can protect the BMP and MPSF from non-specific proteolysis, and can accommodate each step of the cellular responses involved in progenitor cell induction during tissue development.

Studies have shown that the methodology for combining matrix and morphogenic proteins plays a role in achieving successful tissue induction. The optimal ratios of morphogenic protein to MPSF for a specific combination and tissue type may be determined empirically by those of skill in the art. Greater amounts may be used for large implants. The procedures used to formulate BMP and MPSF into the matrix are sensitive to the physical and chemical state of both the proteins and the matrix.

In the preferred osteogenic device with porous β-TCP, the osteogenic protein diffuses out of the matrix into the implantation site and permits influx and efflux of cells. The osteogenic protein induces the progenitor cells to differentiate and proliferate. Progenitor cells may migrate into the matrix and differentiated cells can move out of the porous matrix into the implant site. The sequential cellular reactions in the interface of the bone matrix/osteogenic protein implants include: binding of fibrin and fibronectin to implanted matrix, migration and proliferation of mesenchymal cells, differentiation of the progenitor cells into chondroblasts, cartilage formation, cartilage calcification, vascular invasion, bone formation, remodeling, and bone marrow differentiation. The preferred osteogenic device with porous β-TCP material, can be applied to bone formation in various orthopedic, periodontal, and reconstructive procedures.

The implant device may also comprise a binder in an admixture with the bioactive agent and/or porous β-TCP material. The binder is added to form a moldable putty which may be shaped to fit a defect site or to take the form of a new tissue. The moldable putty composition can be held in place by the surrounding tissue or masticated muscle. It is preferred to shape the matrix to span a tissue defect and to take the desired form of the new tissue. In the case of bone repair of a non-union defect, for example, it is desirable to use dimensions that span the non-union. Rat studies show that the new bone is formed essentially having the dimensions of the device implanted. Thus, the material may be used for subcutaneous or intramuscular implants. In bone formation procedures, the material is slowly absorbed by the body and is replaced by bone in the shape of or very nearly the shape of the implant.

Prosthetic Device

It is also contemplated that the porous β-TCP material of the present invention may be used in a prosthetic device. The prosthetic device comprises a surface region that can be implanted adjacent to a target tissue of a mammal, and a composition that is disposed on the surface region. The prosthetic devices will be useful for repairing orthopedic defects, injuries or anomalies in the treated mammal. Preferably, the mammal is a human patient. The prosthetic device may be made from a material comprising metal, ceramic or polymer composite material. Preferred devices comprise a load-bearing core selected from Co—Cr—Mo alloys, titanium alloys and stainless steel. Preferred prosthetic devices are selected from the group consisting of a hip device, a fusion cage and a maxillofacial device.

The composition comprises the porous β-TCP material of the invention, and optionally, one or more agents selected from the group consisting of a bioactive agent or a binder dispersed in the porous β-TCP. In a preferred embodiment, the bioactive agent is encapsulated in the biodegradable agent. In a preferred embodiment, the bioactive agent is a BMP or nucleic acid encoding BMP, more preferably, OP-1. Osteogenic protein-coated prosthetic devices may enhance the bond strength between the prosthesis and existing bone. (Rueger et al., U.S. Pat. No. 5,344,654, incorporated herein by reference). The composition may act as a coating for synthetically constructed bone material, such as for an artificial hip, replacement of diseased bone, correction of defects, or anchoring teeth. The composition is disposed on the surface of the implant in an amount sufficient to promote enhanced tissue growth into the surface. The amount of the composition sufficient to promote enhanced tissue growth may be determined empirically by those of skilled in the art using bioassays described in Rueger et al., U.S. Pat. No. 5,344,654, incorporated herein by reference. Preferably, animal studies are performed to optimize the concentration of the composition components before a similar prosthetic device is used in the human patient.

In another preferred embodiment, the composition is applied to the clinical procedure of total joint arthroplasty in hips, knees, elbows and other joints, wherein a diseased or damaged natural joint is replaced by a prosthetic joint. For example, in a total hip arthroplasty, an acetabular cup is inserted with the composition in the acetabular socket of the pelvis to replace the natural acetabulum. The cup is held in place by the composition and secured by fixation screws. Generally, the cavity or socket conforms to the outer surface of the acetabular cup. The composition can also be applied to total joint revision surgery, to strengthen the bondage between joint prosthetic devices and the bone.

In yet another preferred embodiment, the composition is applied to a clinical procedure called vertebroplasty. The composition is injected into the interior of a vertebral body. This method is used in the treatment of osteoporosis to increase the density of bone.

In a preferred embodiment, the prosthetic device is selected from the group consisting of a fusion cage, a dowel and other devices having a pocket or chamber, such as an interbody fusion for containing the composition of the present invention. Preferably, the interbody fusion device is produced from material selected from the group consisting of titanium, PEEK (poly(etheretherketone)) and allograft. The interbody fusion in the cervical, thoracic and lumbar spine can be administered via an anterior or posterior approach. Alternatively, the composition of this invention can be used without an associated interbody device to achieve interbody fusion.

Spinal fusion cages are placed into the intervertebral space left after the removal of a damaged spinal disc to eliminate local motion and to participate in vertebral to vertebra bony fusion. As described in U.S. Pat. No. 5,015,247, incorporated herein by reference, the fusion cages are in the form of a cylindrical hollow member having an outside diameter larger than the space between two adjacent vertebrae to be fused. The interior space within the cylindrical hollow implant can be filled with the composition of this invention. The cylindrical implants can also include a threaded exterior to permit threaded insertion into a tapped bore formed in the adjacent vertebrae. Alternatively, some fusion implants have been designed to be impacted into the intradiscal space. As described in U.S. Pat. No. 6,146,420, incorporated herein by reference, the fusion device includes opposite end pieces with an integral central element. The central element has a much smaller diameter so that the fusion device forms an annular pocket around the central element. The composition of this invention can be disposed within the annular pocket between the opposite end pieces.

In a preferred embodiment, the prosthetic device is used for repair of osseous and discoligamentous instability. The composition of this invention may be applied to the intervertebral area, resulting in superior fusion and consequently achieving definitive stabilization of a traumatized motor segment via a single dorsal approach. This application may eliminate the need to undergo a second operation for fractures of the thoracolumbar spine, which, at present, is often necessary but involves additional high risks. Also, this method avoids the problems associated with transplantation of autogenous cancellous bone and its associated risk of high morbidity might be avoided. See, e.g., Rueger et al., *Orthopäde,* 27, pp. 72-79 (1998).

In another preferred embodiment, the prosthetic device is a maxillofacial device. Maxillofacial devices are applied externally to correct facial defects resulting from cancer surgery, accidents, congenital deformities. In order to restore the masticatory deficiencies, a patient with marginal bone mass is first treated with the composition of this invention to pack and build up the surgical site. A maxillofacial anchoring and distracting system, as illustrated in U.S. Pat. No. 5,899,940, incorporated herein by reference, can be applied to increase the existing bone quality. Fixation devices, such as a standard threaded bone screw and simple pin point tack or self-locking and threaded bone tack screw device (U.S. Pat. No. 5,971,985, incorporated herein by reference), are used for the retention of tissue grafts and synthetic membranes to the maxillofacial bone graft site. Once the site has healed, a second surgery is performed to insert the appropriate length endosseous dental implant and to restore masticatory function.

The invention also provides a method for promoting in vivo integration of an implantable prosthetic device of this invention into a target tissue of a mammal comprising the steps of a) providing on a surface of the prosthetic device a composition comprising the porous β-TCP material, optionally, at least one bioactive agent or a binder, and b) implanting the device in a mammal at a locus where the target tissue and the surface of the prosthetic device are maintained at least partially in contact for a time sufficient to permit tissue growth between the target tissue and the device.

Method of Inducing Bone Formation and Delivery

The invention also provides a method of inducing bone formation in a mammal. The mammal is preferably a human patient. The method comprises the step of implanting in the defect site of a mammal a composition comprising the porous β-TCP of the invention. In a preferred embodiment, the composition may further comprise a binder and/or a bioactive agent. The defect can be an endochondreal defect, an osteochondral defect or a segmental defect. The method can be applied to other defects which are not limited to, non-union fractures; bone cavities; tumor resection; fresh fractures (distracted or undistracted); cranial, maxillofacial and facial abnormalities, for example, in facial skeletal reconstruction, specifically, orbital floor reconstruction, augmentation of the alveolar ridge or sinus, periodontal defects and tooth extraction socket; cranioplasty, genioplasty, chin augmentation, palate reconstruction, and other large bony reconstructions; vertebroplasty, interbody fusions in the cervical, thoracic and lumbar spine and posteriolateral fusions in the thoracic and lumbar spine; in osteomyelitis for bone regeneration; appendicular fusion, ankle fusion, total hip, knee and joint fusions or arthroplasty; correcting tendon and/or ligamentous tissue defects such as, for example, the anterior, posterior, lateral and medial ligaments of the knee, the patella and achilles tendons, and the like as well as those defects resulting from diseases such as cancer, arthritis, including osteoarthritis, and other bone degenerative disorders such as osteochondritis dessicans. The method may be used in bone augmentation, bone prosthesis, hard tissue implant, bone scaffolding, fixation systems (e.g. screws, sutures, suture anchors, staples, surgical tacks, clips, plates and screws).

The invention also provides a method of delivering a bioactive agent at a site requiring bone formation comprising the step of implanting the porous β-TCP and a bioactive agent at the defect site of a mammal. The method of delivering the bioactive agent may further include a binder. In a preferred embodiment, the bioactive agent is encapsulated in a biodegradable agent. In a preferred embodiment, the bioactive agent belongs to the bone morphogenic protein family. In another preferred embodiment, the bioactive agent is a nucleic acid molecule comprising a sequence encoding a BMP. Preferably, the nucleic acid is trapped in a carrier. In yet another embodiment, the bioactive agent is a bone cell or a cell transfected with nucleic acid encoding BMP. In another preferred embodiment, the delivery of the bioactive agent is sustained release. The biodegradable agent is preferably a biocompatible and non-immunogenic polymer, more preferably, PLGA. The bioactive agent is preferably OP-1. The release rate of the bioactive agent can be controlled by altering the molecular weight of the PLGA. The degradation of PLGA commences when water penetrates the cement matrix to hydrolyze long polymer chains into short water soluble fragments. This results in a reduction in the molecular weight of the PLGA without loss in its physical properties. Gradually, further erosion of the polymer leads to the disruption of the polymer, thereby releasing the bioactive agent. For example, in the case of 10 kD to 30 kD PLGA, the rate of release for OP-1 is one to six weeks.

The invention also describes a method of delivering a bioactive agent at a site requiring cartilage formation comprising implanting at the defect site of a mammal a composition comprising the bioactive agent and biodegradable agent, wherein the bioactive agent is encapsulated in the biodegradable agent. Preferably, the bioactive agent is OP-1 and the biodegradable agent is PLGA.

EXAMPLE 1

Preparation of Tricalcium Phosphate

A slurry of lime (calcium oxide-hydroxide) is prepared and dilute phosphoric acid is added dropwise to the slurry, which is stirred constantly. The molar proportion of calcium oxide to phosphoric acid is 3:2. The product characteristics are evaluated by X-ray diffraction and adjustments are made to the proportions if required. The resultant slurry is harvested by spray drying. If the slurry is harvested by filtration, the dried cake is crushed to a fine powder of amorphous TCP. The particle size of the amorphous TCP is preferably smaller than 10 μm.

EXAMPLE 2

Preparation of β-TCP Granule

The TCP powder was mixed with polystyrene beads (NUNC A/S-Denmark) (0-160 μm beads). The 10% polyvinyl pyrrolidone (PVP) granulating solution was prepared by adding PVP C-30 (Plasdone C-30, ISP technologies lot # TX 60810) in small portions in a beaker or flask of stirring water until the solution was clear. About 37 ml of 10% PVP solution was added to the TCP mixture in 5 ml increments to form a crumbly mass. As illustrated in Table 1, mixtures were prepared with different proportions of pore-forming beads and TCP.

TABLE 1

| bead composition (w/w) | beads (g) | TCP (g) |
| --- | --- | --- |
| 12.5% | 12.5 | 87.5 |
| 25% | 12.5 | 37.5 |
| 37.5% | 18.75 | 31.25 |
| 50% | 23.75 | 23.75 |

The crumbly mass was passed through <500 μm, 500-1000 μm, or 1000-1700 μm sieves under a vibrating motion to produce wet granules having the corresponding particle size ranges. The sieved material was dried under vacuum at 105° C. for 2-3 hours.

The dried granules then underwent a burn off cycle to vaporize/carbonize the pore-forming material and were subsequently sintered at 1150° C. The temperature was raised from 39° C. to 300° C. over an 18 hour period, held at 300° C. for 1 hour, elevated to 700° C. over an 18 hour period, held at 700° C. for 2 hours, and elevated to 1150° C. over a 6 hour period, and held at 1150° C. for 6 hours, and slow cooled to 39° C. over a 6 hour period. After the sintering cycle, the resultant material was confirmed by X-ray diffraction to be porous crystalline β-TCP.

The 37.5% w/w, 500-1000 μm sintered granules were resieved and mixed with the binder, carboxy methylcellulose sodium to form a moldable putty. The putty mixtures were formed with different proportions of β-TCP and CMC. All combinations of β-TCP and CMC produced a putty having appropriate adherence properties, and did not break up in excess water. The cohesiveness of the putty was enhanced as the CMC proportion increased. The β-TCP/CMC 1:0.4 (w/w) putty showed the best characteristics for handling. The rheological properties of the various samples were determined.

EXAMPLE 3

Rat Model Bioassay for Bone Induction

This assay consists of implanting samples in subcutaneous sites in recipient rats under ether anesthesia. Male Long-Evans rats, aged 28-32 days, may be used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day one of the experiment. Implants are removed at varying times thereafter (i.e. 12 days, 18 days). The heterotrophic site allows for the study of bone induction without the possible ambiguities resulting from the use of orthotropic sites.

Bone growth is determined biochemically by calcium content of the implant. Calcium content, is proportional to the amount of bone formed in the implant. Bone formation therefore is calculated by determining the calcium content of the implant in rats and is expressed as "bone forming units," where one bone forming unit represents the amount of protein that is needed for half maximal bone forming activity of the implant. Bone induction exhibited by intact demineralized rat bone matrix is considered to be the maximal bone differentiation activity for comparison purposes in this assay.

Cellular Events During Endochondral Bone Formation

Successful implants exhibit a controlled progression through the stages of protein-induced endochondral bone development, including: (1) transient infiltration by polymorphonuclear leukocytes; (2) mesenchymal cell migration and proliferation; (3) chondrocyte appearance; (4) cartilage matrix formation; (5) cartilage calcification; (6) vascular invasion, appearance of osteoblasts, and formation of new bone; (7) appearance of osteoclasts, bone remodeling and dissolution of the implanted matrix; and (8) hematopoietic bone marrow differentiation in the ossicles. This time course in rats may be accelerated by increasing the amounts of OP-1 added. It is possible that increasing amounts of one or more MPSFs may also accelerate this time course. The shape of the new bone conforms to the shape of the implanted matrix.

Histological Evaluation

Histological sectioning and staining is preferred to determine the extent of osteogenesis in the implants. Implants are fixed in Bouins Solution, embedded in paraffin, and cut into 6-8 μm sections. Staining with toluidine blue or hemotoxylin/eosin demonstrates clearly the ultimate development of endochondral bone. Twelve-day implants are usually sufficient to determine whether the implants contain newly-induced bone.

Biological Markers

Alkaline phosphatase (AP) activity may be used as a marker for osteogenesis. The enzyme activity may be determined spectrophotometrically after homogenization of the implant. The activity peaks at 9-10 days in vivo and thereafter slowly declines. Implants showing no bone development by histology have little or no alkaline phosphatase activity under these assay conditions. The assay is useful for quantification and obtaining an estimate of bone formation quickly after the implants are removed from the rat. Alternatively, the amount of bone formation can be determined by measuring the calcium content of the implant.

Gene expression patterns that correlate with endochondral bone or other types of tissue formation can also be monitored by quantitating mRNA levels using procedures known to those of skill in the art such as Northern Blot analysis. Such developmental gene expression markers may be used to determine progression through tissue differentiation pathways after osteogenic protein/MPSF treatments. These markers include osteoblastic-related matrix proteins such as procollagen $\alpha_2$ (I), procollagen $\alpha_1$ (I), procollagen $\alpha_1$ (III), osteonectin, osteopontin, biglycan, and alkaline phosphatase for bone regeneration (see e.g., Suva et al., *J. Bone Miner. Res.*, 8, pp. 379-88 (1993); Benayahu et al., *J. Cell. Biochem.*, 56, pp. 62-73 (1994)).

EXAMPLE 4

Sheep Model Bioassay for Bone Repair

Skeletally mature female sheep were included in the study. Three drilled defects were created in the area of the proximal metaphysis for both the left and right tibia of each animal. Defects were 6 mm in diameter and at least 10 mm deep. The defect size was consistent across all test animals. The defects were created so as to maintain the structure of the interosseous fibrofatty marrow. This marrow acts as a barrier between the implant materials and prevents interosseous mixing of the matrix materials tested. As illustrated in Table 2, β-TCP putty I, II, III, IV and collagen were tested in the defect sites with and without OP-1. OP-1 was either directly added to the β-TCP formulations or encapsulated in PLGA. Table 3 represents examples of formulations wherein the OP-1 is encapsulated in PLGA. Of the six defect sites in each animal, one defect site served as a control, which contained no test material.

A 3 to 4 inch incision was made over the proximal tibial metaphysis. The skin and underlying muscle were dissected to expose the periosteum. The periosteum was incised and maintained intact for surgical closure if possible. Three transverse holes were created in the metaphysis. The first and most superior was created approximately 2 cm below the articular surface of the tibia. The defects were created so as to form a line oriented with the long axis of the bone. Implants were spaced at 1.6 cm intervals measured center-to-center.

Materials were harvested at four and eight weeks posttreatment. Animals were euthanised with pentobarbital 75-100 mg/kg IV. The proximal tibia were taken and cut to best allow for tissue fixation. Specimens were fixed in 10% neutral buffered Formalin. Specimens were cut, if feasible, so as to capture all implant sites in a single specimen. Following fixation, specimens were decalcified, embedded in plastic and sectioned in longitudinal orientation using Exackt technique and ground to appropriate section thickness for histologic interpretation.

Radiographic assessment (FIGS. 9-16, 27 and 28) and histologic evaluation (FIGS. 1-8) were made at post-operative, four and eight weeks on all implant sites. Anterior posterior radiographs were taken so as to best image all three defects simultaneously and view the cylindrical defects from the side. Qualitative histologic descriptions identified new bone formation, residual implant material and any evidence of pathologic response. Images were captured for each specimen and scores presented for bone formation, acute and chronic inflammation and residual matrix.

Specimen handling and hemostatic properties were recorded at the time of implantation. Materials ranged in form and consistency from a putty or granular form to a semi-solid cylinder.

TABLE 2

| Code | Formulation | Initial pore-former percentage/Granule size |
|---|---|---|
| 89A | β-TCP Putty I | 12.5% (w/w), 0.5-1 mm |
| 89B | β-TCP Putty II | 25% (w/w), 0.5-1 mm |
| 89C | β-TCP Putty III | 37.5% (w/w), 0.5-1 mm |
| 89F | β-TCP Putty IV | 25% (w/w), 1-2 mm |
| 48C | Collagen | Bovine type I collagen |
| SOB1 | Lyophil 1 | OP-1 |
| SOP2 | Lyophil 2 | Placebo |
|  | Reconstitution | Resconstitution medium |

TABLE 3

| Code | Formulation |
|---|---|
| formulation 4 | β-TCP, 7% (w/w) PLGA (10 kD) with 0.3% (w/w) OP-1 |
| formulation 5 | β-TCP, 7% (w/w) PLGA (25-30 kD) with 0.3% (w/w) OP-1 |

Formulation Handling

Lyophil 1 and Lyophil 2 (placebo) were reconstituted by adding 2.5 ml of the reconstitution medium to one vial of the Lyophil (All components were stored frozen at 2 to 8° C. until use), shaking the medium gently for 2 minutes until a homogenous (clear to cloudy) gel was formed. 0.4 ml of reconstituted Lyophil gel was added to the porous β-TCP matrix slowly and with care. Utilizing a thin spatula, the porous β-TCP matrix was mixed with the gel to form a putty-like material.

The PLGA microspheres (particle size 75-150 μm, Alkermes, Inc.) encapsulated with 0.3% (w/w) OP-1 were mixed with the porous β-TCP matrix.

The putty material was immediately implanted. The implant materials were placed through the use of a folded piece of sterile paper. The paper was filled with test material and used to pour it into the defect while continuously packing material in the site. The handling properties prior to placement and in the defect site were recorded.

The β-TCP Putty I, II, III, IV formulations were poured as a granular dry powder. Once combined with the vehicle solution, the putties had a dry crunchy granular texture. The formulations absorbed all of the Lyophil solution. The formulation was implanted with a spatula. Once in the implant site, the materials became well filled with blood.

The collagen formulation poured as a fluffy powder. Once mixed with a vehicle solution, it had a gritty putty texture. The formulation could be easily placed with a syringe in the implant site. The implant site became well filled with blood.

Histologic Results

Proximal tibia sections contained three defects. These defects were gross macro-cut so that all three were contained in a single section. Based on gross section observations, clinical assays, and faxitron x-rays of this section, the section was considered representative of the sample. This orientation allowed the evaluation of the periosteal reaction overlying the defects and intramedullary response to the test materials. Specimens were evaluated from 4 and 8 week explants (FIGS. 1-8). All three defects within a single tibial section received either the placebo or OP-1 solution. This segregation of the placebo and OP-1 implants facilitated the determination of the active or inactive biologic nature of the implant material.

Four-Week Evaluation for OP-1 and Placebo Implant Materials

Figure 2:
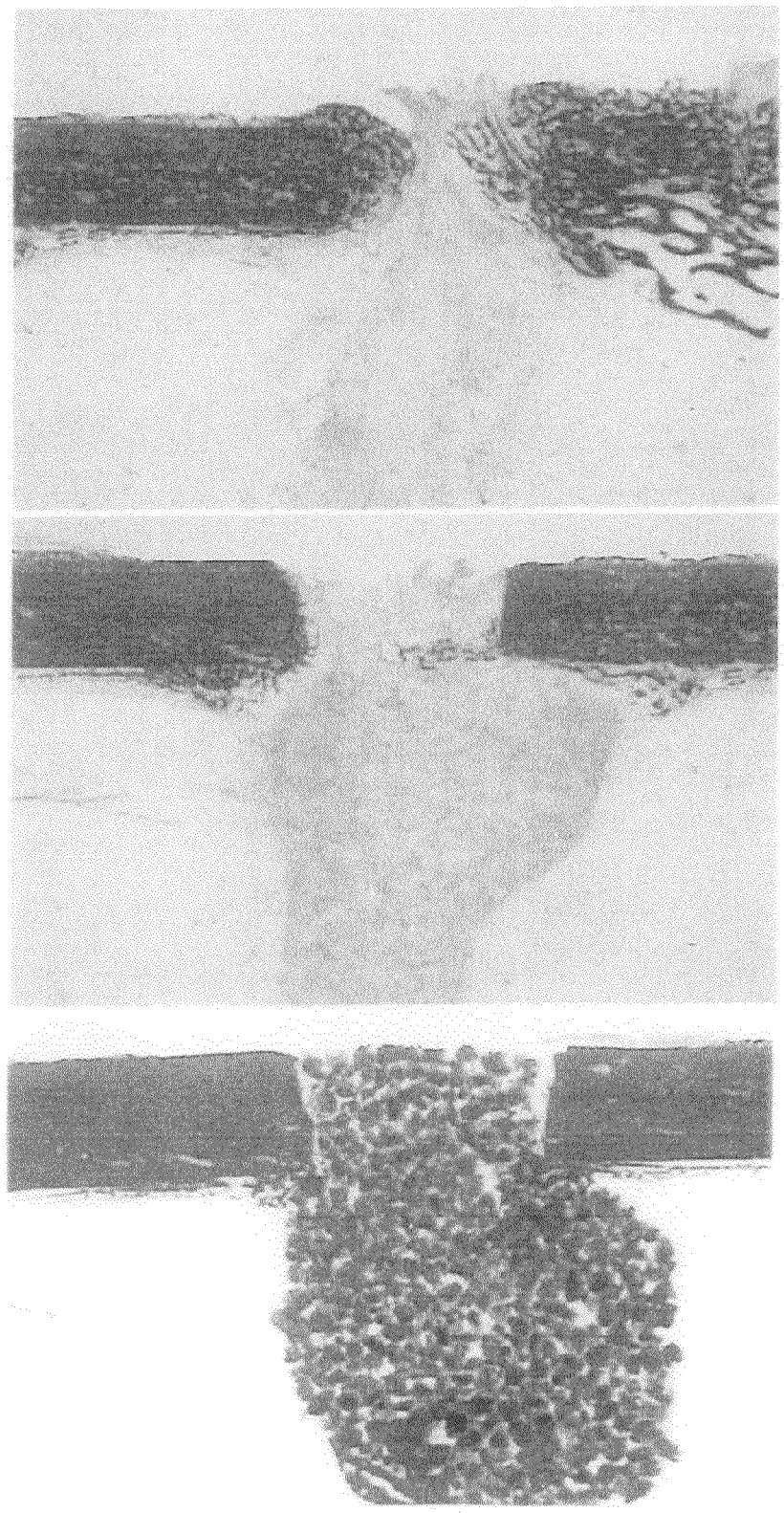
FIG. 2. Histologic image of animal number 297R (right tibia) at 4 weeks with placebo. From top to bottom, the sites are proximal, middle and distal, each containing control, collagen 48C, β-TCP putty 89A, respectively.
Figure 3:
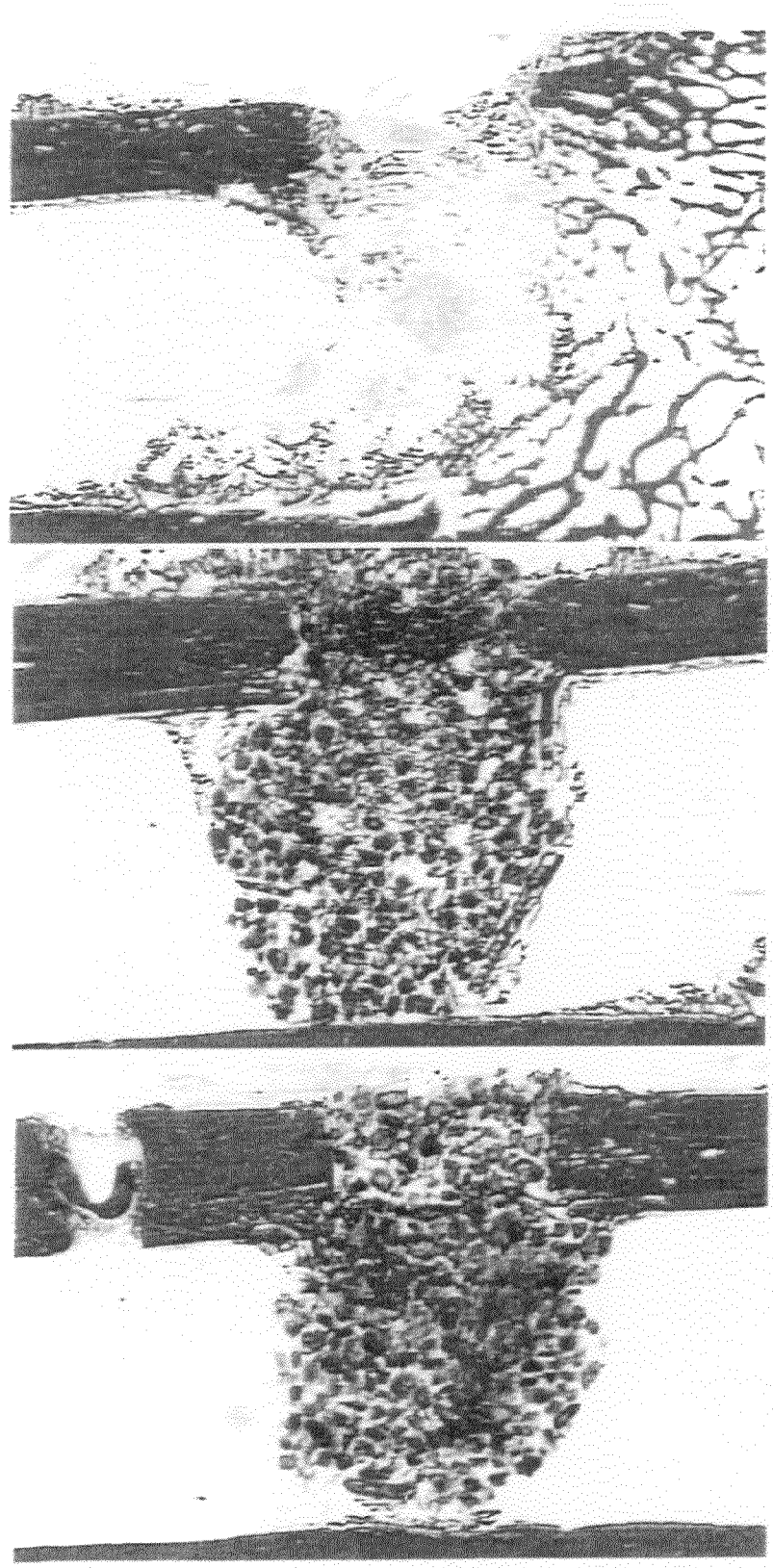
FIG. 3. Histologic image of animal number 295L (left tibia) at 4 weeks with OP-1. From top to bottom, the sites are proximal, middle and distal, each containing collagen 48C, β-TCP putty 89A, β-TCP putty 89B, respectively.

At four weeks, the β-TCP Putty I (89A) was present in all sites (FIG. 3 middle site and FIG. 2 distal site). Generally, the matrix was not significantly resorbed nor was it undergoing active resorption. Sites treated with OP-1 resulted in some but not marked new bone formation (FIG. 3 middle site). Placebo treated sites had bone formation at the level of the cortex (FIG. 2 distal site).

Figure 4:
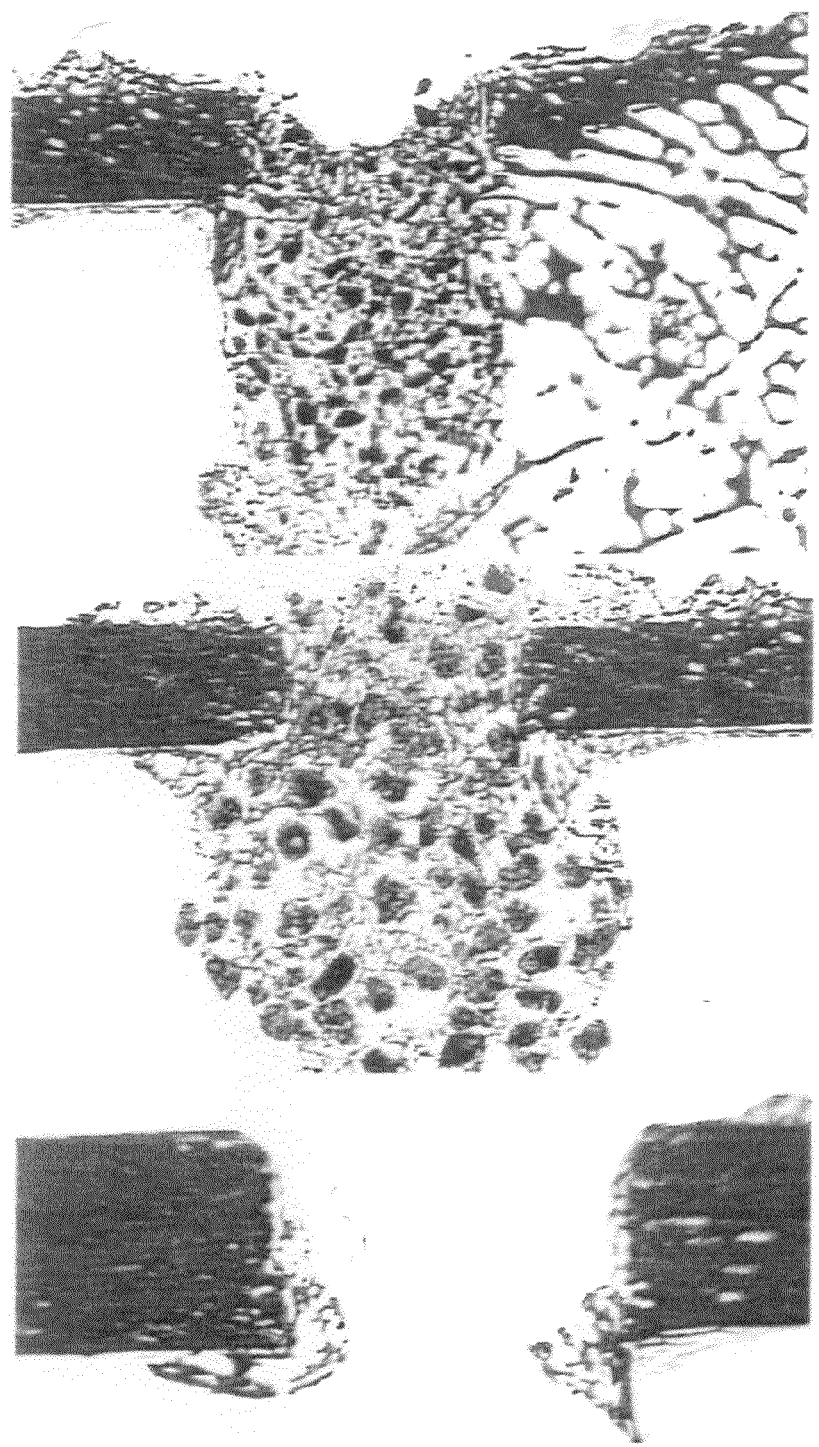
FIG. 4. Histologic image of animal number 295R (right tibia) at 4 weeks with OP-1. From top to bottom, the sites are proximal, middle and distal, each containing β-TCP putty 89C, β-TCP putty 89F, control, respectively.

The β-TCP Putty II (89B) was present in all sites at 4 weeks in significant amounts (FIG. 3 distal site and FIG. 1 proximal site). There was no significant evidence of matrix resorption. OP-1 treated sites resulted in small amounts of new bone formation predominately at the cortical and periosteal level (FIG. 3 distal site). Of the four β-TCP putty formulations tested, β-TCP putty II resulted in more inflammation than the other three formulations. Foreign body giant cells (FBGC) were reported in conjunction with this inflammation.

β-TCP Putty III (89C) was present in significant amounts in all six sites treated at 4 weeks (FIG. 1 middle site and FIG. 4 proximal site). OP-1 treatment did not noticeably alter residual matrix volumes. Bone formation at the cortical level was apparent in OP-1 treated specimens (FIG. 4 proximal site) and less common in placebo treated sites (FIG. 1 middle site). Little or no inflammation was observed in response to the β-TCP matrix independent of OP-1 treatment.

β-TCP Putty IV (89F) was present in significant amounts in all six sites treated at 4 weeks (FIG. 1 distal site and FIG. 4 middle site). OP-1 treatment had no apparent effect on residual matrix volume. OP-1 treated sites resulted in greater bone formation throughout the matrix with cortical and periosteal responses apparent (FIG. 4 middle site). Little or no inflammation was observed in response to the β-TCP matrix independent of OP-1 treatment.

Eight-Week Evaluation for OP-1 and Placebo Treated Implant Materials

Figure 6:
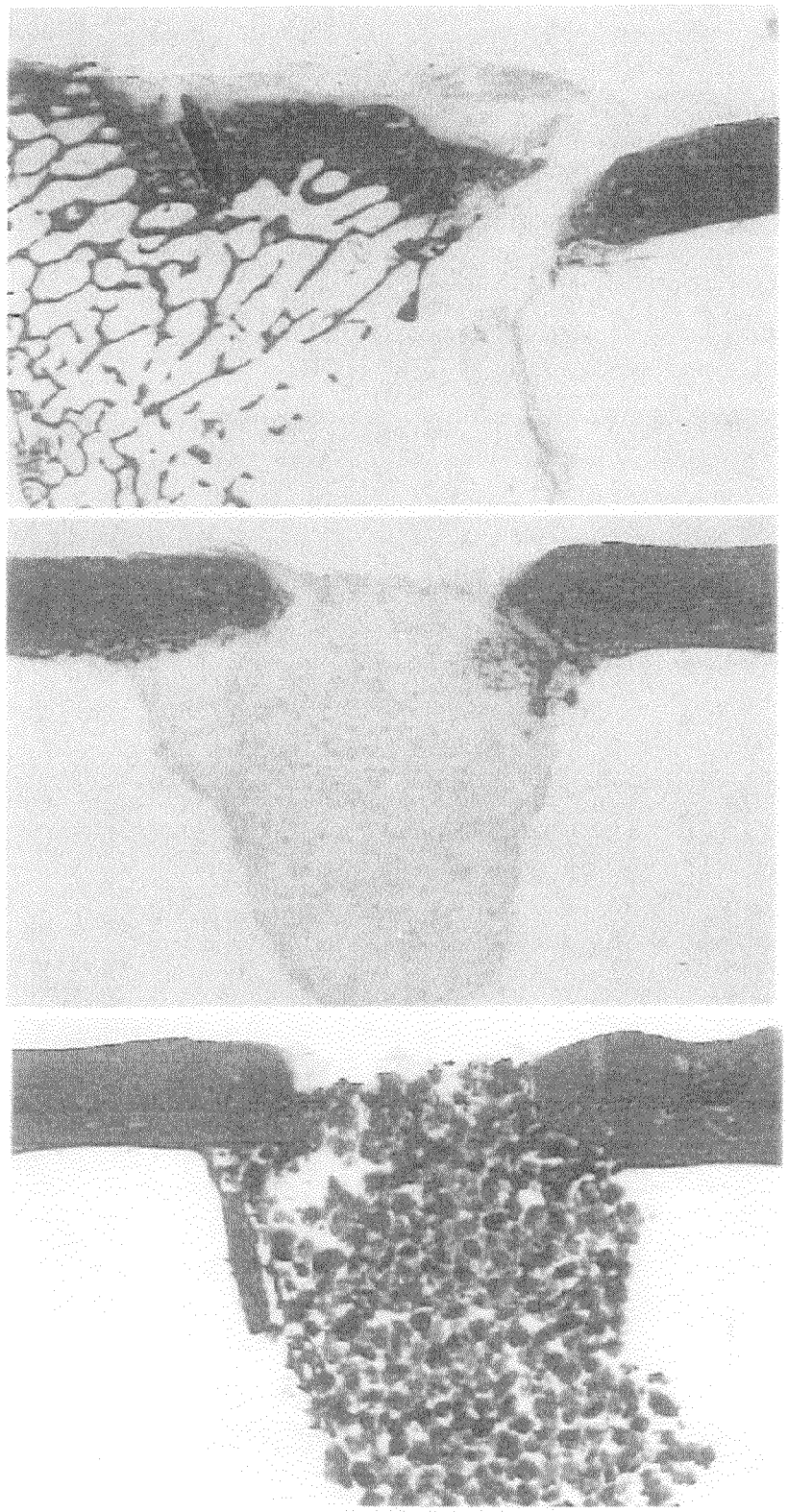
FIG. 6. Histologic image of animal number 299R (right tibia) at 8 weeks with placebo. From top to bottom, the sites are proximal, middle and distal, each containing control, collagen 48C, β-TCP putty 89A, respectively.
Figure 7:
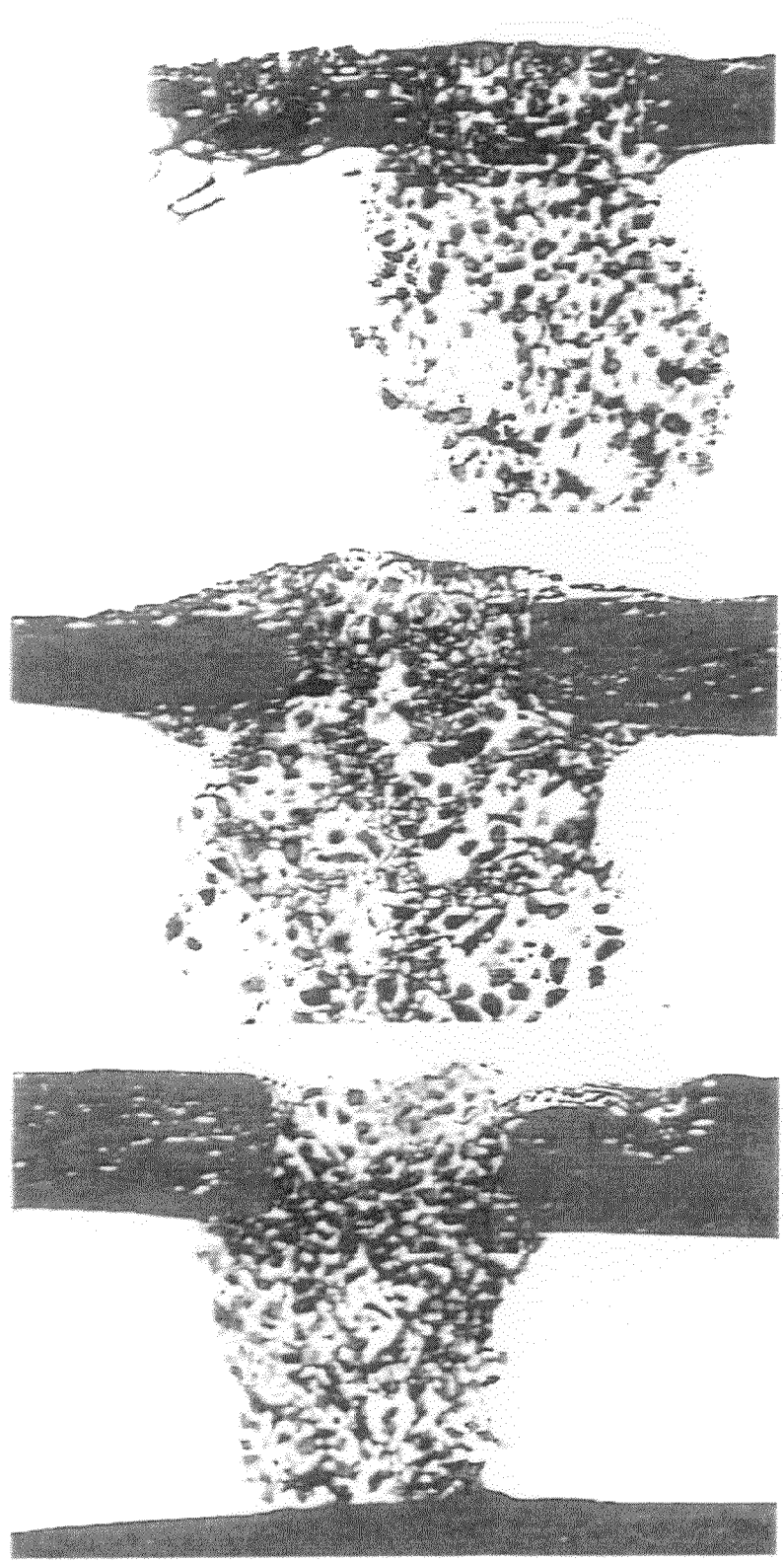
FIG. 7. Histologic image of animal number 138L (left tibia) at 8 weeks with OP-1. From the top, the sites are proximal, middle and distal, each containing β-TCP putty 89A, β-TCP putty 89B, β-TCP putty 89C, respectively.

The β-TCP Putty I (89A) was present in all sites at 8 weeks (FIG. 7 proximal site and FIG. 6 distal site). The OP-1 treated implants generally showed evidence of a strong bone inductive response (FIG. 7 proximal site). In two OP-1 treated sites, the β-TCP matrix appeared to have significantly degraded. Sites treated with OP-1 resulted in marked new bone formation at the cortical level with modest bone infiltration into the matrix within the medullary space. Placebo treated sites resulted in less bone formation at the level of the cortex (FIG. 6 distal site).

Figure 5:
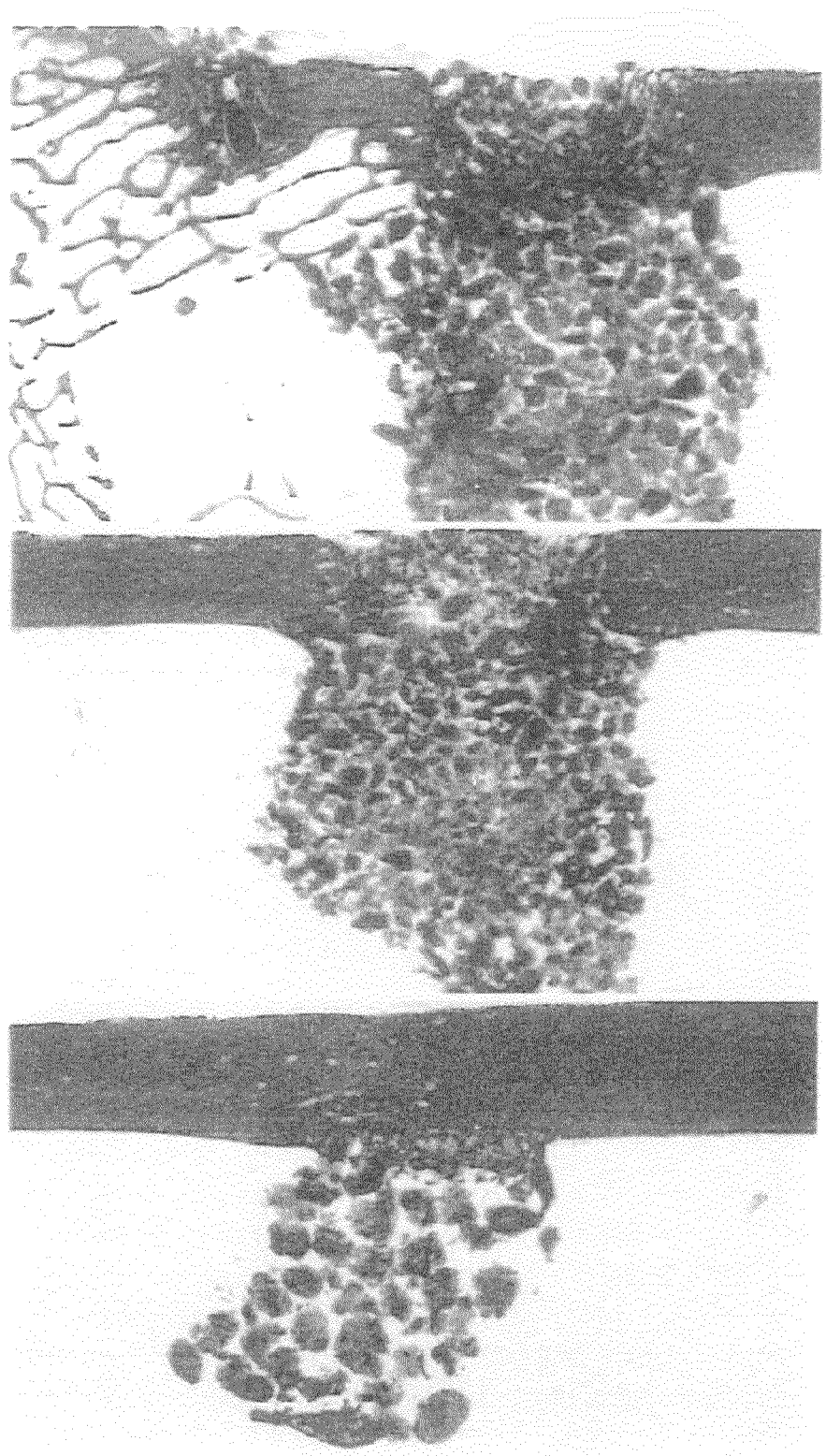
FIG. 5. Histologic image of animal number 299L (left tibia) at 8 weeks with placebo. From top to bottom, the sites are proximal, middle and distal, each containing β-TCP putty 89B, β-TCP putty 89C, β-TCP putty 89F, respectively.
Figure 8:
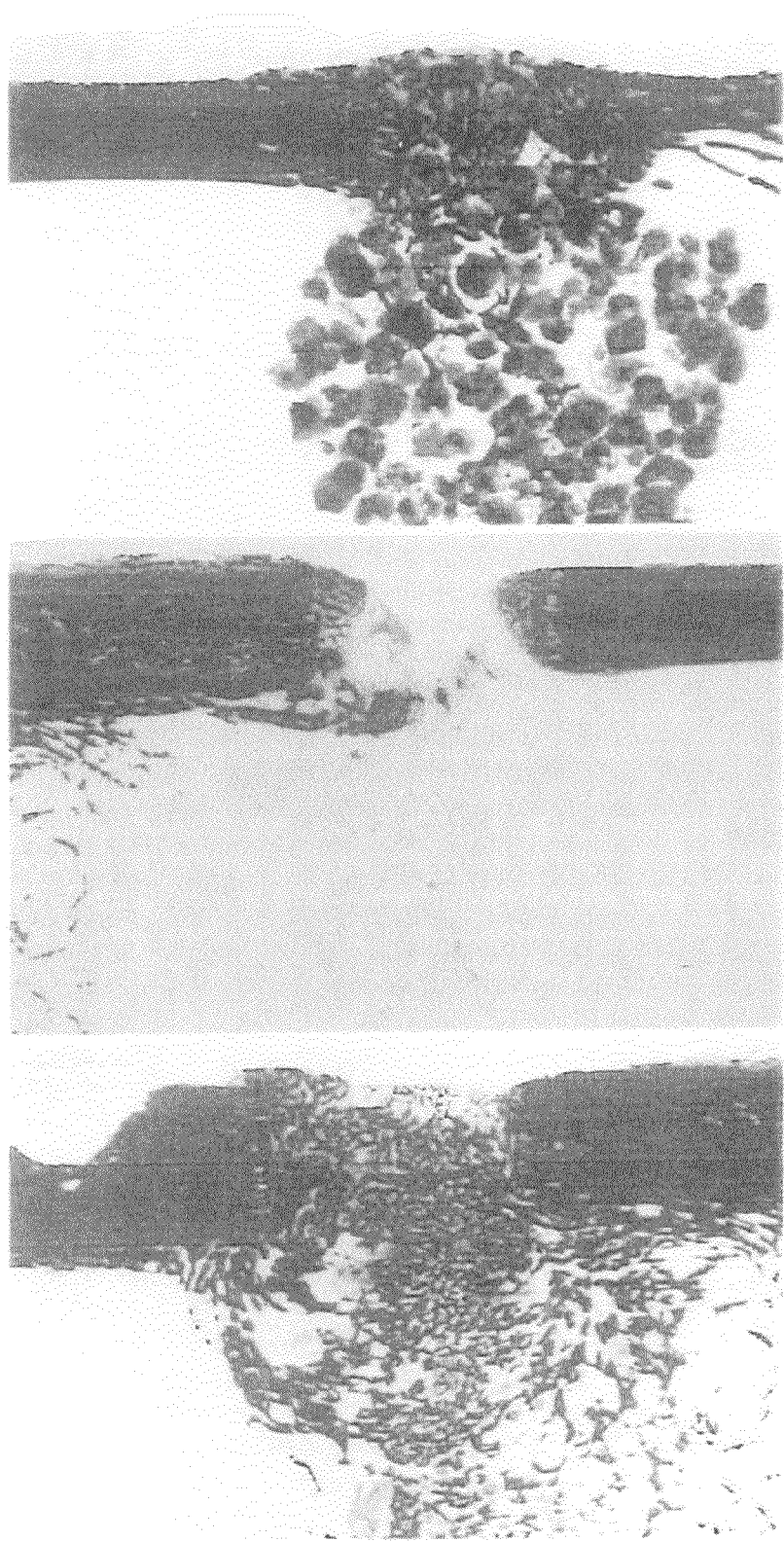
FIG. 8. Histologic image of animal number 138R (right tibia) at 8 weeks with OP-1. From the top, the sites are proximal, middle and distal, each containing β-TCP putty 89F, control, collagen 48C, respectively.
Figure 9:
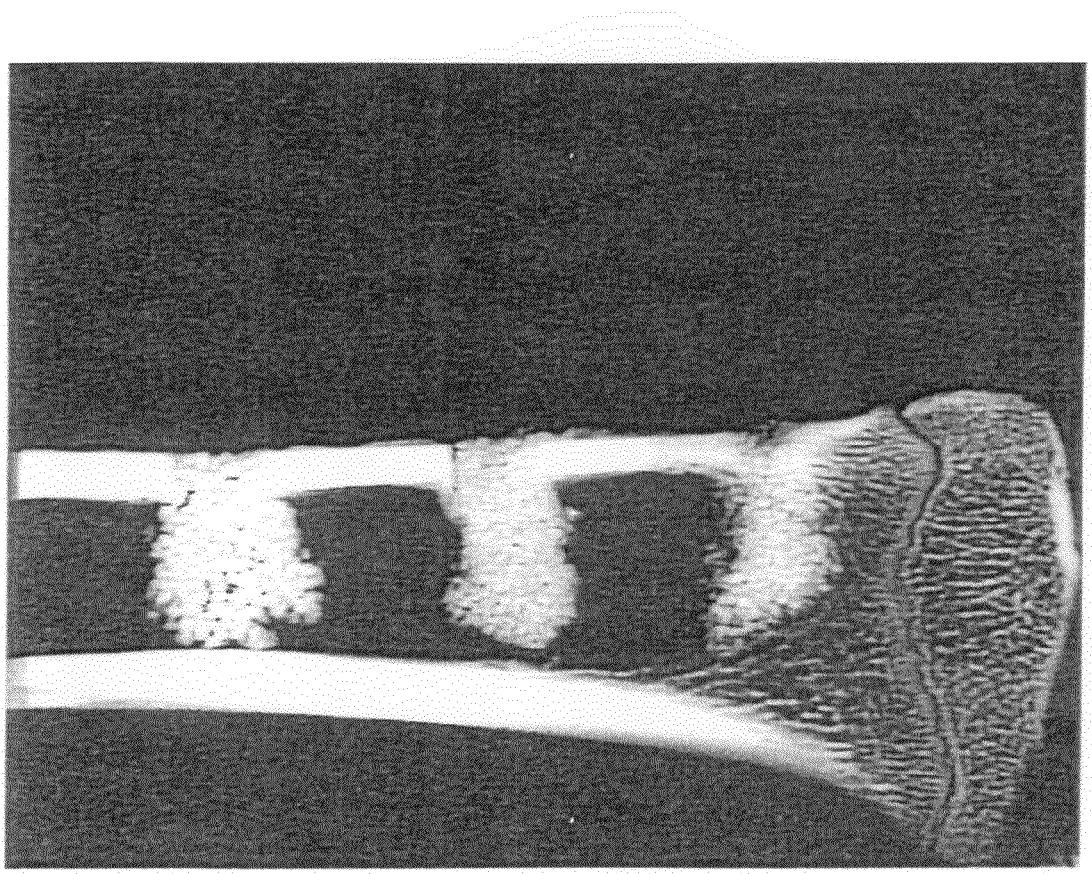
FIG. 9. Radiographic image of animal number 297L (left tibia) at 4 weeks with placebo. From the right, the sites are proximal, middle and distal, each containing β-TCP putty 89B, β-TCP putty 89C, β-TCP putty 89F, respectively.
Figure 10:
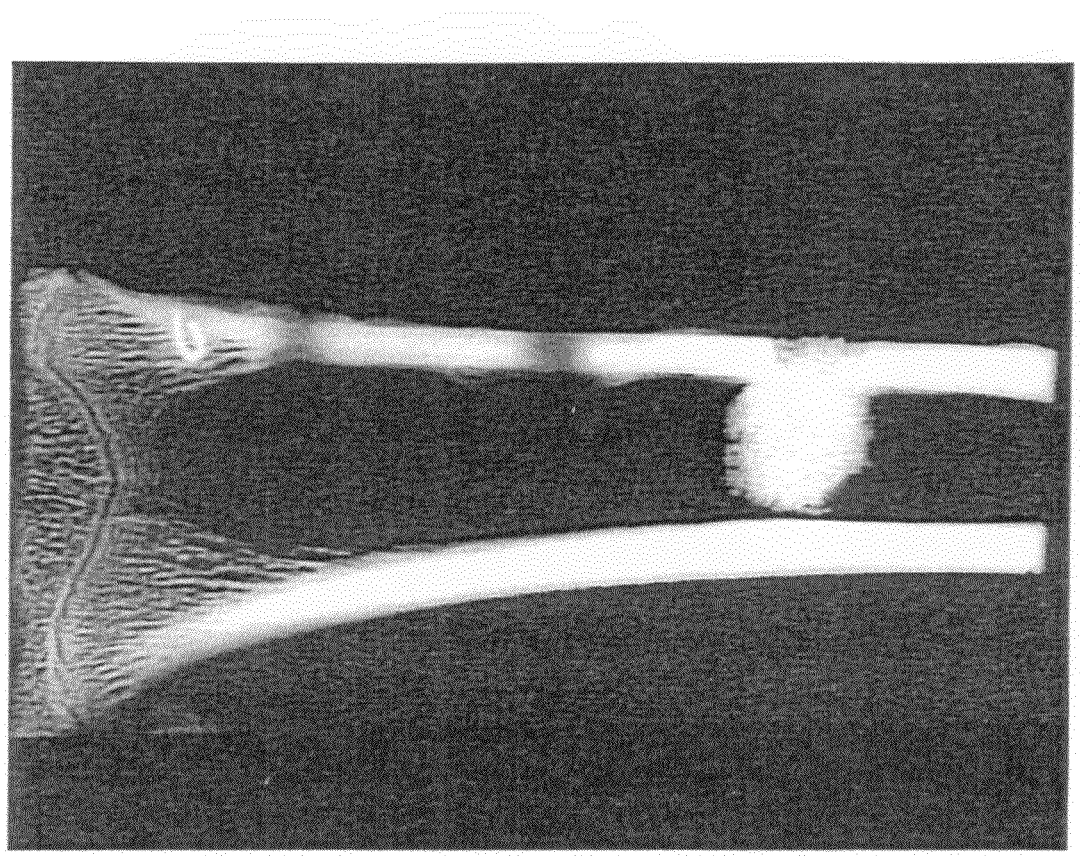
FIG. 10. Radiographic image of animal number 297R (right tibia) at 4 weeks with placebo. From the left, the sites are proximal, middle and distal, each containing control, collagen 48C, β-TCP putty 89A, respectively.
Figure 11:
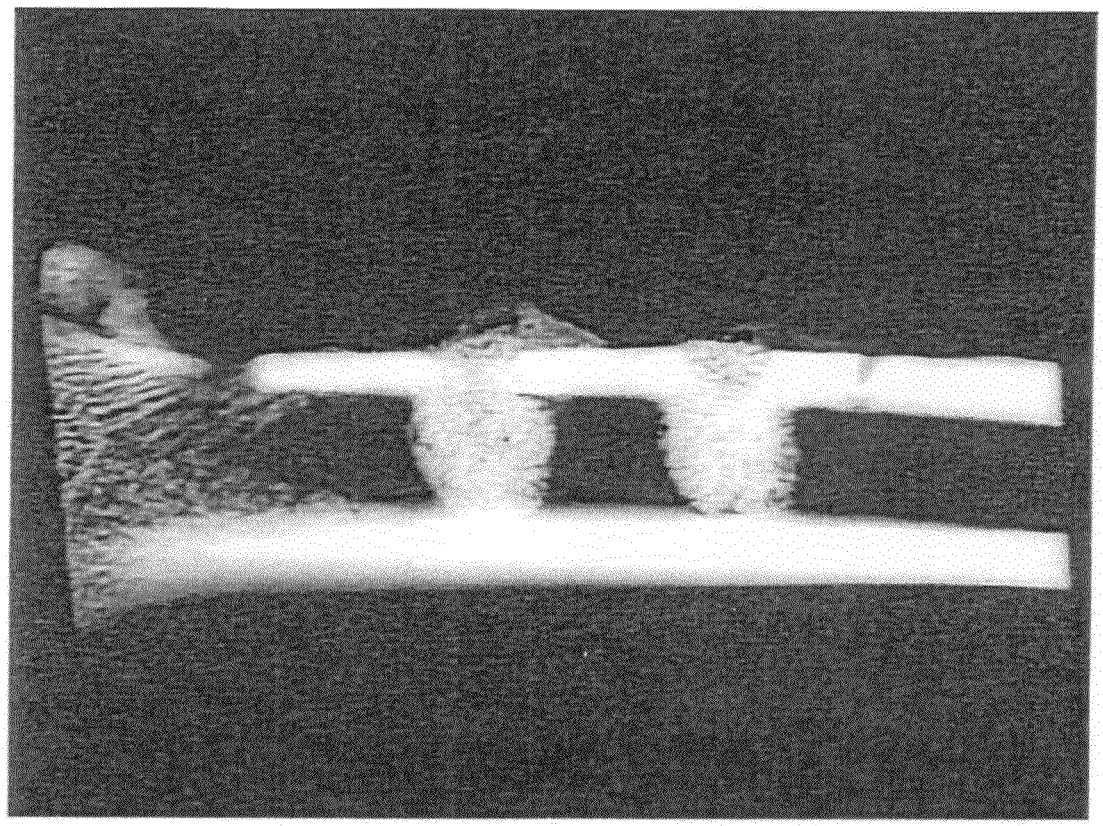
FIG. 11. Radiographic image of animal number 295L (left tibia) at 4 weeks with OP-1. From the left, the sites are proximal, middle and distal, each containing collagen 48C, β-TCP putty 89A, β-TCP putty 89B, respectively.
Figure 12:
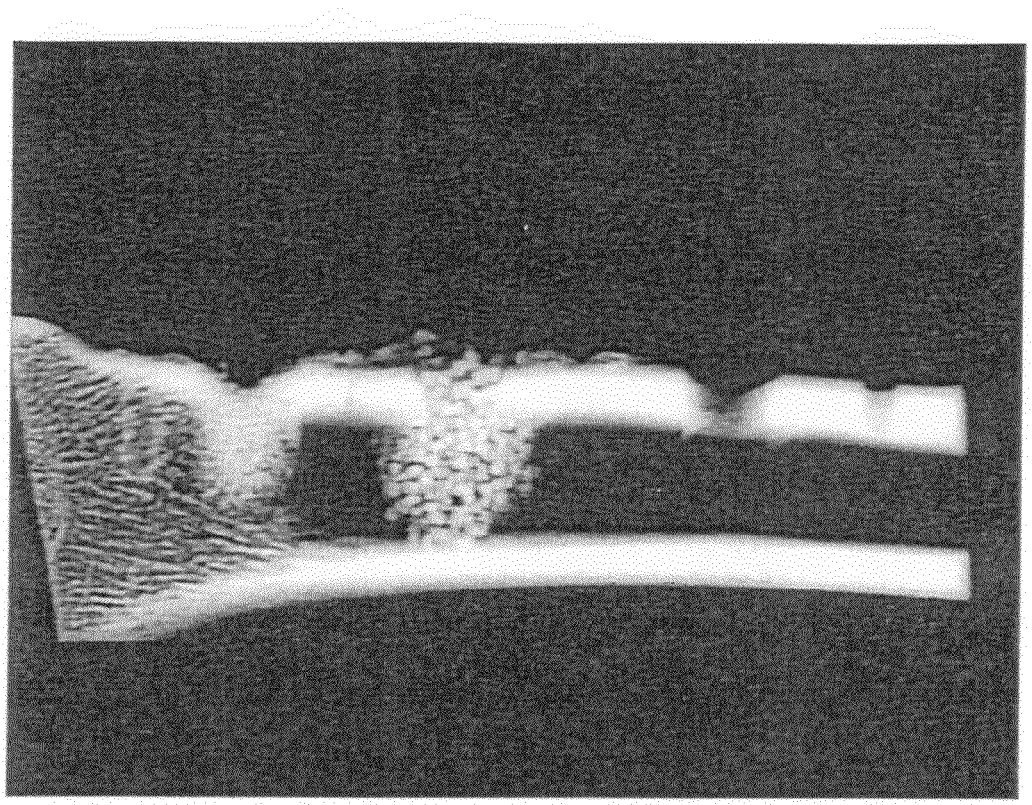
FIG. 12. Radiographic image of animal number 295R (right tibia) at 4 weeks with OP-1. From the left, the sites are proximal, middle and distal, each containing β-TCP putty 89C, β-TCP putty 89F, control, respectively.
Figure 13:
FIG. 13. Radiographic image of animal number 299L (left tibia) at 8 weeks with placebo. From the right, the sites are proximal, middle and distal, each containing β-TCP putty 89B, β-TCP putty 89C, β-TCP putty 89F, respectively.
Figure 14:
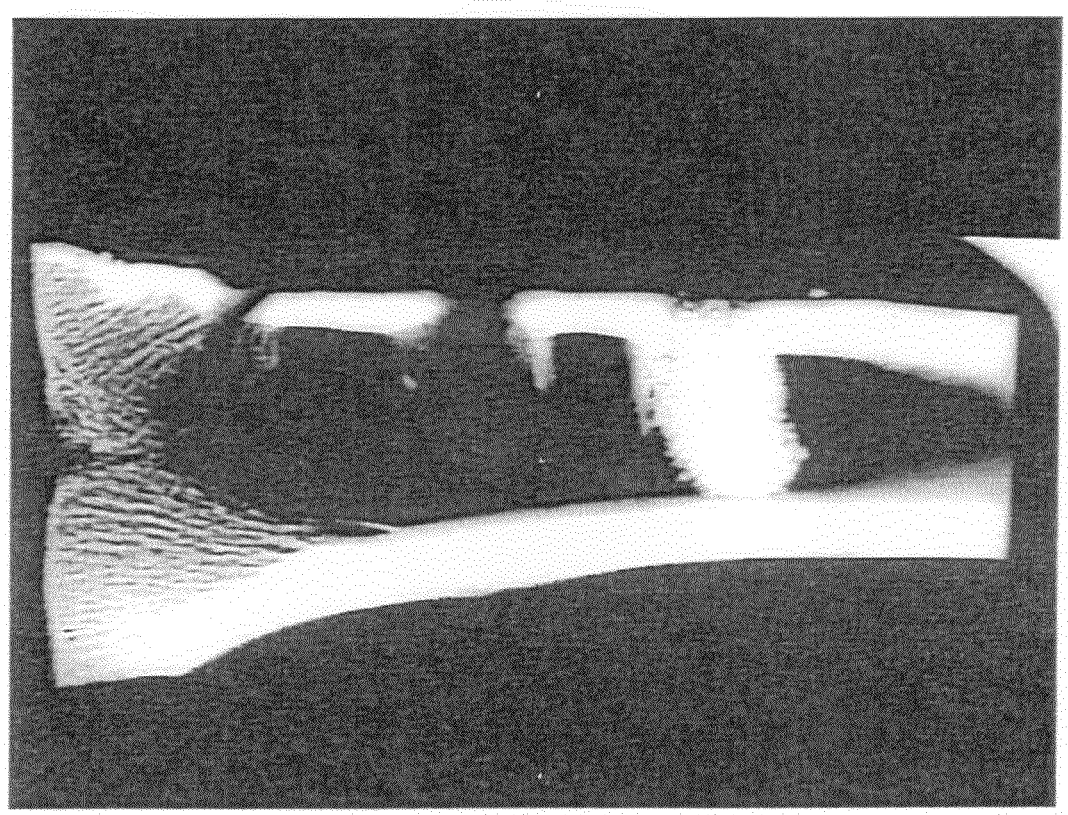
FIG. 14. Radiographic image of animal number 299R (right tibia) at 8 weeks with placebo. From the left, the sites are proximal, middle and distal, each containing control, collagen 48C, β-TCP putty 89A, respectively.
Figure 15:
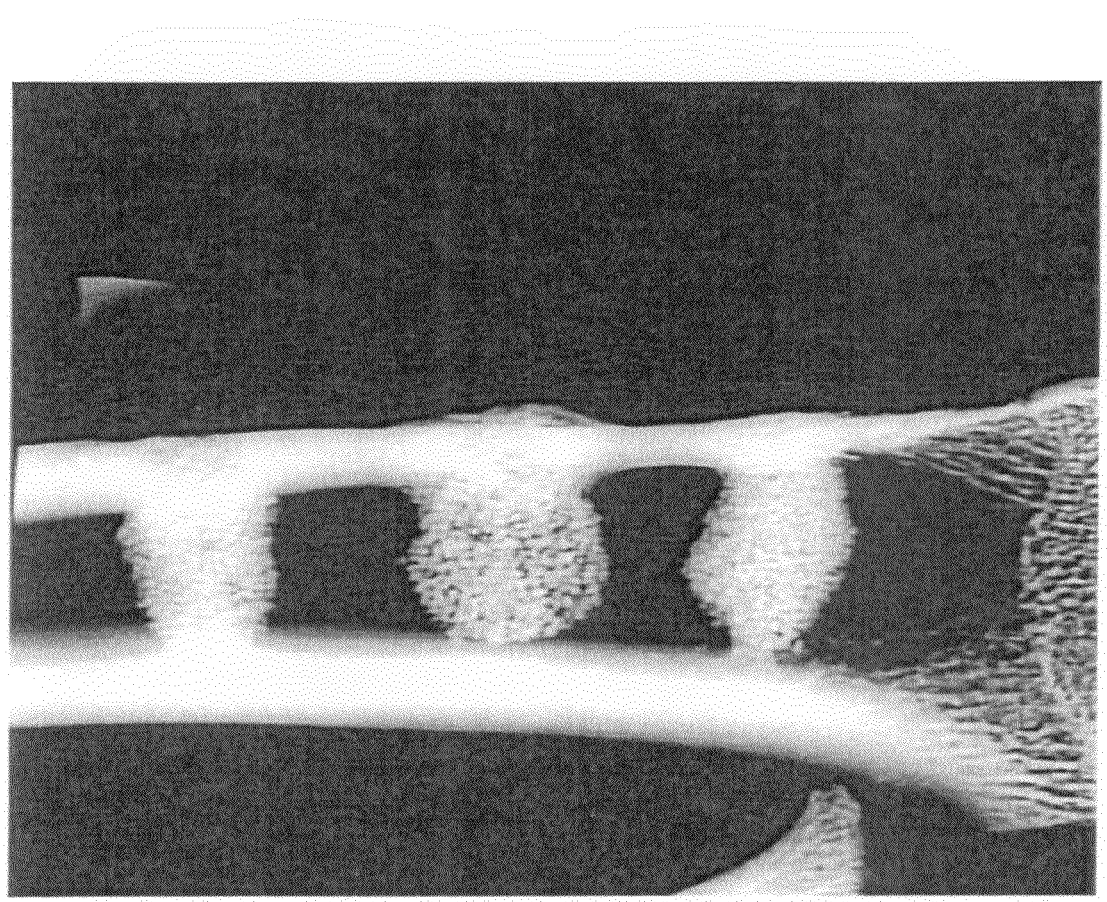
FIG. 15. Radiographic image of animal number 138L (left tibia) at 8 weeks with OP-1. From the right, the sites are proximal, middle and distal, each containing β-TCP putty 89A, β-TCP putty 89B, β-TCP putty 89C, respectively.
Figure 16:
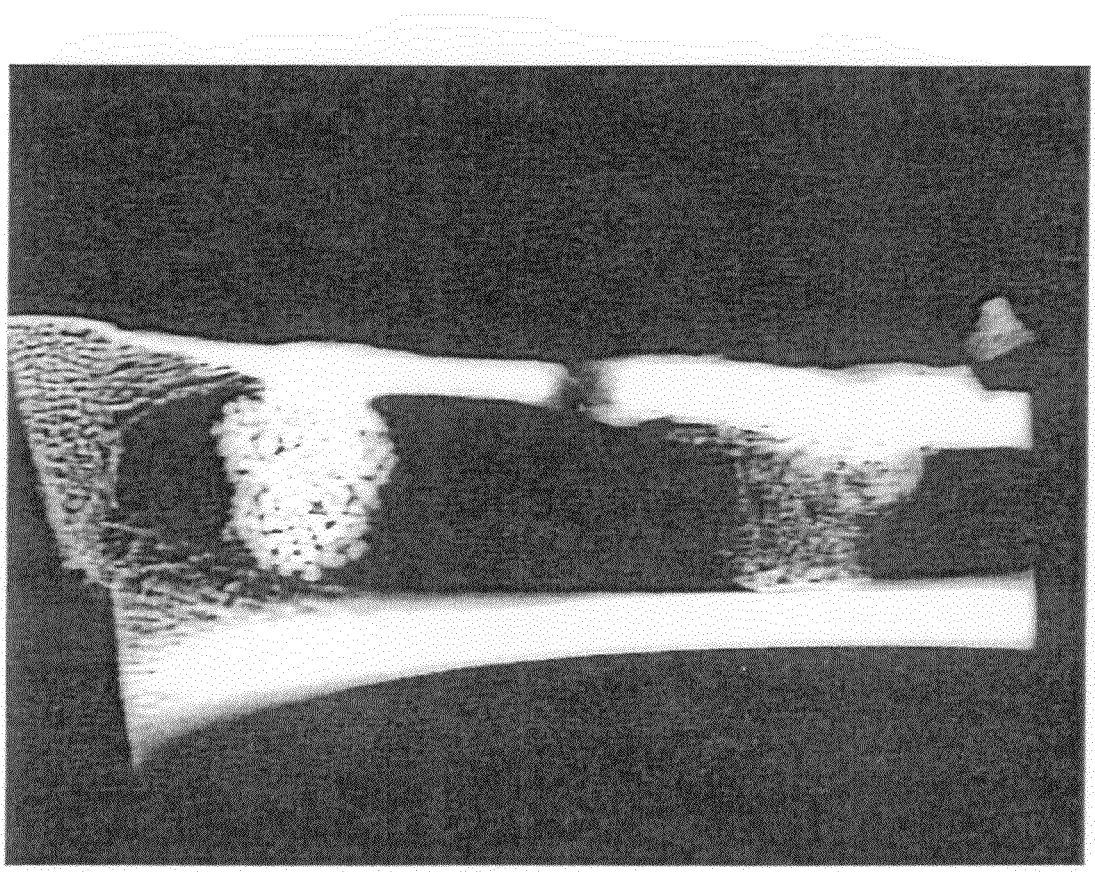
FIG. 16. Radiographic image of animal number 138R (right tibia) at 8 weeks with OP-1. From the left, the sites are proximal, middle and distal, each containing β-TCP putty 89F, control, collagen 48C, respectively.
Figure 17:
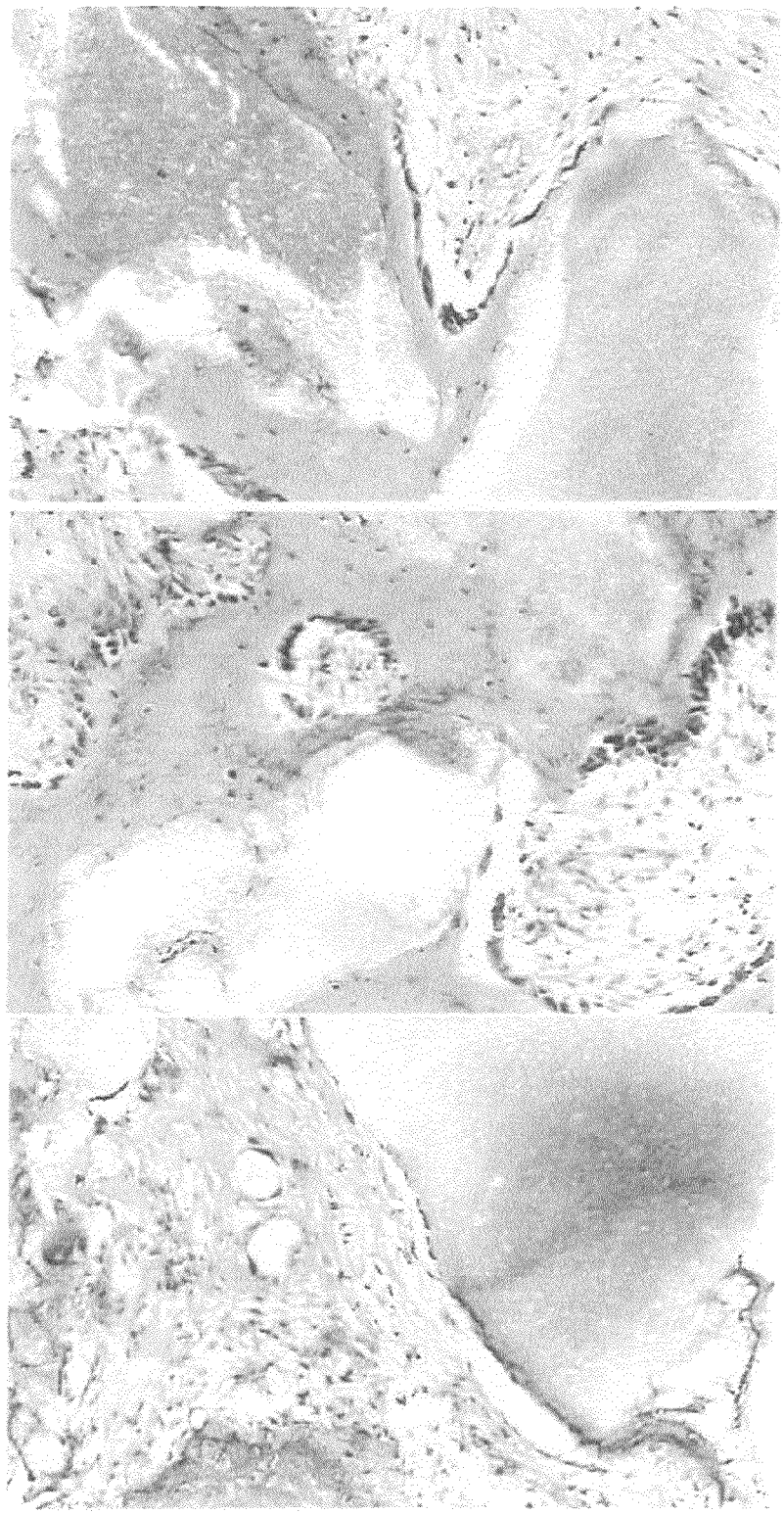
FIG. 17. Paraffin scanning image of animal number 297L (left tibia) at 4 weeks with placebo. From the top, the sites are proximal, middle and distal, each containing β-TCP putty 89B, β-TCP putty 89C, β-TCP putty 89F, respectively.
Figure 18:
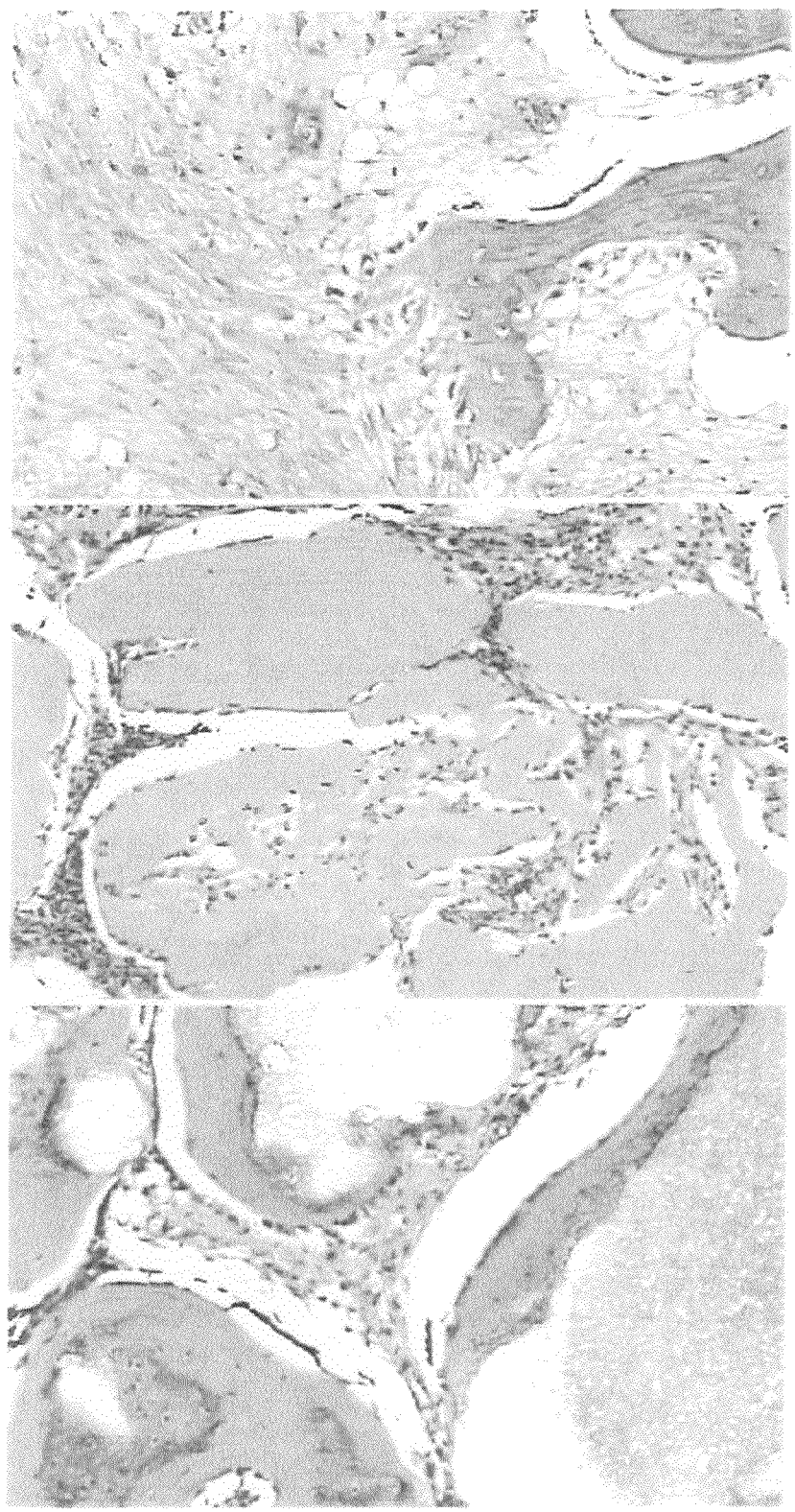
FIG. 18. Paraffin scanning image of animal number 297R (right tibia) at 4 weeks with placebo. From the top, the sites are proximal, middle and distal, each containing control, collagen 48C, β-TCP putty 89A, respectively.
Figure 19:
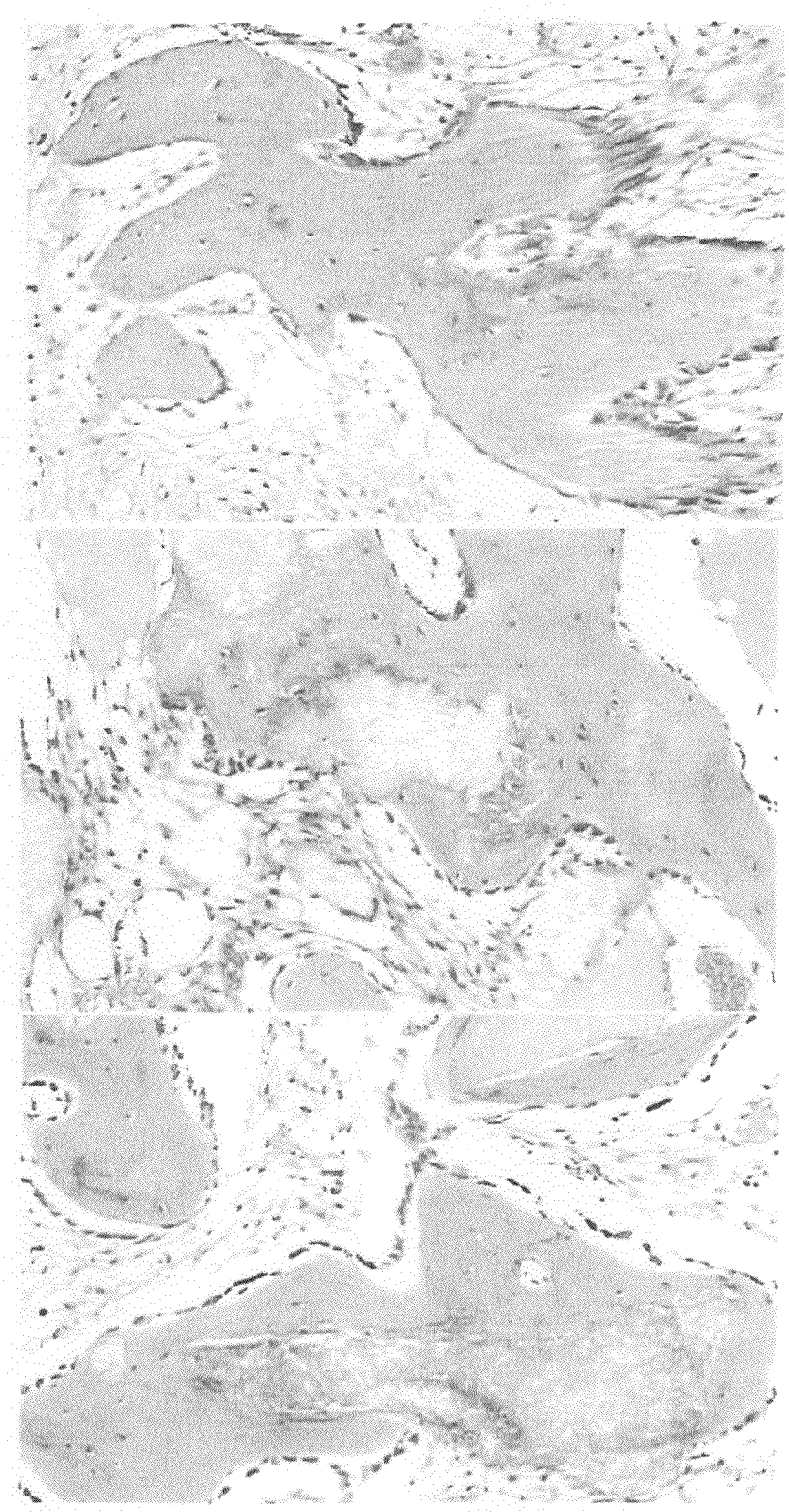
FIG. 19. Paraffin scanning image of animal number 295L (left tibia) at 4 weeks with OP-1. From the top, the sites are proximal, middle and distal, each containing collagen 48C, β-TCP putty 89A, β-TCP putty 89B, respectively.
Figure 20:
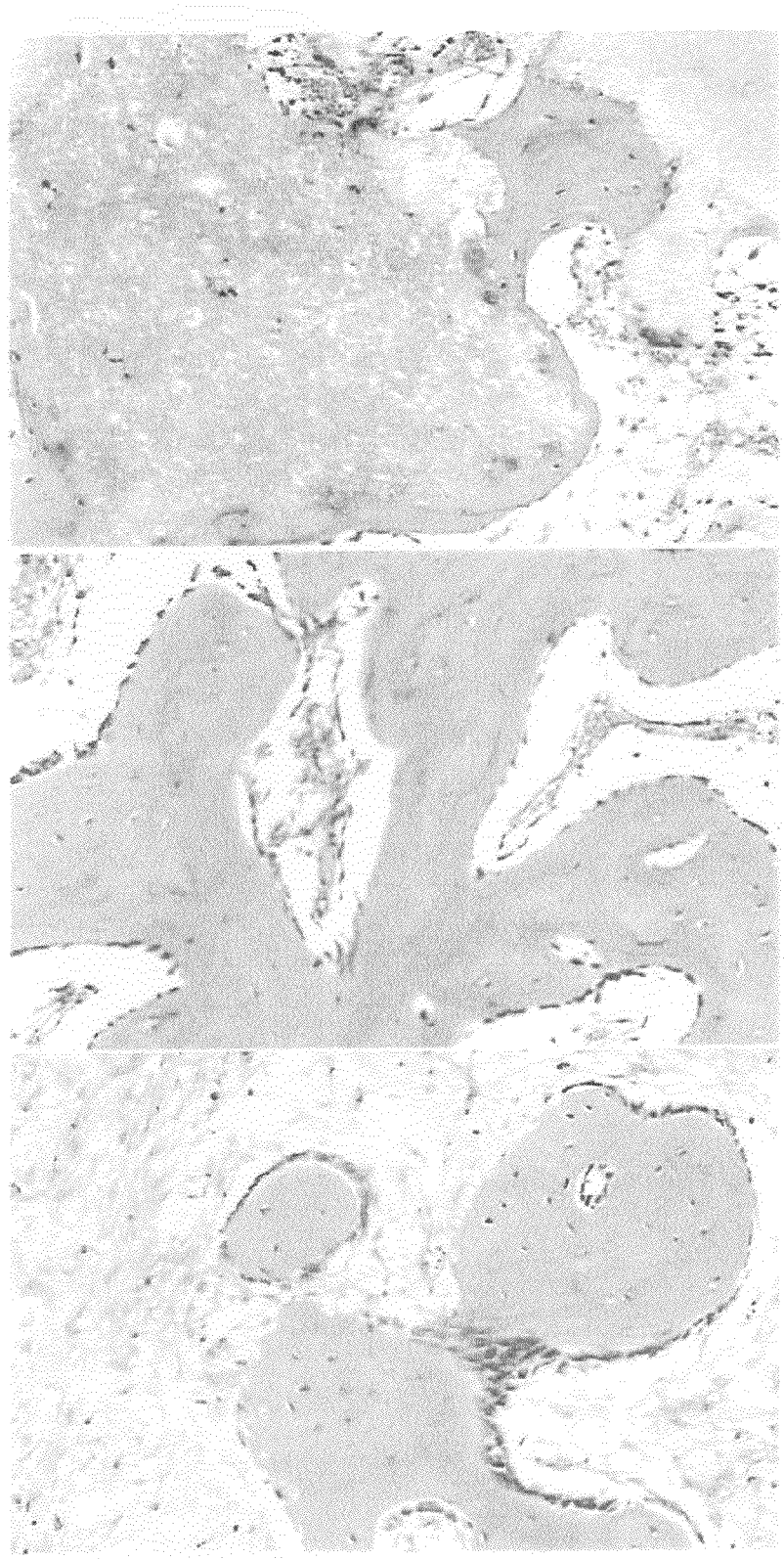
FIG. 20. Paraffin scanning image of animal number 295R (right tibia) at 4 weeks with OP-1. From the top, the sites are proximal, middle and distal, each containing β-TCP putty 89C, β-TCP putty 89F, control, respectively.
Figure 21:
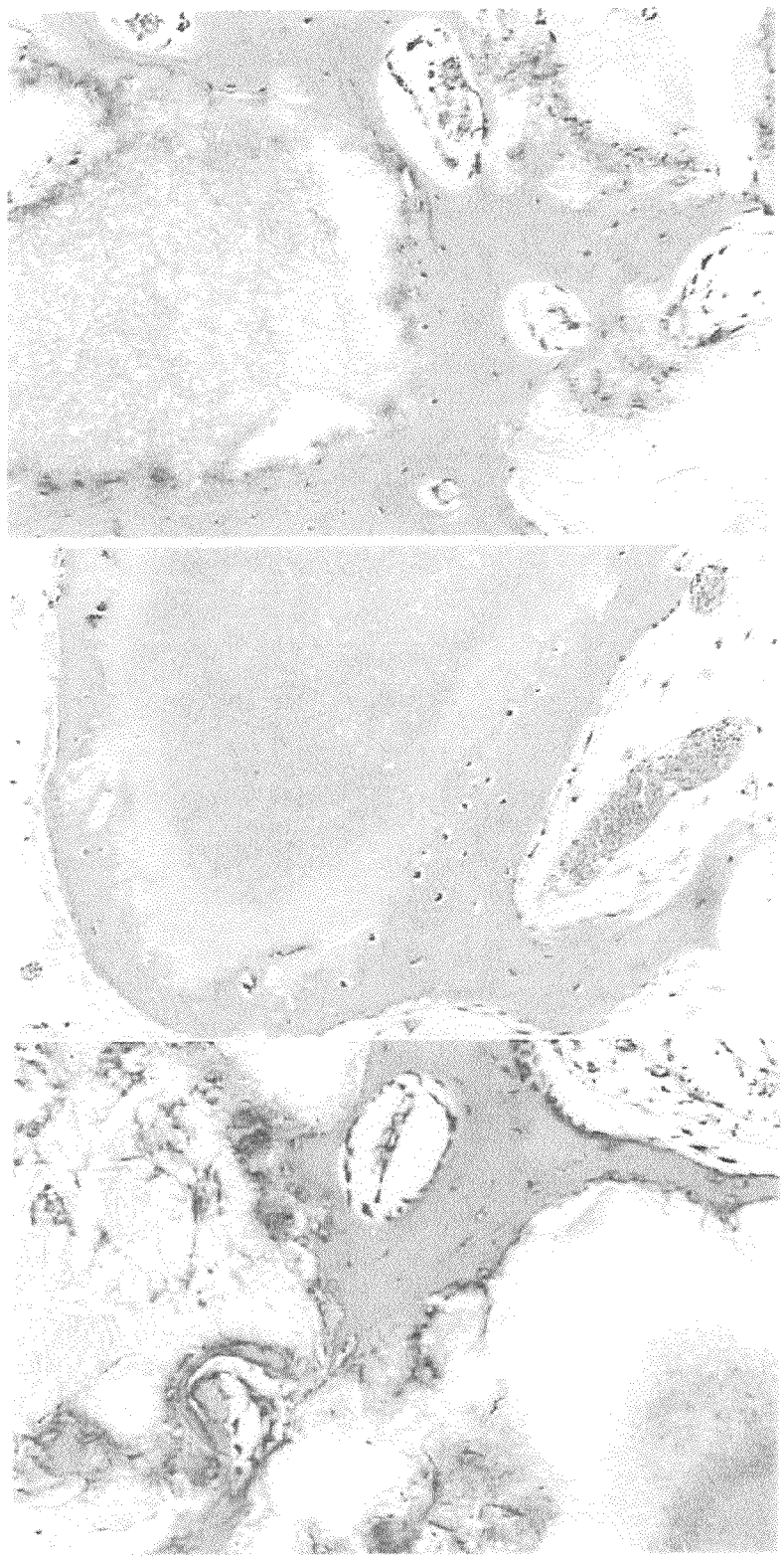
FIG. 21. Paraffin scanning image of animal number 299L (left tibia) at 8 weeks with placebo. From the top, the sites are proximal, middle and distal, each containing β-TCP putty 89B, β-TCP putty 89C, β-TCP putty 89F, respectively.
Figure 22:
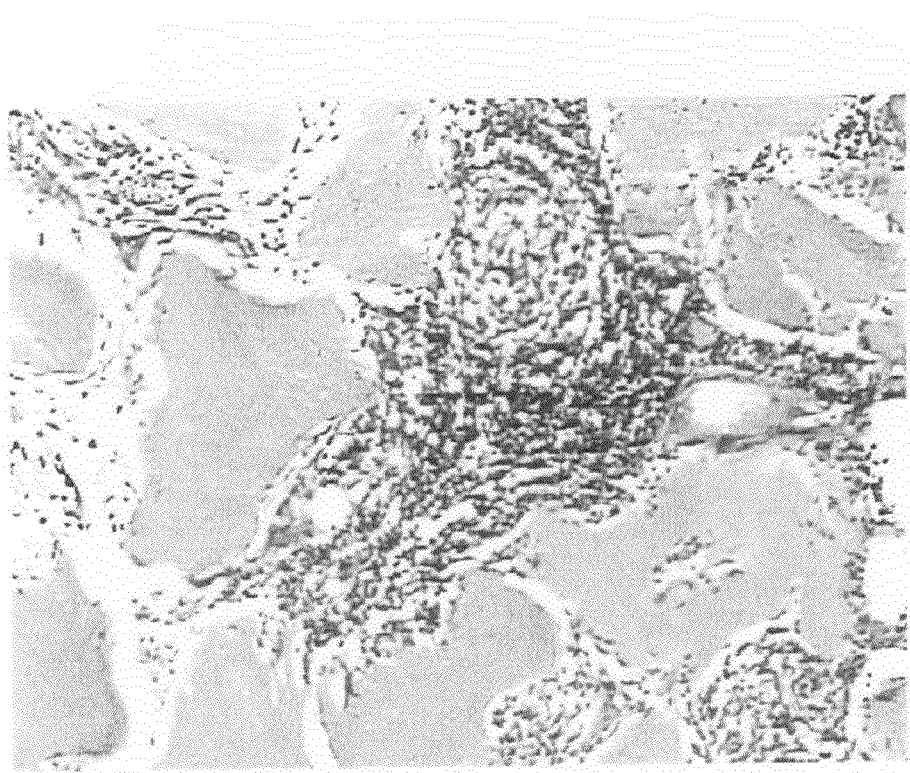
FIG. 22. Paraffin scanning image of animal number 299R (right tibia) at 8 weeks with placebo. From the top, the sites are middle and distal, each containing collagen 48C and β-TCP putty 89A, respectively.
Figure 22:
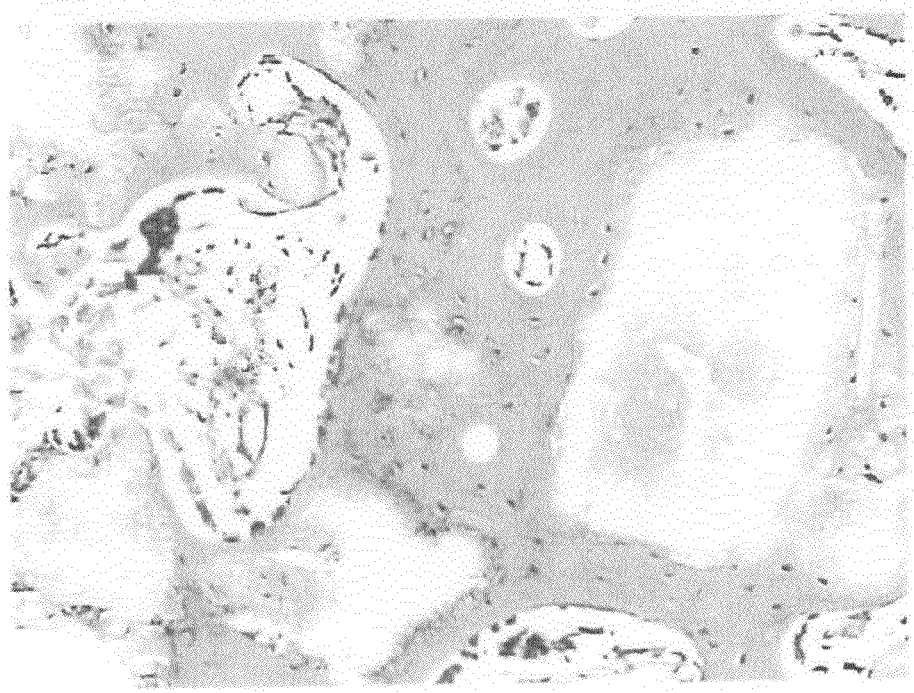
Figure 23:
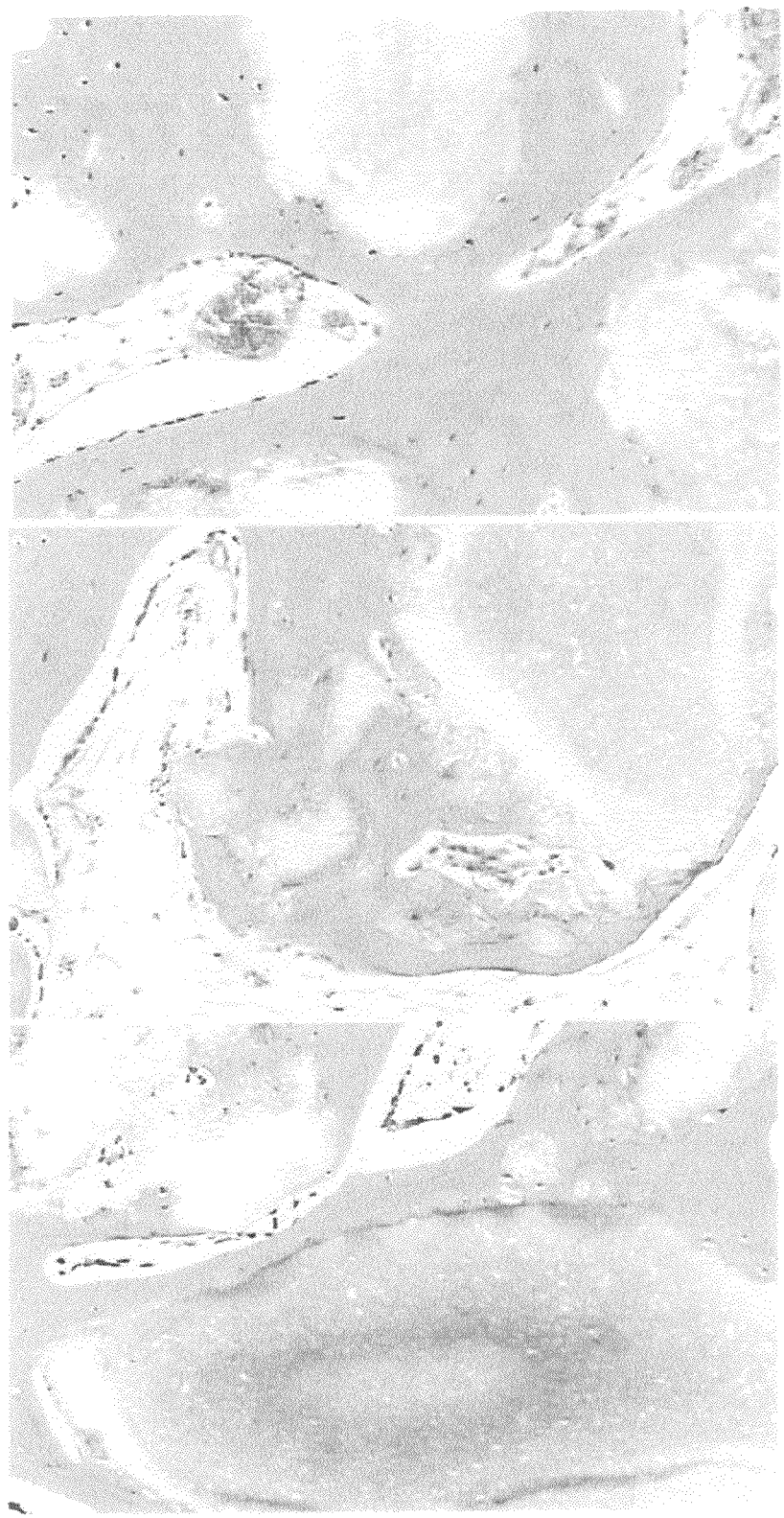
FIG. 23. Paraffin scanning image of animal number 138L (left tibia) at 8 weeks with OP-1. From the top, the sites are proximal, middle and distal, each containing β-TCP putty 89A, β-TCP putty 89B, β-TCP putty 89C, respectively.
Figure 24:
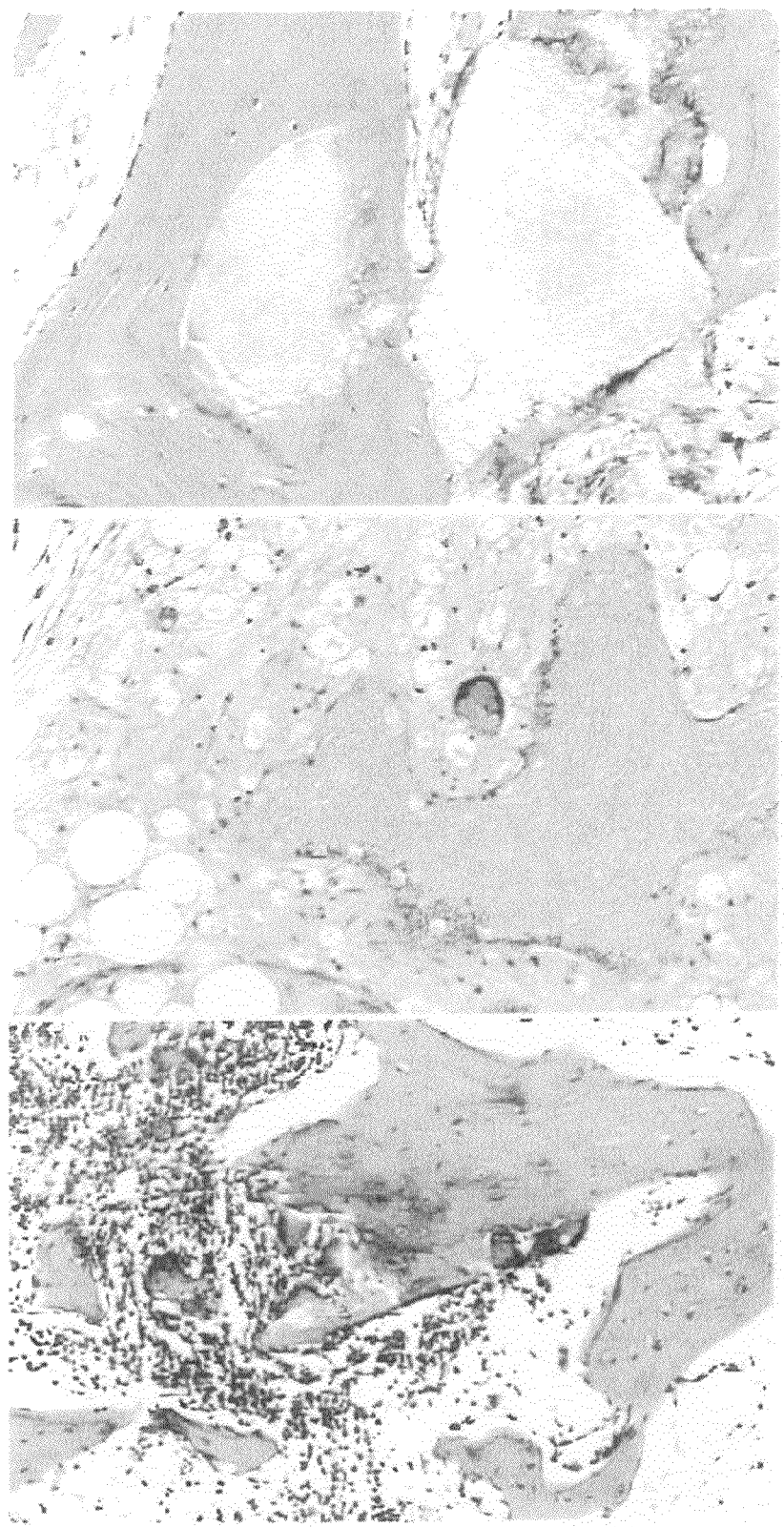
FIG. 24. Paraffin scanning image of animal number 138R (right tibia) at 8 weeks with OP-1. From the top, the sites are proximal, middle and distal, each containing β-TCP putty 89F, control, collagen 48C, respectively.

The β-TCP Putty II (89B) was present in all sites at 8 weeks in significant amounts (FIG. 5 proximal site and FIG. 7 middle site). There was no significant evidence of matrix resorption. OP-1 treated sites resulted in small amounts of new bone formation predominately at the cortical and periosteal level and closure at the defect site (FIG. 7 middle site). Placebo treated materials resulted in less bone formation at the cortical level and calcium particles blocking closure of the cortical defect (FIG. 5 proximal site). The inflammation noted previously in response to this material was not evident.

β-TCP Putty III (89C) was present in significant amounts in all six sites treated at 8 weeks (FIG. 5 middle site and FIG. 7 distal site). OP-1 treatment did not noticeably alter residual matrix volumes. Bone formation at the cortical level and a marked periosteal response was apparent in OP-1 treated specimens (FIG. 7 distal site). Little or no inflammation was observed in response to the β-TCP matrix independent of OP-1 treatment.

β-TCP Putty IV (89F) was present in significant amounts in all six sites treated at 8 weeks (FIG. 5 distal site and FIG. 8 proximal site). A few sites had less residual matrix than others. Generally, OP-1 treatment had no apparent effect on residual matrix volume. OP-1 treated sites resulted in greater bone formation throughout the matrix with an apparent cortical and periosteal response (FIG. 8 proximal site). Little or no inflammation was observed in response to the β-TCP matrix independent of OP-1 treatment.

Conclusion of the Above Results

Compared to the collagen material which demonstrated acute and chronic inflammation coupled with an FBGC response, the four porous β-TCP formulations resulted in little or no inflammation at four and eight weeks. OP-1-treatment in the porous β-TCP materials consistently exhibited marked bone formation at the cortical level and a reactive periosteal response that often resulted in cortical defect closure. Although the large granular (1-2 mm) β-TCP putty IV formulation appeared to allow bone ingrowth deeper in the matrix, there was greater inter-granular spacing compared to that observed in small granular β-TCP putties.

Paraffin Histology Study

Tissues from the sheep model bioassay were evaluated using paraffin sections and hematoxylin and eosin stain to evaluate the effect of particle size and porosity of the implant material on bone formation in and around particles.

Tibial specimens were sectioned so as to isolate implant sites in the proximal, middle and distal sites from four animals (138, 299, 297, and 295). These explants were decalcified, embedded in paraffin, sectioned and stained with hematoxylin and eosin.

Sections were viewed using light microscopy and interpreted for the effect of particle size and porosity. For specimens stratified in bone formation, the response from the cortical level was robust and deep, and the response was modest in the medullary compartment. Due to this stratification, the level extending from the endosteal cortex to a level 2-3 mm deep was evaluated.

Each of the four ceramic formulations were evaluated for bone formation in the pores and bone bridging across the particles. Bone formation in pores was assessed by counting pores that were completely isolated within a particle from the adjacent stroma. Pores that were obvious and generally round were counted. As pores were counted, a ratio was formed of those that had bone over those that did not. This is noted as the pore-fill ratio.

Figure 25:
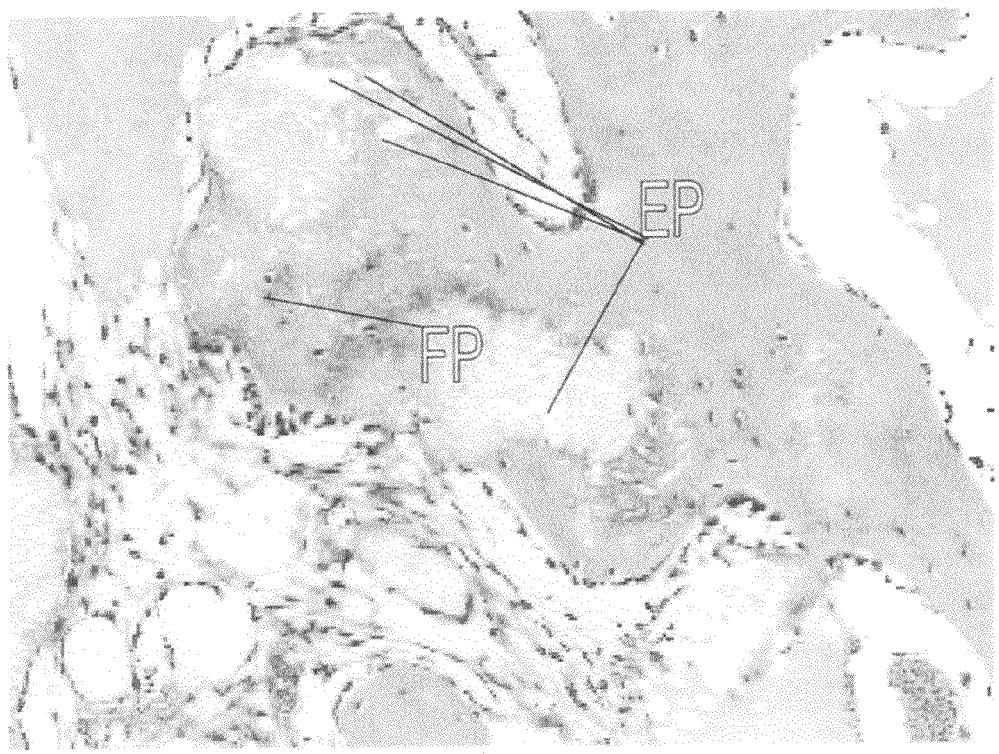
FIG. 25. Specimen 295L middle site showing one of the five pores with bone growth, where EP is an empty pore and FP is a filled pore.
Figure 26:
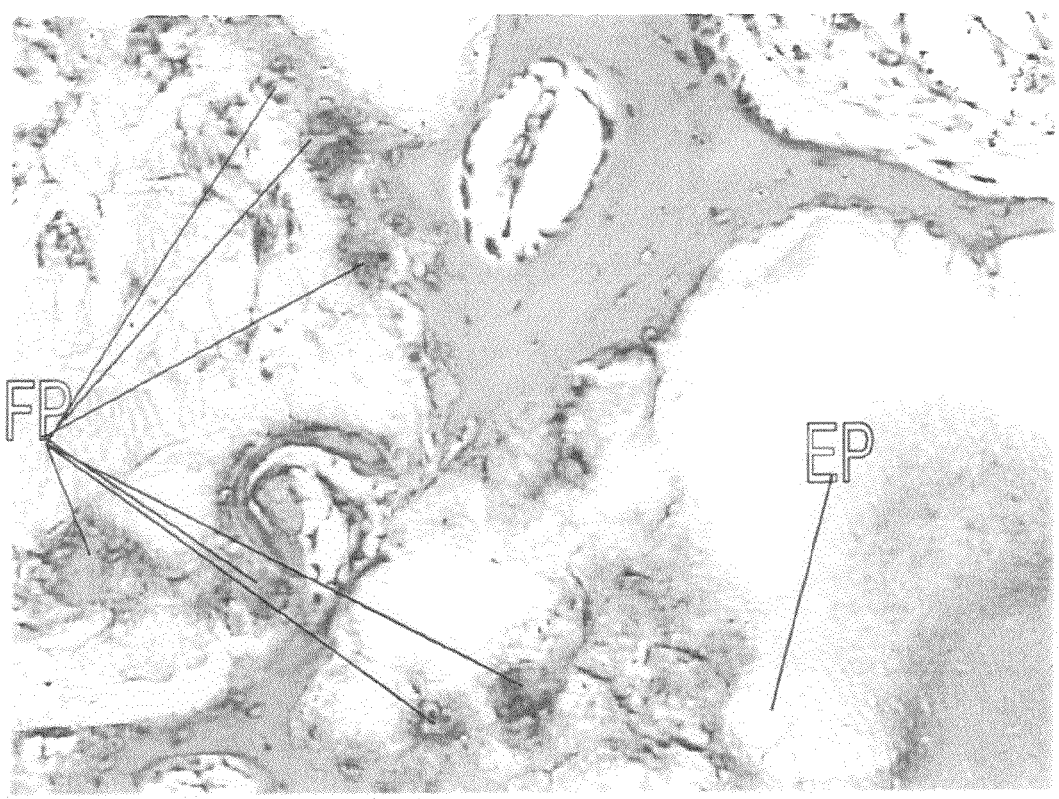
FIG. 26. Specimen 299L distal site showing 7 or 8 pores with bone growth, where EP is any empty pore and FP is a filled pore.
Figure 27:
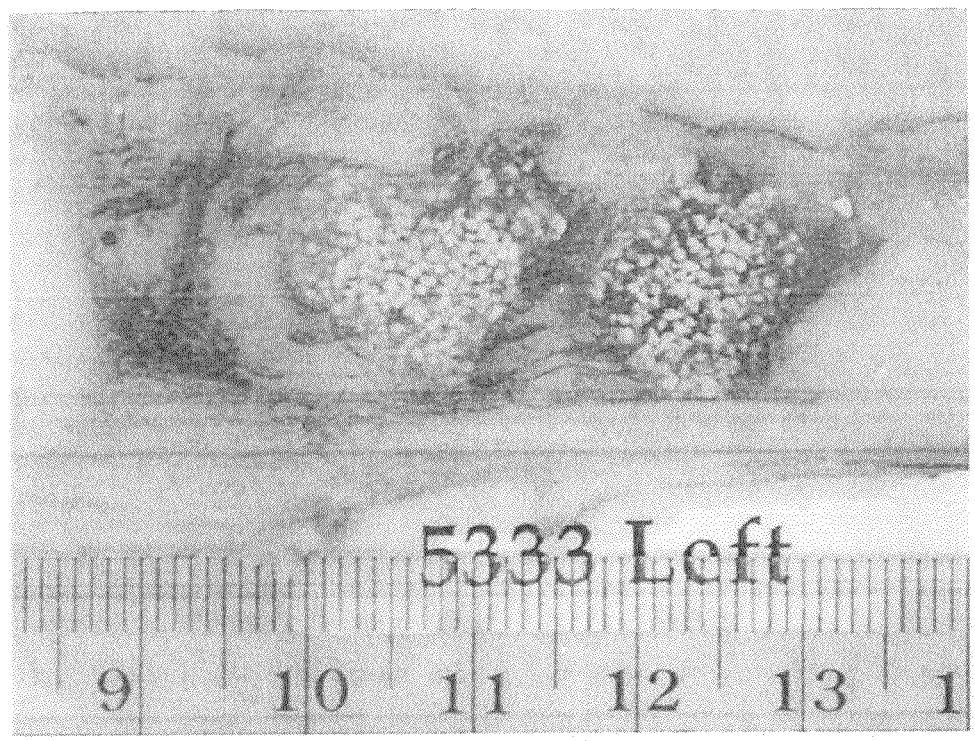
FIG. 27. Radiographic image of animal number 5333L (left tibia) at 4 weeks with OP-1 encapsulated in PLGA. From the left, the sites are proximal, middle and distal, each containing control, formulation 5 and formulation 4, respectively.
Figure 27:
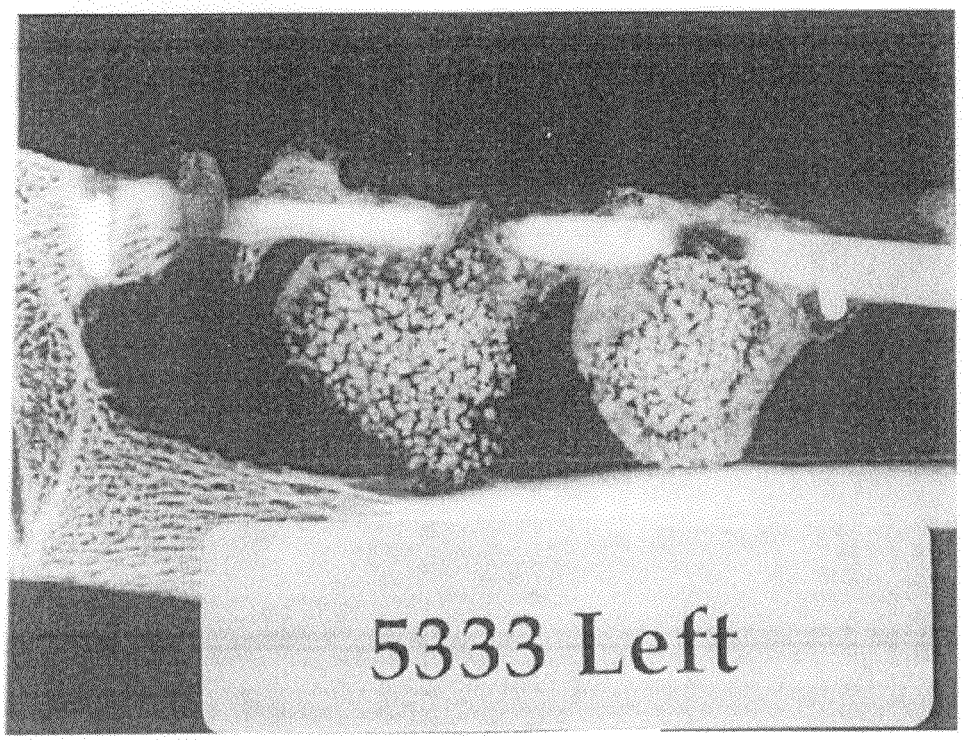
Figure 28:
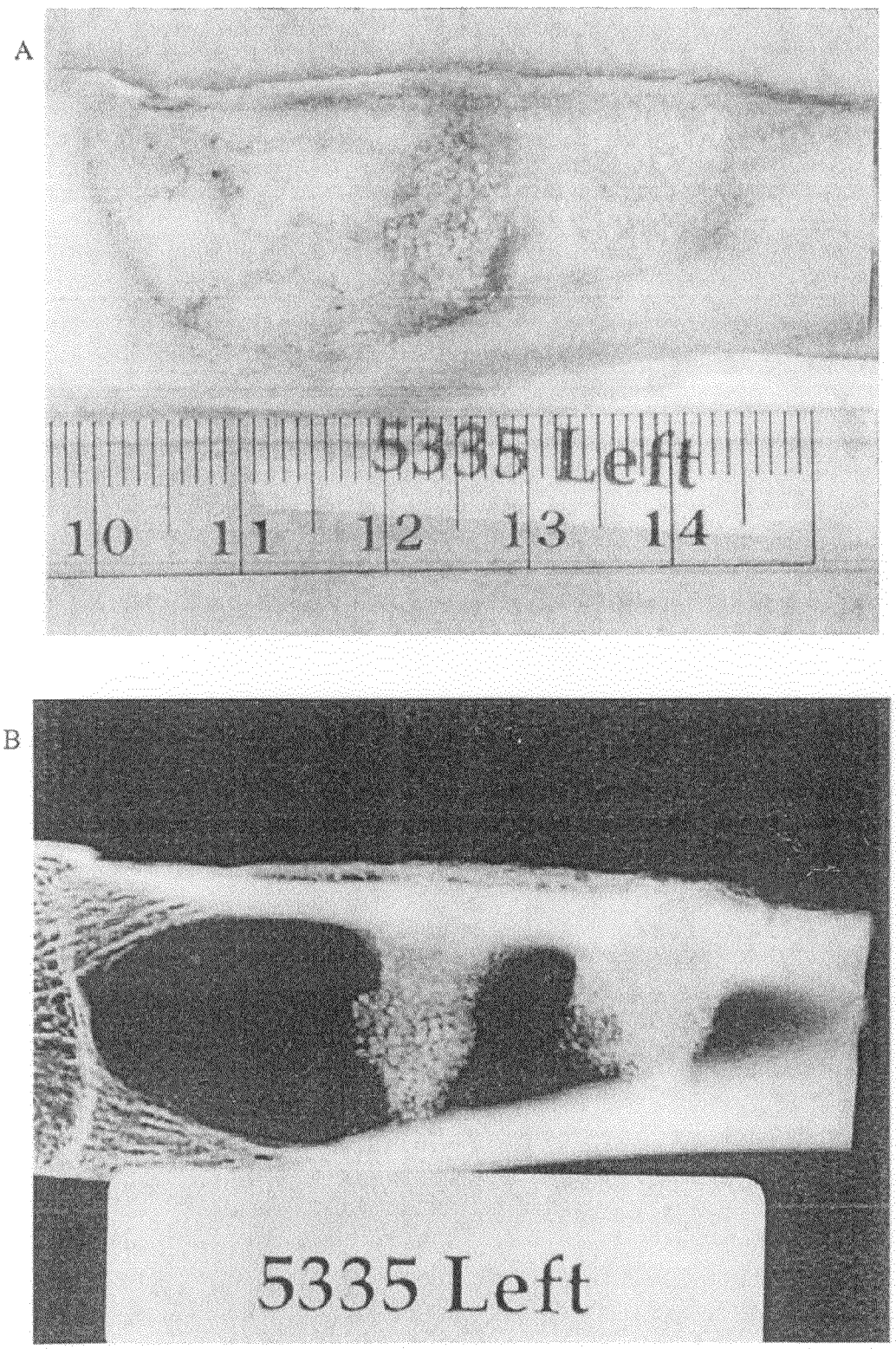
FIG. 28. Radiographic image of animal number 5335L (left tibia) at 8 weeks with OP-1 encapsulated in PLGA. From the left, the sites are proximal, middle and distal, each containing control, formulation 4 and formulation 5, respectively.

Pore counting was performed by scanning the field. In materials with few pores, the majority were counted as the field was scanned (FIG. 25). In materials with many pores, regions were counted and a new region was viewed and then counted (FIG. 26). The average of the regions or total count were presented in the ratio.

Bone bridging between particles was scored 0 to 2. A zero score was given to particles when the bone did not bridge to adjacent particles. A score of 1 was given when a couple to a few particles consistently showed bridging. A score of 2 was given when many of the particles were joined by vital bone trabeculae.

Tables 4 and 5 illustrate the pore-fill ratios and bone bridging scores for placebo and OP-1 at four weeks (FIGS. 17-20). Tables 6 and 7 illustrate the pore-fill ratios and bone bridging scores for placebo and OP-1 at eight weeks (FIGS. 21-24). Bone bridging was more pronounced for β-TCP putties made from 37.5% (w/w) pore-forming agent and having the smaller 0.5-1 mm granule size (Tables 4-7). The pore-fill ratio was generally equivalent for the β-TCP putty made from 25% and 37.5% (w/w) pore-forming agents. The β-TCP made from 12.5% (w/w) pore-forming agent had a lower pore-fill ratio (Tables 4-7). The pore-fill ratio was consistently higher in the 89F formulation due to the larger size of the particle (1-2 mm) with more pores per particle. Compared to the small particles (0.5-1 mm), there was less bone bridging in the larger particles due to the fact that more bone was required to bridge large particles.

TABLE 4

| Section | Treatment | Particle Size | Initial Pore-former % | Duration (wks) | Pore Fill Ratio | Bone Bridging |
|---|---|---|---|---|---|---|
| 297R-D | 89A | .5-1 mm | 12.5 | 4 | 2/10 | 0 |
| 297L-P | 89B | .5-1 mm | 25 | 4 | 6/10 | 0 |
| 297L-M | 89C | .5-1 mm | 37.5 | 4 | 6/7 | 0 |
| 297L-D | 89F | 1-2 mm | 25 | 4 | 10/10 | 0 |

Note:
Section 297R-D is from the right side (R), distal (D) site of animal 297. Section 297L-P is from the left side(L), proximal site (P) of animal 297. Section 297L-M is from the left side(L), middle site (M) of animal 297. Section 297L-D is from the left side(L), distal site (D) of animal 297.

TABLE 5

| Section | Treatment | Particle Size | Initial Pore-former % | Duration (wks) | Pore Fill Ratio | Bone Bridging |
|---|---|---|---|---|---|---|
| 295L-M | 89A | .5-1 mm | 12.5 | 4 | 6/11 | 2 |
| 295L-D | 89B | .5-1 mm | 25 | 4 | 8/11 | 1 |
| 295R-P | 89C | .5-1 mm | 37.5 | 4 | 6/8 | 2 |
| 295R-M | 89F | 1-2 mm | 25 | 4 | 10/10 | 2 |

Note:
Section 295L-M is from the left side (L), middle (M) site of animal 295. Section 295L-D is from the left side(L), distal site (D) of animal 295. Section 295R-P Is from the right side(R), proximal site (P) of animal 295. Section 295R-M is from the right side(R), middle site (M) of animal 295.

TABLE 6

| Section | Treatment | Particle Size | Initial Pore-former % | Duration (wks) | Pore Fill Ratio | Bone Bridging |
|---|---|---|---|---|---|---|
| 299R-D | 89A | .5-1 mm | 12.5 | 8 | 4/14 | 1 |
| 299L-P | 89B | .5-1 mm | 25 | 8 | 9/10 | 2 |
| 299L-M | 89C | .5-1 mm | 37.5 | 8 | 18/20 | 2 |
| 299L-D | 89F | 1-2 mm | 25 | 8 | 9/10 | 1 |

Note:
Section 299R-D is from the right side (R), distal (D) site of animal 299. Section 299L-P is from the left side(L), proximal site (P) of animal 299. Section 299L-M is from the left side(L), middle site (M) of animal 299. Section 299L-D is from the left side(L), distal site (D) of animal 299.

TABLE 7

| Section | Treatment | Particle Size | Initial Pore-former % | Duration (wks) | Pore Fill Ratio | Bone Bridging |
|---|---|---|---|---|---|---|
| 138L-P | 89A | .5-1 mm | 12.5 | 8 | 10/20 | 1 |
| 138L-M | 89B | .5-1 mm | 25 | 8 | 8/9 | 2 |
| 138L-D | 89C | .5-1 mm | 37.5 | 8 | 10/12 | 2 |
| 138R-P | 89F | 1-2 mm | 25 | 8 | 9/10 | 1 |

Note:
Section 138L-P is from the left side (L), proximal (P) site of animal 138. Section 138L-M is from the left side(L), middle site (M) of animal 138. Section 138L-D is from the left side(L), distal site (D) of animal 138. Section 138R-P is from the right side(R), proximal site (P) of animal 138.

Conclusion of Paraffin Histology Study

For β-TCP formulations, bone formation in pores became more apparent as the porosity increased. Bone formation in pores was less frequent in the material made from 12.5% pore-former compared to the material made from 37.5% pore-former. Although bone formation was more obvious in larger particles (1-2 mm), less bone bridging was observed in these large particles.

The collagen formulations resulted in no bone formation and a marked pathologic response. Moreover, these formulations resulted in a marked FBGCR and chronic fibroinflammatory response.

EXAMPLE 5

Feline Model Bioassay for Bone Repair

A femoral osteotomy defect is surgically prepared. Without further intervention, the simulated fracture defect would consistently progress to non-union. The effects of osteogenic compositions and devices implanted into the created bone defects are evaluated by the following study protocol.

Briefly, the procedure is as follows: Sixteen adult cats each weighing less than 10 lbs. undergo unilateral preparation of a 1 cm bone defect in the right femur through a lateral surgical approach. In other experiments, a 2 cm bone defect may be created. The femur is immediately internally fixed by lateral placement of an 8-hole plate to preserve the exact dimensions of the defect. Four different types of materials may be implanted in the surgically created cat femoral defects: group I is a negative control group with no test material; group II is implanted with biologically active porous $\beta$-TCP; group III is implanted with porous $\beta$-TCP and an osteogenic protein; and group IV is implanted with porous $\beta$-TCP, an osteogenic protein and MPSF.

All animals are allowed to ambulate ad libitum within their cages post-operatively. All cats are injected with tetracycline (25 mg/kg subcutaneously (SQ) each week for four weeks) for bone labeling.

In vivo radiomorphometric studies are carried out immediately at 4, 8, 12 and 16 weeks post-operative by taking a standardized X-ray of the lightly-anesthetized animal positioned in a cushioned X-ray jig designed to consistently produce a true anterio-posterior view of the femur and the osteotomy site. All X-rays are taken in exactly the same fashion and in exactly the same position on each animal. Bone repair is calculated as a function of mineralization by means of random point analysis. A final specimen radiographic study of the excised bone is taken in two planes after sacrifice.

Excised test and normal femurs may be immediately studied by bone densitometry, or wrapped in two layers of saline-soaked towels, placed into sealed plastic bags, and stored at −20° C. until further study. Bone repair strength, load-to-failure, and work-to-failure are tested by loading to failure on a specially designed steel 4-point bending jig attached to an Instron testing machine to quantitate bone strength, stiffness, energy absorbed and deformation to failure. The study of test femurs and normal femurs yields the bone strength (load) in pounds and work-to-failure in joules. Normal femurs exhibit a strength of 96 (+/−12) pounds. Osteogenic device-implanted femur strength should be corrected for surface area at the site of fracture (due to the "hourglass" shape of the bone defect repair). With this correction, the result should correlate closely with normal bone strength.

Following biomechanical testing, the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

Selected specimens from the bone repair site are homogenized in cold 0.15 M NaCl, 3 mM NaHCO$_3$, pH 9.0 by a Spex freezer mill. The alkaline phosphatase activity of the supernatant and total calcium content of the acid soluble fraction of sediment are then determined.

EXAMPLE 6

Rabbit Model Bioassay for Bone Repair

This assay is described in detail in Oppermann et al., U.S. Pat. No. 5,354,557; see also Cook et al., *J. of Bone and Joint Surgery*, 76-A, pp. 827-38 (1994), which are incorporated herein by reference). Ulnar non-union defects of 1.5 cm are created in mature (less than 10 lbs) New Zealand White rabbits with epiphyseal closure documented by X-ray. The experiment may include implantation of devices into at least eight rabbits per group as follows: group I negative control implants without test material; group II implants with porous $\beta$-TCP; group III implants with porous $\beta$-TCP and an osteogenic protein; group IV implants with porous $\beta$-TCP, osteogenic protein and MPSF combinations. Ulnae defects are followed for the full course of the eight week study in each group of rabbits.

In another experiment, the marrow cavity of the 1.5 cm ulnar defect is packed with activated osteogenic protein in porous $\beta$-TCP in the presence or absence of a MPSF. The bones are allografted in an intercalary fashion. Negative control ulnae are not healed by eight weeks and reveal the classic "ivory" appearance. In distinct contrast, the osteogenic protein/MPSF-treated implants "disappear" radiographically by four weeks with the start of remineralization by six to eight weeks. These allografts heal at each end with mild proliferative bone formation by eight weeks. This type of device serves to accelerate allograft repair.

Implants treated with osteogenic protein in the presence of a MPSF may show accelerated repair, or may function at the same rate using lower concentrations of the osteogenic protein. As was described above, the rabbit model may also be used to test the efficacy of and to optimize conditions under which a particular osteogenic protein/MPSF combination can induce local bone formation.

EXAMPLE 7

Dog Ulnar Defect Bioassay for Bone Repair

This assay is performed essentially as described in Cook et al., *Clinical Orthopaedics and Related Research*, 301, pp. 302-112 (1994), which is incorporated herein by reference). Briefly, an ulnar segmental defect model is used to evaluate bone healing in 35-45 kg adult male dogs. Experimental composites comprising 500 mg of porous $\beta$-TCP are reconstituted with varying amounts of OP-1 in the absence or presence of increasing concentrations of one or more putative MPSFs. Any osteogenic protein may be used in place of OP-1 in this assay. Implantations at defect sites are performed with one carrier control and with the experimental series of OP-1 and OP-1/MPSF combinations being tested. Mechanical testing is performed on ulnae of animals receiving composites at 12 weeks after implantation. Radiographs of the forelimbs are obtained weekly until the animals are sacrificed at either 12 or 16 postoperative weeks. Histological sections are analyzed from the defect site and from adjacent normal bone.

The presence of one or more MPSFs may increase the rate of bone repair in dog. The presence of one or more MPSFs may also permit the use of reduced concentrations of osteogenic protein per composite to achieve similar or the same results.

EXAMPLE 8

Monkey Ulnar and Tibial Defect Bioassay for Bone Repair

This bone healing assay in African green monkeys is performed essentially as described in Cook et al., *J. Bone and Joint Surgery*, 77A, pp. 734-50 (1995), which is incorporated herein by reference. Briefly, a 2.0 cm osteoperiosteal defect is created in the middle of the ulnar shaft and filled with an implant comprising porous β-TCP matrices containing OP-1 in the absence or presence of increasing concentrations of one or more putative MPSFs. Experimental composites comprising porous β-TCP matrices reconstituted with varying amounts of OP-1 in the absence or presence of increasing concentrations of one or more putative MPSFs are used to fill 2.0 cm osteoperiosteal defects created in the diaphysis of the tibia. Any osteogenic protein may be used in place of OP-1 in this assay. Implantations at defect sites are performed with one carrier control and with the experimental series of OP-1 and OP-1/MPSF combinations being tested. Mechanical testing is performed on ulnae and tibia of animals receiving composites. Radiographs and histological sections are analyzed from the defect sites and from adjacent normal bone as described in Cook et al.

The presence of one or more MPSFs can increase the rate of bone repair in the monkey. The presence of one or more MPSFs may also permit the use of reduced concentrations of osteogenic protein per composite to achieve similar or the same results.

EXAMPLE 9

Goat Model Fracture Healing Bioassay

This fracture healing assay in sheep is performed essentially as described in Blokhius et al., *Biomaterials*, 22, pp. 725-730 (2001), which is incorporated herein by reference. A closed midshaft fracture is created in the left tibia of adult female goats with a custom-made three point bending device. The fractures are stabilized with an external fixator, which is placed at the lateral side of the tibia. Three different types of materials are implanted in the goat defects via injection: group I is a negative control group with no test material; group II is implanted with the biologically active porous β-TCP; group III is implanted with porous β-TCP and an osteogenic protein; and group IV is implanted with porous β-TCP and an osteogenic protein encapsulated in PLGA. The test material is placed in the fractured gap. Mechanical testing (four-point non-destructive bending test) is performed on the animals receiving composites at two weeks and four weeks. After the mechanical testing, anterior, posterior, lateral, and medial slices of the fracture gap are sawn to perform radiographs and histological sections.

EXAMPLE 10

Fusion Assay of an Unstable Motor Segment of the Sheep Lumbar Spine

This assay investigates the healing of osseous and discoligamentous instability. A motor segment of the spine is a functional unit consisting of two vertebral bodies lying one above the other, and an intervertebral disc.

A trial group consists of 12 sheep. Two control groups of 12 sheep each are used. The surgical area at the inferior lumbar spine is prepared after introduction of general anesthesia and placing the animals in prone position. A skin incision of about 12 cm in length above the spinous processes of the inferior lumbar spine is made. After transsection of the subcutis and fascia, the back muscles are moved to the side.

Intubation anesthesia is applied by intramuscular injection of 1.5 ml xylazine (Rompun®). Further dosage can be administered as needed. The sedation requires placement of an intravenous indwelling catheter after puncturing an ear vein. The anesthesia is introduced through the catheter by providing 3-5 mg of thiopental (Trapana®) per kilogram of body weight. After endotracheal intubation, the animals are ventilated using oxygen (30%), nitrous oxide (laughing gas) and isoflurane (Isofluran®). During the entire surgery, the analgesic fentanyl dihydrogen citrate (Fentanyl®) having a dosage 0.2-0.4 mg, is administered. At the same time, relaxation is achieved by administration of atracurium besilate (Atracurium®) at a dosage of 0.5 mg/kg of body weight.

After complete exposure of the pedicles of lumbar vertebral bodies L4 to L6, a bilateral instrumentation of the pedicles L4 and L6 takes place. This is performed by using pedicle screws of 5 mm or 6 mm in diameter, depending on the diameter found in the pedicles. Subsequently, a bilateral transpedicular removal of the disc of the cranial motor segment L4/L5 is performed over the pedicle of L5 under pediculoscopic control. The endplates of the affected vertebral bodies are decorticated.

Inter- and intracorporal application of test samples occurs via a transpedicular cannula in all 12 sheep of the trial group. Test samples include porous β-TCP, osteogenic protein or osteogenic protein encapsulated in PLGA in varying concentrations. In the first control group that consists of 12 sheep, only the porous β-TCP is applied. In the second control group, autologous spongiosa is administered instead of the composition of this invention.

Finally, the internal fixator is installed completely. The type of the internal fixator as well as the necessary instrumentation and surgical procedure is standardized and well known to the skilled practitioner. Drains are placed and the wound is closed using absorbable suture for fascia and subcutis as well as skin staples.

During the entire surgical procedure, an x-ray image amplifier is available for intraoperative fluoroscopy. This facilitates exact orientation during the execution of the above steps.

Harvesting of the 12 sheep administered with autologous spongiosa is carried out under anesthesia as follows: the left iliac crest skin and fascia is cut by making a longitudinal incision about 8 cm long. The gluteal muscles are moved subperiostally and the cancellous bone graft is harvested from the iliac crest after an osteotomy. Bleeding control and placement of a Drain is performed upon closure of the wound in layers. The harvesting procedure is standard and known to an ordinary person skilled in the art Clinical Observations Daily neurologic examinations are performed to evaluate the gait of the animals as well as neurological deficits that may occur postoperatively. Operative wounds are closely examined each day. Body weights are measured preoperatively and at the time of euthanasia.

Radiographic Analysis

Before evaluation, the complete lumbar spine is freshly dissected, and the internal fixator is carefully removed. Anteroposterior and plain lateral radiographs of the operated spinal segments are obtained under consistent conditions of milliamperes, kilovolts, and seconds at 0 and 8 weeks to assist in fusion evaluation. The status of the fusion are evaluated with use of the grading system documented by Lenke et al., *J.*

*Spinal Disord*, 5, pp. 433-442 (1992), incorporated herein by reference. With this system, A indicates a big, solid trabeculated bilateral fusion mass (definitely solid); B, a big, solid unilateral fusion mass with a small contralateral fusion mass (possibly solid); C, a small, thin bilateral fusion mass with an apparent crack (probably not solid); and D, bilateral resorption of the graft or fusion mass with an obvious bilateral pseudarthrosis (definitely not solid).

Additionally, computerized tomography scans are performed to assess the fusion mass in cross sections and in saggital-plane reconstructions. For each fusion mass, approximately forty sequential computerized tomography scans are made with use of two-millimeter slice intervals and subsequent reconstruction in the saggital plane under consistent magnification and radiographic conditions.

Biomechanical Testing

Four specimens of each group are evaluated biomechanically. After radiographic analysis, all muscles are carefully removed while maintaining the ligamentous and bony structures. The spines are frozen at −20° C. For each of these specimens, the upper half of the upper vertebra and the lower half of the lower vertebra of the motion segment L4/L5 are embedded in polymethylmethacrylate (Technovit 3040; Heraeus Kulzer GmbH, Wehrheim/Ts, Germany). Each specimen is then fixed and tested without preload in a spine tester in a non-destructive testing mode. Alternating sequences of flexion/extension, axial right/left rotation, and right/left lateral bending moments are applied continuously at a constant rate of 1.7 degrees/second by stepper motors integrated in the gimbal of the spine tester. Two precycles are applied to minimize the effect of the viscous component in the viscoelastic response, and data are collected on the third cycle. Range of motion, neutral zone, and two stiffness parameters are determined from the resulting load-deformation curves.

Histology/Histomorphometry

Eight specimens of each group are evaluated histologically after two, four or eight weeks postoperatively. After radiographic analysis, the spines are fixed in 10% formalin-solution. Cross sections of either specimen are obtained to evaluate bony fusion, cellular reactions, biocompatibility, and signs of cement-integration/degradation. Qualitative histologic assessment of the fusion mass at the operative site are made for the presence of giant cells, inflammatory cells, or fibrous responses where the implanted materials may have been encapsulated. In addition, the osteoid found within the trabecular fusion mass and the amount of trabecular bone are assessed. Histomorphometric variables, such as the percentage of osteoid, osteoid thickness, number of osteoblasts per millimeter bone surface, and number of osteoclasts per millimeter bone surface are determined.

Fluorochrome Labeling

Eight animals are subjected to intravenous application of 90 milligrams of xylenol orange per kilogram of body weight two weeks postoperatively, 10 milligrams of calcein green per kilogram of body weight four weeks postoperatively, and 25 milligrams of doxycyclinhyclate yellow per kilogram of body weight six weeks postoperatively. This regimen follows the method published by Rahn and Perren. See, e.g., Rahn et al., *Stain Technology*, 46, pp. 125-129 (1971); Rahn et al., *Akt Traumatol*, 10, pp. 109-115 (1980). Fluorochrome sequential analysis is then performed by Fluorescence microscopy on the specimens under UV light for qualitative and quantitative dynamic evaluation.

EXAMPLE 11

Repair of Osteochondral Defects in Dogs

A total of 12 adult male dogs are utilized. Bilateral osteochondral defects, 5.0 mm in diameter and 6 mm deep, penetrating the subchondral bone, are created in the central load bearing region of each medial femoral condyle. In 6 animals, the right defects will receive the high dose OP-1 encapsulated in PLGA. The left limb of all animals will receive the collagen matrix plus CMC to serve as a control. The remaining 6 dogs receive a low dose OP-1 encapsulated in PLGA on the right side and a control on the left side. The animals are sacrificed at 16 weeks post-implantation. At sacrifice, the distal femurs are retrieved en bloc and the defect sites are evaluated histologically and grossly based on the scheme of Moran et al., *J. Bone Joint Surg.* 74B, pp. 659-667 (1992), which is incorporated herein by reference.

Using standard aseptic techniques, surgery is performed under isofluorane gas anesthesia and the animals are monitored by electrocardiogram and heart rate monitors. Pre-surgical medication is administered approximately 20-30 minutes prior to anesthesia induction. The presurgical medication will consist of butorphanol tartrate (0.05 mg/kg body weight). Anesthesia is administered by intravenous injection of sodium pentothal (17.5 mg/kg body weight). Following induction, an endotracheal tube is placed and anesthesia is maintained by isofluorane inhalation. Surgery is performed by making a medial parapatellar incision approximately 4 cm in length. The patella is retracted laterally to expose the femoral condyle. In the right medial condyle, a 5.0 mm diameter defect extending through the cartilage layer and penetrating the subchondral bone to a depth of 6 mm is created with a specially designed or modified 5.0 mm drill bit. After copious irrigation with saline to remove bone debris and spilled marrow cells, the appropriate concentration of OP-1 encapsulated in PLGA is carefully packed into each defect site with a blunt probe and by hand. A sufficient amount of OP-1 is placed within the defect so that it will flush with the articulating surface. While protecting the implanted material, the joint is irrigated to remove any implant not placed within the defects. The joint capsule and soft-tissues are then meticulously closed in layers with resorbable suture. The procedure is repeated on the contralateral side with placement of a control.

Butorphanol tartrate (0.05 mg/kg body weight) is administered subcutaneously as required. Animals are administered intramuscular antibiotics for four days post-surgery and routine anterior-posterior radiographs are taken immediately after surgery to insure proper surgical placement. Animals are kept in 3×4 feet recovery cages until the animal is able to tolerate weight bearing. Then, the animals are transferred to runs and allowed unrestricted motion.

Radiographs of the hindlimbs are obtained preoperatively, immediately postoperative, and at 16 weeks (sacrifice). The preoperative radiographs are used to assure that no pre-existing abnormalities are present and to verify skeletal maturity. Postoperative radiographs are used to assess defect placement. Sacrifice radiographs are used to assess the rate of healing and restoration of the subchondral bone and the articulating surface. Radiographs are obtained within one week of the evaluation date.

At the appropriate time, animals are sacrificed using an intravenous barbiturate overdose. The distal femurs are immediately harvested en bloc and stored in saline soaked towels, placed in plastic bags labeled with the animal number, right or left designation, and any other necessary identifiers. High power photographs of the defect sites are taken and carefully labeled. Prior to sacrifice venous blood is drawn for routine blood count with cell differential. Soft tissues are meticulously dissected away from the defect site. The proximal end of the femur is removed. All specimens are prepared for histologic evaluation immediately after gross grading and photography. On a water cooled diamond saw each defect site is isolated.

The gross appearance of the defect sites and repair tissue is graded based upon the study of Moran et al., supra. Points are apportioned according to the presence of intra-articular adhesions, restoration of the articular surface, cartilage erosion and appearance.

The individual specimens are fixed by immersion in 4% paraformaldehyde solution and prepared for decalcified histologic processing. Three sections from three levels are cut from each block. Levels 1 and 3 are closest to the defect perimeter. Level 2 is located at the defect center. Three sections from each level may be stained with toluidine blue and Safranin O and fast green. Sections are graded based upon the scheme of Moran et al., supra. This analysis apportions points based upon the nature of the repair tissue, structural characteristics, and cellular changes. Descriptive statistics are calculated for gross and histologic parameters.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A method of producing porous β-tricalcium phosphate (β-TCP) granules that have a particle size of 0.1-2 mm, and that comprise a multiplicity of pores having a pore diameter size of 20-500 μm and being single separate voids partitioned by walls and being not interconnected, comprising the steps of:
   (a) blending a TCP powder with a pore-forming agent;
   (b) adding a granulating solution to form a crumbly mass;
   (c) passing the crumbly mass through a sieve to form granules;
   (d) vaporizing the pore-forming agent at 700-800° C.; and
   (e) sintering the granules to form the porous β-TCP granules.

2. The method of claim 1, wherein the proportion of the pore-forming agent is 37.5% by weight.

3. The method of claim 1, wherein the sieve is in the size range of 500-1000 μm or 1000-1700 μm.

4. The method of claim 1, wherein the granules are sintered at 1000-1200° C. and followed by a slow cooling step to form the porous β-TCP granules.

5. The method of any one of claims 1 to 4, wherein the pore-forming agent is selected from the group consisting of naphthalene, prepolymers of polyacrylates, prepolymers of polymethacrylates, polymethacrylates, polymethyl methacrylate, copolymers of methyl acrylate and methyl methacrylate, polystyrene, polyethylene glycol, crystalline cellulose, fibrous cellulose, polyurethanes, polyethylenes, nylon resins and acrylic resins.

6. The method of any one of claims 1 to 4, wherein the granulating solution comprises a compound selected from the group consisting of polyvinyl pyrrolidone, starch, gelatin, polyvinyl alcohol, polyethylene oxide, hydroxyethyl cellulose, polyvinyl butyral and cellulose acetate butyrate.

7. The method of any one of claims 1 to 4, wherein the porous β-TCP granules are sieved after sintering.

8. The method of claim 1, wherein the proportion of the pore-forming agent is 10%-50% by weight.

9. The method of claim 1, wherein the proportion of the pore-forming agent is 30-40% by weight.

10. The method of claim 1, wherein the pore-forming agent is in bead or resin form.

11. The method of claim 1, wherein the granulating solution is an aqueous solution.

12. The method of claim 1, wherein the pore diameter size is 410-460 μm.

13. The method of claim 1, wherein the pore diameter size is 40-190 μm.

14. The method of claim 1, wherein the pore diameter size is 20-95 μm.

15. The method of claim 1, wherein the pore diameter size is 50-125 μm.

* * * * *

```
                          SEQUENCE LISTING

<160> NUMBER OF SEQ ID NOS: 11

<210> SEQ ID NO 1
<211> LENGTH: 431
<212> TYPE: PRT
<213> ORGANISM: Homo sapiens

<400> SEQUENCE: 1

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
    65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270
```

```
Lys Gln Pro Phe Met Val Ala Phe Lys Ala Thr Glu Val His Phe
        275                 280                 285
Arg Ser Ile Arg Ser Thr Gly Ser Lys Gln Arg Ser Gln Asn Arg Ser
        290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
                340                 345                 350
Gly Tyr Ala Ala Tyr Tyr Cys Glu Gly Glu Cys Ala Phe Pro Leu Asn
                355                 360                 365
Ser Tyr Met Asn Ala Thr Asn His Ala Ile Val Gln Thr Leu Val His
        370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
                420                 425                 430

<210> SEQ ID NO 2
<211> LENGTH: 96
<212> TYPE: PRT
<213> ORGANISM: Artificial Sequence
<220> FEATURE:
<223> OTHER INFORMATION: Description of Artificial Sequence: Synthetic
      amino acid sequence: COP5

<400> SEQUENCE: 2

Leu Tyr Val Asp Phe Ser Asp Val Gly Trp Asp Asp Trp Ile Val Ala
1               5                   10                  15
Pro Pro Gly Tyr Gln Ala Phe Tyr Cys His Gly Glu Cys Pro Phe Pro
                20                  25                  30
Leu Ala Asp His Phe Asn Ser Thr Asn His Ala Val Val Gln Thr Leu
        35                  40                  45
Val Asn Ser Val Asn Ser Lys Ile Pro Lys Ala Cys Cys Val Pro Thr
    50                  55                  60
Glu Leu Ser Ala Ile Ser Met Leu Tyr Leu Asp Glu Asn Glu Lys Val
65                  70                  75                  80
Val Leu Lys Tyr Asn Gln Glu Met Val Val Glu Gly Cys Gly Cys Arg
                85                  90                  95

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence: Synthetic
      amino acid sequence: COP7

<400> SEQUENCE: 3

Leu Tyr Val Asp Phe Ser Asp Val Gly Trp Asn Asp Trp Ile Val Ala
1               5                   10                  15
Pro Pro Gly Tyr His Ala Phe Tyr Cys His Gly Glu Cys Pro Phe Pro
                20                  25                  30
Leu Ala Asp His Leu Asn Ser Thr Asn His Ala Val Val Gln Thr Leu
        35                  40                  45
Val Asn Ser Val Asn Ser Lys Ile Pro Lys Ala Cys Cys Val Pro Thr
```

```
            50              55              60
Glu Leu Ser Ala Ile Ser Met Leu Tyr Leu Asp Glu Asn Glu Lys Val
 65                  70                  75                  80

Val Leu Lys Tyr Asn Gln Glu Met Val Val Glu Gly Cys Gly Cys Arg
                 85                  90                  95
```

```
<210> SEQ ID NO 4
<211> LENGTH: 102
<212> TYPE: PRT
<213> ORGANISM: Artificial Sequence
<220> FEATURE:
<223> OTHER INFORMATION: Description of Artificial Sequence: Synthetic
      formula sequence of OPX
<220> FEATURE:
<221> NAME/KEY: MOD_RES
<222> LOCATION: (2)
<223> OTHER INFORMATION: Lys or Arg
<220> FEATURE:
<221> NAME/KEY: MOD_RES
<222> LOCATION: (3)
<223> OTHER INFORMATION: Lys or Arg
<220> FEATURE:
<221> NAME/KEY: MOD_RES
<222> LOCATION: (11)
<223> OTHER INFORMATION: Arg or Gln
<220> FEATURE:
<221> NAME/KEY: MOD_RES
<222> LOCATION: (16)
<223> OTHER INFORMATION: Gln or Leu
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (23)
<223> OTHER INFORMATION: Glu or Gln
<220> FEATURE:
<221> NAME/KEY: MOD_RES
<222> LOCATION: (26)
<223> OTHER INFORMATION: Ala or Ser
<220> FEATURE:
<221> NAME/KEY: MOD_RES
<222> LOCATION: (35)
<223> OTHER INFORMATION: Ala or Ser
<220> FEATURE:
<221> NAME/KEY: MOD_RES
<222> LOCATION: (39)
<223> OTHER INFORMATION: Asn or Asp
<220> FEATURE:
<221> NAME/KEY: MOD_RES
<222> LOCATION: (41)
<223> OTHER INFORMATION: Tyr or Cys
<220> FEATURE:
<221> NAME/KEY: MOD_RES
<222> LOCATION: (50)
<223> OTHER INFORMATION: Val or Leu
<220> FEATURE:
<221> NAME/KEY: MOD_RES
<222> LOCATION: (52)
<223> OTHER INFORMATION: Ser or Thr
<220> FEATURE:
<221> NAME/KEY: MOD_RES
<222> LOCATION: (56)
<223> OTHER INFORMATION: Phe or Leu
<220> FEATURE:
<221> NAME/KEY: MOD_RES
<222> LOCATION: (57)
<223> OTHER INFORMATION: Ile or Met
<220> FEATURE:
<221> NAME/KEY: MOD_RES
<222> LOCATION: (58)
<223> OTHER INFORMATION: Asn or Lys
<220> FEATURE:
<221> NAME/KEY: MOD_RES
<222> LOCATION: (60)
<223> OTHER INFORMATION: Glu, Asp or Asn
```

```
<220> FEATURE:
<221> NAME/KEY: MOD_RES
<222> LOCATION: (61)
<223> OTHER INFORMATION: Thr, Ala or Val
<220> FEATURE:
<221> NAME/KEY: MOD_RES
<222> LOCATION: (65)
<223> OTHER INFORMATION: Pro or Ala
<220> FEATURE:
<221> NAME/KEY: MOD_RES
<222> LOCATION: (71)
<223> OTHER INFORMATION: Gln or Lys
<220> FEATURE:
<221> NAME/KEY: MOD_RES
<222> LOCATION: (73)
<223> OTHER INFORMATION: Asn or Ser
<220> FEATURE:
<221> NAME/KEY: MOD_RES
<222> LOCATION: (75)
<223> OTHER INFORMATION: Ile or Thr
<220> FEATURE:
<221> NAME/KEY: MOD_RES
<222> LOCATION: (80)
<223> OTHER INFORMATION: Phe or Tyr
<220> FEATURE:
<221> NAME/KEY: MOD_RES
<222> LOCATION: (82)
<223> OTHER INFORMATION: Asp or Ser
<220> FEATURE:
<221> NAME/KEY: MOD_RES
<222> LOCATION: (84)
<223> OTHER INFORMATION: Ser or Asn
<220> FEATURE:
<221> NAME/KEY: MOD_RES
<222> LOCATION: (89)
<223> OTHER INFORMATION: Lys or Arg
<220> FEATURE:
<221> NAME/KEY: MOD_RES
<222> LOCATION: (91)
<223> OTHER INFORMATION: Tyr or His
<220> FEATURE:
<221> NAME/KEY: MOD_RES
<222> LOCATION: (97)
<223> OTHER INFORMATION: Arg or Lys

<400> SEQUENCE: 4

Cys Xaa Xaa His Glu Leu Tyr Val Ser Phe Xaa Asp Leu Gly Trp Xaa
 1               5                  10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Ile Leu Xaa Lys Xaa Arg Asn Met Val Val
                85                  90                  95

Xaa Ala Cys Gly Cys His
            100

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (2)
<223> OTHER INFORMATION: Tyr or Lys
```

```
<220> FEATURE:
<221> NAME/KEY: MOD_RES
<222> LOCATION: (3)
<223> OTHER INFORMATION: Val or Ile
<220> FEATURE:
<221> NAME/KEY: MOD_RES
<222> LOCATION: (4)
<223> OTHER INFORMATION: Ser, Asp or Glu
<220> FEATURE:
<221> NAME/KEY: MOD_RES
<222> LOCATION: (6)
<223> OTHER INFORMATION: Arg, Gln, Ser, Lys or Ala
<220> FEATURE:
<221> NAME/KEY: MOD_RES
<222> LOCATION: (7)
<223> OTHER INFORMATION: Asp or Glu
<220> FEATURE:
<221> NAME/KEY: MOD_RES
<222> LOCATION: (8)
<223> OTHER INFORMATION: Leu, Val or Ile
<220> FEATURE:
<221> NAME/KEY: MOD_RES
<222> LOCATION: (11)
<223> OTHER INFORMATION: Gln, Leu, Asp, His, Asn or Ser
<220> FEATURE:
<221> NAME/KEY: MOD_RES
<222> LOCATION: (12)
<223> OTHER INFORMATION: Asp, Arg, Asn or Glu
<220> FEATURE:
<221> NAME/KEY: MOD_RES
<222> LOCATION: (13)
<223> OTHER INFORMATION: Trp or Ser
<220> FEATURE:
<221> NAME/KEY: MOD_RES
<222> LOCATION: (14)
<223> OTHER INFORMATION: Ile or Val
<220> FEATURE:
<221> NAME/KEY: MOD_RES
<222> LOCATION: (15)
<223> OTHER INFORMATION: Ile or Val
<220> FEATURE:
<221> NAME/KEY: MOD_RES
<222> LOCATION: (16)
<223> OTHER INFORMATION: Ala or Ser
<220> FEATURE:
<221> NAME/KEY: MOD_RES
<222> LOCATION: (18)
<223> OTHER INFORMATION: Glu, Gln, Leu, Lys, Pro or Arg
<220> FEATURE:
<221> NAME/KEY: MOD_RES
<222> LOCATION: (19)
<223> OTHER INFORMATION: Gly or Ser
<220> FEATURE:
<221> NAME/KEY: MOD_RES
<222> LOCATION: (20)
<223> OTHER INFORMATION: Tyr or Phe
<220> FEATURE:
<221> NAME/KEY: MOD_RES
<222> LOCATION: (21)
<223> OTHER INFORMATION: Ala, Ser, Asp, Met, His, Gln, Leu or Gly
<220> FEATURE:
<221> NAME/KEY: MOD_RES
<222> LOCATION: (23)
<223> OTHER INFORMATION: Tyr, Asn or Phe
<220> FEATURE:
<221> NAME/KEY: MOD_RES
<222> LOCATION: (26)
<223> OTHER INFORMATION: Glu, His, Tyr, Asp, Gln, Ala or Ser
<220> FEATURE:
<221> NAME/KEY: MOD_RES
<222> LOCATION: (28)
<223> OTHER INFORMATION: Glu, Lys, Asp, Gln or Ala
<220> FEATURE:
<221> NAME/KEY: MOD_RES
<222> LOCATION: (30)
<223> OTHER INFORMATION: Ala, Ser, Pro, Gln, Ile or Asn
<220> FEATURE:
<221> NAME/KEY: MOD_RES
<222> LOCATION: (31)
<223> OTHER INFORMATION: Phe, Leu or Tyr
```

```
-continued

<220> FEATURE:
<221> NAME/KEY: MOD_RES
<222> LOCATION: (33)
<223> OTHER INFORMATION: Leu, Val or Met
<220> FEATURE:
<221> NAME/KEY: MOD_RES
<222> LOCATION: (34)
<223> OTHER INFORMATION: Asn, Asp, Ala, Thr or Pro
<220> FEATURE:
<221> NAME/KEY: MOD_RES
<222> LOCATION: (35)
<223> OTHER INFORMATION: Ser, Asp, Glu, Leu, Ala or Lys
<220> FEATURE:
<221> NAME/KEY: MOD_RES
<222> LOCATION: (36)
<223> OTHER INFORMATION: Tyr, Cys, His, Ser or Ile
<220> FEATURE:
<221> NAME/KEY: MOD_RES
<222> LOCATION: (37)
<223> OTHER INFORMATION: Met, Phe, Gly or Leu
<220> FEATURE:
<221> NAME/KEY: MOD_RES
<222> LOCATION: (38)
<223> OTHER INFORMATION: Asn, Ser or Lys
<220> FEATURE:
<221> NAME/KEY: MOD_RES
<222> LOCATION: (39)
<223> OTHER INFORMATION: Ala, Ser, Gly or Pro
<220> FEATURE:
<221> NAME/KEY: MOD_RES
<222> LOCATION: (40)
<223> OTHER INFORMATION: Thr, Leu or Ser
<220> FEATURE:
<221> NAME/KEY: MOD_RES
<222> LOCATION: (44)
<223> OTHER INFORMATION: Ile, Val or Thr
<220> FEATURE:
<221> NAME/KEY: MOD_RES
<222> LOCATION: (45)
<223> OTHER INFORMATION: Val, Leu, Met or Ile
<220> FEATURE:
<221> NAME/KEY: MOD_RES
<222> LOCATION: (46)
<223> OTHER INFORMATION: Gln or Arg
<220> FEATURE:
<221> NAME/KEY: MOD_RES
<222> LOCATION: (47)
<223> OTHER INFORMATION: Thr, Ala or Ser
<220> FEATURE:
<221> NAME/KEY: MOD_RES
<222> LOCATION: (48)
<223> OTHER INFORMATION: Leu or Ile
<220> FEATURE:
<221> NAME/KEY: MOD_RES
<222> LOCATION: (49)
<223> OTHER INFORMATION: Val or Met
<220> FEATURE:
<221> NAME/KEY: MOD_RES
<222> LOCATION: (50)
<223> OTHER INFORMATION: His, Asn or Arg
<220> FEATURE:
<221> NAME/KEY: MOD_RES
<222> LOCATION: (51)
<223> OTHER INFORMATION: Phe, Leu, Asn, Ser, Ala or Val
<220> FEATURE:
<221> NAME/KEY: MOD_RES
<222> LOCATION: (52)
<223> OTHER INFORMATION: Ile, Met, Asn, Ala, Val, Gly or Leu
<220> FEATURE:
<221> NAME/KEY: MOD_RES
<222> LOCATION: (53)
<223> OTHER INFORMATION: Asn, Lys, Ala, Glu, Gly or Phe
<220> FEATURE:
<221> NAME/KEY: MOD_RES
<222> LOCATION: (54)
<223> OTHER INFORMATION: Pro, Ser or Val
<220> FEATURE:
<221> NAME/KEY: MOD_RES
<222> LOCATION: (55)
<223> OTHER INFORMATION: Glu, Asp, Asn, Gly, Val, Pro or Lys
```

```
<220> FEATURE:
<221> NAME/KEY: MOD_RES
<222> LOCATION: (56)
<223> OTHER INFORMATION: Thr, Ala, Val, Lys, Asp, Tyr, Ser, Gly, Ile or
      His
<220> FEATURE:
<221> NAME/KEY: MOD_RES
<222> LOCATION: (57)
<223> OTHER INFORMATION: Val, Ala or Ile
<220> FEATURE:
<221> NAME/KEY: MOD_RES
<222> LOCATION: (58)
<223> OTHER INFORMATION: Pro or Asp
<220> FEATURE:
<221> NAME/KEY: MOD_RES
<222> LOCATION: (59)
<223> OTHER INFORMATION: Lys, Leu or Glu
<220> FEATURE:
<221> NAME/KEY: MOD_RES
<222> LOCATION: (60)
<223> OTHER INFORMATION: Pro, Val or Ala
<220> FEATURE:
<221> NAME/KEY: MOD_RES
<222> LOCATION: (63)
<223> OTHER INFORMATION: Ala or Val
<220> FEATURE:
<221> NAME/KEY: MOD_RES
<222> LOCATION: (65)
<223> OTHER INFORMATION: Thr, Ala or Glu
<220> FEATURE:
<221> NAME/KEY: MOD_RES
<222> LOCATION: (66)
<223> OTHER INFORMATION: Gln, Lys, Arg or Glu
<220> FEATURE:
<221> NAME/KEY: MOD_RES
<222> LOCATION: (67)
<223> OTHER INFORMATION: Leu, Met or Val
<220> FEATURE:
<221> NAME/KEY: MOD_RES
<222> LOCATION: (68)
<223> OTHER INFORMATION: Asn, Ser, Asp or Gly
<220> FEATURE:
<221> NAME/KEY: MOD_RES
<222> LOCATION: (69)
<223> OTHER INFORMATION: Ala, Pro or Ser
<220> FEATURE:
<221> NAME/KEY: MOD_RES
<222> LOCATION: (70)
<223> OTHER INFORMATION: Ile, Thr, Val or Leu
<220> FEATURE:
<221> NAME/KEY: MOD_RES
<222> LOCATION: (71)
<223> OTHER INFORMATION: Ser, Ala or Pro
<220> FEATURE:
<221> NAME/KEY: MOD_RES
<222> LOCATION: (72)
<223> OTHER INFORMATION: Val, Leu, Met or Ile
<220> FEATURE:
<221> NAME/KEY: MOD_RES
<222> LOCATION: (74)
<223> OTHER INFORMATION: Tyr or Phe
<220> FEATURE:
<221> NAME/KEY: MOD_RES
<222> LOCATION: (75)
<223> OTHER INFORMATION: Phe, Tyr, Leu or His
<220> FEATURE:
<221> NAME/KEY: MOD_RES
<222> LOCATION: (76)
<223> OTHER INFORMATION: Asp, Asn or Leu
<220> FEATURE:
<221> NAME/KEY: MOD_RES
<222> LOCATION: (77)
<223> OTHER INFORMATION: Asp, Glu, Asn, Arg or Ser
<220> FEATURE:
<221> NAME/KEY: MOD_RES
<222> LOCATION: (78)
<223> OTHER INFORMATION: Ser, Gln, Asn, Tyr or Asp
<220> FEATURE:
<221> NAME/KEY: MOD_RES
<222> LOCATION: (79)
```

-continued

```
<223> OTHER INFORMATION: Ser, Asn, Asp, Glu or Lys
<220> FEATURE:
<221> NAME/KEY: MOD_RES
<222> LOCATION: (80)
<223> OTHER INFORMATION: Asn, Thr or Lys
<220> FEATURE:
<221> NAME/KEY: MOD_RES
<222> LOCATION: (82)
<223> OTHER INFORMATION: Ile, Val or Asn
<220> FEATURE:
<221> NAME/KEY: MOD_RES
<222> LOCATION: (84)
<223> OTHER INFORMATION: Lys or Arg
<220> FEATURE:
<221> NAME/KEY: MOD_RES
<222> LOCATION: (85)
<223> OTHER INFORMATION: Lys, Asn, Gln, His, Arg or Val
<220> FEATURE:
<221> NAME/KEY: MOD_RES
<222> LOCATION: (86)
<223> OTHER INFORMATION: Tyr, Glu or His
<220> FEATURE:
<221> NAME/KEY: MOD_RES
<222> LOCATION: (87)
<223> OTHER INFORMATION: Arg, Gln, Glu or Pro
<220> FEATURE:
<221> NAME/KEY: MOD_RES
<222> LOCATION: (88)
<223> OTHER INFORMATION: Asn, Glu, Trp or Asp
<220> FEATURE:
<221> NAME/KEY: MOD_RES
<222> LOCATION: (90)
<223> OTHER INFORMATION: Val, Thr, Ala or Ile
<220> FEATURE:
<221> NAME/KEY: MOD_RES
<222> LOCATION: (92)
<223> OTHER INFORMATION: Arg, Lys, Val, Asp, Gln or Glu
<220> FEATURE:
<221> NAME/KEY: MOD_RES
<222> LOCATION: (93)
<223> OTHER INFORMATION: Ala, Gly, Glu or Ser
<220> FEATURE:
<221> NAME/KEY: MOD_RES
<222> LOCATION: (95)
<223> OTHER INFORMATION: Gly or Ala
<220> FEATURE:
<221> NAME/KEY: MOD_RES
<222> LOCATION: (97)
<223> OTHER INFORMATION: His or Arg

<400> SEQUENCE: 5

Leu Xaa Xaa Xaa Phe Xaa Xaa Xaa Gly Trp Xaa Xaa Xaa Xaa Xaa
 1               5                  10                  15

Pro Xaa Xaa Xaa Xaa Ala Xaa Tyr Cys Xaa Gly Xaa Cys Xaa Xaa Pro
             20                  25                  30

Xaa Xaa Xaa Xaa Xaa Xaa Xaa Xaa Asn His Ala Xaa Xaa Xaa Xaa Xaa
         35                  40                  45

Xaa Xaa Xaa Xaa Xaa Xaa Xaa Xaa Xaa Xaa Xaa Cys Cys Xaa Pro
     50                  55                  60

Xaa Xaa Xaa Xaa Xaa Xaa Xaa Xaa Leu Xaa Xaa Xaa Xaa Xaa Xaa
 65                  70                  75                  80

Val Xaa Leu Xaa Xaa Xaa Xaa Xaa Met Xaa Val Xaa Xaa Cys Xaa Cys
                 85                  90                  95

Xaa

<210> SEQ ID NO 6
<211> LENGTH: 102
<212> TYPE: PRT
<213> ORGANISM: Artificial Sequence
<220> FEATURE:
<223> OTHER INFORMATION: Description of Artificial Sequence: Synthetic
      formula sequence
```

```
<220> FEATURE:
<221> NAME/KEY: MOD_RES
<222> LOCATION: (2)
<223> OTHER INFORMATION: Lys, Arg, Ala or Gln
<220> FEATURE:
<221> NAME/KEY: MOD_RES
<222> LOCATION: (3)
<223> OTHER INFORMATION: Lys, Arg or Met
<220> FEATURE:
<221> NAME/KEY: MOD_RES
<222> LOCATION: (4)
<223> OTHER INFORMATION: His, Arg or Gln
<220> FEATURE:
<221> NAME/KEY: MOD_RES
<222> LOCATION: (5)
<223> OTHER INFORMATION: Glu, Ser, His, Gly, Arg, Pro, Thr or Tyr
<220> FEATURE:
<221> NAME/KEY: MOD_RES
<222> LOCATION: (7)
<223> OTHER INFORMATION: Tyr or Lys
<220> FEATURE:
<221> NAME/KEY: MOD_RES
<222> LOCATION: (8)
<223> OTHER INFORMATION: Val or Ile
<220> FEATURE:
<221> NAME/KEY: MOD_RES
<222> LOCATION: (9)
<223> OTHER INFORMATION: Ser, Asp or Glu
<220> FEATURE:
<221> NAME/KEY: MOD_RES
<222> LOCATION: (11)
<223> OTHER INFORMATION: Arg, Gln, Ser, Lys or Ala
<220> FEATURE:
<221> NAME/KEY: MOD_RES
<222> LOCATION: (12)
<223> OTHER INFORMATION: Asp or Glu
<220> FEATURE:
<221> NAME/KEY: MOD_RES
<222> LOCATION: (13)
<223> OTHER INFORMATION: Leu, Val or Ile
<220> FEATURE:
<221> NAME/KEY: MOD_RES
<222> LOCATION: (16)
<223> OTHER INFORMATION: Gln, Leu, Asp, His, Asn or Ser
<220> FEATURE:
<221> NAME/KEY: MOD_RES
<222> LOCATION: (17)
<223> OTHER INFORMATION: Asp, Arg, Asn or Glu
<220> FEATURE:
<221> NAME/KEY: MOD_RES
<222> LOCATION: (18)
<223> OTHER INFORMATION: Trp or Ser
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (20)
<223> OTHER INFORMATION: Ile or Val
<220> FEATURE:
<221> NAME/KEY: MOD_RES
<222> LOCATION: (21)
<223> OTHER INFORMATION: Ala or Ser
<220> FEATURE:
<221> NAME/KEY: MOD_RES
<222> LOCATION: (23)
<223> OTHER INFORMATION: Glu, Gln, Leu, Lys, Pro or Arg
<220> FEATURE:
<221> NAME/KEY: MOD_RES
<222> LOCATION: (24)
<223> OTHER INFORMATION: Gly or Ser
<220> FEATURE:
<221> NAME/KEY: MOD_RES
<222> LOCATION: (25)
<223> OTHER INFORMATION: Tyr or Phe
<220> FEATURE:
<221> NAME/KEY: MOD_RES
<222> LOCATION: (26)
<223> OTHER INFORMATION: Ala, Ser, Asp, Met, His, Gln, Leu or Gly
```

```
-continued

<220> FEATURE:
<221> NAME/KEY: MOD_RES
<222> LOCATION: (28)
<223> OTHER INFORMATION: Tyr, Asn or Phe
<220> FEATURE:
<221> NAME/KEY: MOD_RES
<222> LOCATION: (31)
<223> OTHER INFORMATION: Glu, His, Tyr, Asp, Gln, Ala or Ser
<220> FEATURE:
<221> NAME/KEY: MOD_RES
<222> LOCATION: (33)
<223> OTHER INFORMATION: Glu, Lys, Asp, Gln or Ala
<220> FEATURE:
<221> NAME/KEY: MOD_RES
<222> LOCATION: (35)
<223> OTHER INFORMATION: Ala, Ser, Pro, Gln, Ile or Asn
<220> FEATURE:
<221> NAME/KEY: MOD_RES
<222> LOCATION: (36)
<223> OTHER INFORMATION: Phe, Leu or Tyr
<220> FEATURE:
<221> NAME/KEY: MOD_RES
<222> LOCATION: (38)
<223> OTHER INFORMATION: Leu, Val or Met
<220> FEATURE:
<221> NAME/KEY: MOD_RES
<222> LOCATION: (39)
<223> OTHER INFORMATION: Asn, Asp, Ala, Thr or Pro
<220> FEATURE:
<221> NAME/KEY: MOD_RES
<222> LOCATION: (40)
<223> OTHER INFORMATION: Ser, Asp, Glu, Leu, Ala or Lys
<220> FEATURE:
<221> NAME/KEY: MOD_RES
<222> LOCATION: (41)
<223> OTHER INFORMATION: Tyr, Cys, His, Ser or Ile
<220> FEATURE:
<221> NAME/KEY: MOD_RES
<222> LOCATION: (42)
<223> OTHER INFORMATION: Met, Phe, Gly or Leu
<220> FEATURE:
<221> NAME/KEY: MOD_RES
<222> LOCATION: (43)
<223> OTHER INFORMATION: Asn, Ser or Lys
<220> FEATURE:
<221> NAME/KEY: MOD_RES
<222> LOCATION: (44)
<223> OTHER INFORMATION: Ala, Ser, Gly or Pro
<220> FEATURE:
<221> NAME/KEY: MOD_RES
<222> LOCATION: (45)
<223> OTHER INFORMATION: Thr, Leu or Ser
<220> FEATURE:
<221> NAME/KEY: MOD_RES
<222> LOCATION: (49)
<223> OTHER INFORMATION: Ile, Val or Thr
<220> FEATURE:
<221> NAME/KEY: MOD_RES
<222> LOCATION: (50)
<223> OTHER INFORMATION: Val, Leu, Met or Ile
<220> FEATURE:
<221> NAME/KEY: MOD_RES
<222> LOCATION: (51)
<223> OTHER INFORMATION: Gln or Arg
<220> FEATURE:
<221> NAME/KEY: MOD_RES
<222> LOCATION: (52)
<223> OTHER INFORMATION: Thr, Ala or Ser
<220> FEATURE:
<221> NAME/KEY: MOD_RES
<222> LOCATION: (53)
<223> OTHER INFORMATION: Leu or Ile
<220> FEATURE:
<221> NAME/KEY: MOD_RES
<222> LOCATION: (54)
<223> OTHER INFORMATION: Val or Met
<220> FEATURE:
<221> NAME/KEY: MOD_RES
<222> LOCATION: (55)
<223> OTHER INFORMATION: His, Asn or Arg
```

```
-continued

<220> FEATURE:
<221> NAME/KEY: MOD_RES
<222> LOCATION: (56)
<223> OTHER INFORMATION: Phe, Leu, Asn, Ser, Ala or Val
<220> FEATURE:
<221> NAME/KEY: MOD_RES
<222> LOCATION: (57)
<223> OTHER INFORMATION: Ile, Met, Asn, Ala, Val, Gly or Leu
<220> FEATURE:
<221> NAME/KEY: MOD_RES
<222> LOCATION: (58)
<223> OTHER INFORMATION: Asn, Lys, Ala, Glu, Gly or Phe
<220> FEATURE:
<221> NAME/KEY: MOD_RES
<222> LOCATION: (59)
<223> OTHER INFORMATION: Pro, Ser or Val
<220> FEATURE:
<221> NAME/KEY: MOD_RES
<222> LOCATION: (60)
<223> OTHER INFORMATION: Glu, Asp, Asn, Gly, Val, Pro or Lys
<220> FEATURE:
<221> NAME/KEY: MOD_RES
<222> LOCATION: (61)
<223> OTHER INFORMATION: Thr, Ala, Val, Lys, Asp, Tyr, Ser, Gly, Ile or
      His
<220> FEATURE:
<221> NAME/KEY: MOD_RES
<222> LOCATION: (62)
<223> OTHER INFORMATION: Val, Ala or Ile
<220> FEATURE:
<221> NAME/KEY: MOD_RES
<222> LOCATION: (63)
<223> OTHER INFORMATION: Pro or Asp
<220> FEATURE:
<221> NAME/KEY: MOD_RES
<222> LOCATION: (64)
<223> OTHER INFORMATION: Lys, Leu or Glu
<220> FEATURE:
<221> NAME/KEY: MOD_RES
<222> LOCATION: (65)
<223> OTHER INFORMATION: Pro, Val or Ala
<220> FEATURE:
<221> NAME/KEY: MOD_RES
<222> LOCATION: (68)
<223> OTHER INFORMATION: Ala or Val
<220> FEATURE:
<221> NAME/KEY: MOD_RES
<222> LOCATION: (70)
<223> OTHER INFORMATION: Thr, Ala or Glu
<220> FEATURE:
<221> NAME/KEY: MOD_RES
<222> LOCATION: (71)
<223> OTHER INFORMATION: Gln, Lys, Arg or Glu
<220> FEATURE:
<221> NAME/KEY: MOD_RES
<222> LOCATION: (72)
<223> OTHER INFORMATION: Leu, Met or Val
<220> FEATURE:
<221> NAME/KEY: MOD_RES
<222> LOCATION: (73)
<223> OTHER INFORMATION: Asn, Ser, Asp or Gly
<220> FEATURE:
<221> NAME/KEY: MOD_RES
<222> LOCATION: (74)
<223> OTHER INFORMATION: Ala, Pro or Ser
<220> FEATURE:
<221> NAME/KEY: MOD_RES
<222> LOCATION: (75)
<223> OTHER INFORMATION: Ile, Thr, Val or Leu
<220> FEATURE:
<221> NAME/KEY: MOD_RES
<222> LOCATION: (76)
<223> OTHER INFORMATION: Ser, Ala or Pro
<220> FEATURE:
<221> NAME/KEY: MOD_RES
<222> LOCATION: (77)
<223> OTHER INFORMATION: Val, Leu, Met or Ile
<220> FEATURE:
<221> NAME/KEY: MOD_RES
<222> LOCATION: (79)
```

```
<223> OTHER INFORMATION: Tyr or Phe
<220> FEATURE:
<221> NAME/KEY: MOD_RES
<222> LOCATION: (80)
<223> OTHER INFORMATION: Phe, Tyr, Leu or His
<220> FEATURE:
<221> NAME/KEY: MOD_RES
<222> LOCATION: (81)
<223> OTHER INFORMATION: Asp, Asn or Leu
<220> FEATURE:
<221> NAME/KEY: MOD_RES
<222> LOCATION: (82)
<223> OTHER INFORMATION: Asp, Glu, Asn, Arg or Ser
<220> FEATURE:
<221> NAME/KEY: MOD_RES
<222> LOCATION: (83)
<223> OTHER INFORMATION: Ser, Gln, Asn, Tyr or Asp
<220> FEATURE:
<221> NAME/KEY: MOD_RES
<222> LOCATION: (84)
<223> OTHER INFORMATION: Ser, Asn, Asp, Glu or Lys
<220> FEATURE:
<221> NAME/KEY: MOD_RES
<222> LOCATION: (85)
<223> OTHER INFORMATION: Asn, Thr or Lys
<220> FEATURE:
<221> NAME/KEY: MOD_RES
<222> LOCATION: (87)
<223> OTHER INFORMATION: Ile, Val or Asn
<220> FEATURE:
<221> NAME/KEY: MOD_RES
<222> LOCATION: (89)
<223> OTHER INFORMATION: Lys or Arg
<220> FEATURE:
<221> NAME/KEY: MOD_RES
<222> LOCATION: (90)
<223> OTHER INFORMATION: Lys, Asn, Gln, His, Arg or Val
<220> FEATURE:
<221> NAME/KEY: MOD_RES
<222> LOCATION: (91)
<223> OTHER INFORMATION: Tyr, Glu or His
<220> FEATURE:
<221> NAME/KEY: MOD_RES
<222> LOCATION: (92)
<223> OTHER INFORMATION: Arg, Gln, Glu or Pro
<220> FEATURE:
<221> NAME/KEY: MOD_RES
<222> LOCATION: (93)
<223> OTHER INFORMATION: Asn, Glu, Trp or Asp
<220> FEATURE:
<221> NAME/KEY: MOD_RES
<222> LOCATION: (95)
<223> OTHER INFORMATION: Val, Thr, Ala or Ile
<220> FEATURE:
<221> NAME/KEY: MOD_RES
<222> LOCATION: (97)
<223> OTHER INFORMATION: Arg, Lys, Val, Asp, Gln or Glu
<220> FEATURE:
<221> NAME/KEY: MOD_RES
<222> LOCATION: (98)
<223> OTHER INFORMATION: Ala, Gly, Glu or Ser
<220> FEATURE:
<221> NAME/KEY: MOD_RES
<222> LOCATION: (100)
<223> OTHER INFORMATION: Gly or Ala
<220> FEATURE:
<221> NAME/KEY: MOD_RES
<222> LOCATION: (102)
<223> OTHER INFORMATION: His or Arg

<400> SEQUENCE: 6

Cys Xaa Xaa Xaa Xaa Leu Xaa Xaa Xaa Phe Xaa Xaa Xaa Gly Trp Xaa
 1               5                  10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45
```

```
Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Xaa Xaa Xaa Met Xaa Val
                 85                  90                  95

Xaa Xaa Cys Xaa Cys Xaa
            100

<210> SEQ ID NO 7
<211> LENGTH: 97
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (1)
<223> OTHER INFORMATION: Phe, Leu or Glu
<220> FEATURE:
<221> NAME/KEY: MOD_RES
<222> LOCATION: (2)
<223> OTHER INFORMATION: Tyr, Phe, His, Arg, Thr, Lys, Gln, Val or Glu
<220> FEATURE:
<221> NAME/KEY: MOD_RES
<222> LOCATION: (3)
<223> OTHER INFORMATION: Val, Ile, Leu or Asp
<220> FEATURE:
<221> NAME/KEY: MOD_RES
<222> LOCATION: (4)
<223> OTHER INFORMATION: Ser, Asp, Glu, Asn or Phe
<220> FEATURE:
<221> NAME/KEY: MOD_RES
<222> LOCATION: (5)
<223> OTHER INFORMATION: Phe or Glu
<220> FEATURE:
<221> NAME/KEY: MOD_RES
<222> LOCATION: (6)
<223> OTHER INFORMATION: Arg, Gln, Lys, Ser, Glu, Ala or Asn
<220> FEATURE:
<221> NAME/KEY: MOD_RES
<222> LOCATION: (7)
<223> OTHER INFORMATION: Asp, Glu, Leu, Ala or Gln
<220> FEATURE:
<221> NAME/KEY: MOD_RES
<222> LOCATION: (8)
<223> OTHER INFORMATION: Leu, Val, Met, Ile or Phe
<220> FEATURE:
<221> NAME/KEY: MOD_RES
<222> LOCATION: (9)
<223> OTHER INFORMATION: Gly, His or Lys
<220> FEATURE:
<221> NAME/KEY: MOD_RES
<222> LOCATION: (10)
<223> OTHER INFORMATION: Trp or Met
<220> FEATURE:
<221> NAME/KEY: MOD_RES
<222> LOCATION: (11)
<223> OTHER INFORMATION: Gln, Leu, His, Glu, Asn, Asp, Ser or Gly
<220> FEATURE:
<221> NAME/KEY: MOD_RES
<222> LOCATION: (12)
<223> OTHER INFORMATION: Asp, Asn, Ser, Lys, Arg, Glu or His
<220> FEATURE:
<221> NAME/KEY: MOD_RES
<222> LOCATION: (13)
<223> OTHER INFORMATION: Trp or Ser
<220> FEATURE:
<221> NAME/KEY: MOD_RES
<222> LOCATION: (14)
<223> OTHER INFORMATION: Ile or Val
<220> FEATURE:
<221> NAME/KEY: MOD_RES
<222> LOCATION: (15)
```

```
<223> OTHER INFORMATION: Ile or Val
<220> FEATURE:
<221> NAME/KEY: MOD_RES
<222> LOCATION: (16)
<223> OTHER INFORMATION: Ala, Ser, Tyr or Trp
<220> FEATURE:
<221> NAME/KEY: MOD_RES
<222> LOCATION: (18)
<223> OTHER INFORMATION: Glu, Lys, Gln, Met, Pro, Leu, Arg, His or Lys
<220> FEATURE:
<221> NAME/KEY: MOD_RES
<222> LOCATION: (19)
<223> OTHER INFORMATION: Gly, Glu, Asp, Lys, Ser, Gln, Arg or Phe
<220> FEATURE:
<221> NAME/KEY: MOD_RES
<222> LOCATION: (20)
<223> OTHER INFORMATION: Tyr or Phe
<220> FEATURE:
<221> NAME/KEY: MOD_RES
<222> LOCATION: (21)
<223> OTHER INFORMATION: Ala, Ser, Gly, Met, Gln, His, Glu, Asp, Leu,
      Asn, Lys or Thr
<220> FEATURE:
<221> NAME/KEY: MOD_RES
<222> LOCATION: (22)
<223> OTHER INFORMATION: Ala or Pro
<220> FEATURE:
<221> NAME/KEY: MOD_RES
<222> LOCATION: (23)
<223> OTHER INFORMATION: Tyr, Phe, Asn, Ala or Arg
<220> FEATURE:
<221> NAME/KEY: MOD_RES
<222> LOCATION: (24)
<223> OTHER INFORMATION: Tyr, His, Glu, Phe or Arg
<220> FEATURE:
<221> NAME/KEY: MOD_RES
<222> LOCATION: (26)
<223> OTHER INFORMATION: Glu, Asp, Ala, Ser, Tyr, His, Lys, Arg, Gln or
      Gly
<220> FEATURE:
<221> NAME/KEY: MOD_RES
<222> LOCATION: (28)
<223> OTHER INFORMATION: Glu, Asp, Leu, Val, Lys, Gly, Thr, Ala or Gln
<220> FEATURE:
<221> NAME/KEY: MOD_RES
<222> LOCATION: (30)
<223> OTHER INFORMATION: Ala, Ser, Ile, Asn, Pro, Glu, Asp, Phe, Gln or
      Leu
<220> FEATURE:
<221> NAME/KEY: MOD_RES
<222> LOCATION: (31)
<223> OTHER INFORMATION: Phe, Tyr, Leu, Asn, Gly or Arg
<220> FEATURE:
<221> NAME/KEY: MOD_RES
<222> LOCATION: (32)
<223> OTHER INFORMATION: Pro, Ser, Ala or Val
<220> FEATURE:
<221> NAME/KEY: MOD_RES
<222> LOCATION: (33)
<223> OTHER INFORMATION: Leu, Met, Glu, Phe or Val
<220> FEATURE:
<221> NAME/KEY: MOD_RES
<222> LOCATION: (34)
<223> OTHER INFORMATION: Asn, Asp, Thr, Gly, Ala, Arg, Leu or Pro
<220> FEATURE:
<221> NAME/KEY: MOD_RES
<222> LOCATION: (35)
<223> OTHER INFORMATION: Ser, Ala, Glu, Asp, Thr, Leu, Lys, Gln or His
<220> FEATURE:
<221> NAME/KEY: MOD_RES
<222> LOCATION: (36)
<223> OTHER INFORMATION: Tyr, His, Cys, Ile, Arg, Asp, Asn, Lys, Ser,
      Glu or Gly
<220> FEATURE:
<221> NAME/KEY: MOD_RES
<222> LOCATION: (37)
<223> OTHER INFORMATION: Met, Leu, Phe, Val, Gly or Tyr
<220> FEATURE:
<221> NAME/KEY: MOD_RES
<222> LOCATION: (38)
```

-continued

```
<223> OTHER INFORMATION: Asn, Glu, Thr, Pro, Lys, His, Gly, Met, Val or
      Arg
<220> FEATURE:
<221> NAME/KEY: MOD_RES
<222> LOCATION: (39)
<223> OTHER INFORMATION: Ala, Ser, Gly, Pro or Phe
<220> FEATURE:
<221> NAME/KEY: MOD_RES
<222> LOCATION: (40)
<223> OTHER INFORMATION: Thr, Ser, Leu, Pro, His or Met
<220> FEATURE:
<221> NAME/KEY: MOD_RES
<222> LOCATION: (41)
<223> OTHER INFORMATION: Asn, Lys, Val, Thr or Gln
<220> FEATURE:
<221> NAME/KEY: MOD_RES
<222> LOCATION: (42)
<223> OTHER INFORMATION: His, Tyr or Lys
<220> FEATURE:
<221> NAME/KEY: MOD_RES
<222> LOCATION: (43)
<223> OTHER INFORMATION: Ala, Thr, Leu or Tyr
<220> FEATURE:
<221> NAME/KEY: MOD_RES
<222> LOCATION: (44)
<223> OTHER INFORMATION: Ile, Thr, Val, Phe, Tyr, Met or Pro
<220> FEATURE:
<221> NAME/KEY: MOD_RES
<222> LOCATION: (45)
<223> OTHER INFORMATION: Val, Leu, Met, Ile or His
<220> FEATURE:
<221> NAME/KEY: MOD_RES
<222> LOCATION: (46)
<223> OTHER INFORMATION: Gln, Arg or Thr
<220> FEATURE:
<221> NAME/KEY: MOD_RES
<222> LOCATION: (47)
<223> OTHER INFORMATION: Thr, Ser, Ala, Asn or His
<220> FEATURE:
<221> NAME/KEY: MOD_RES
<222> LOCATION: (48)
<223> OTHER INFORMATION: Leu, Asn or Ile
<220> FEATURE:
<221> NAME/KEY: MOD_RES
<222> LOCATION: (49)
<223> OTHER INFORMATION: Val, Met, Leu, Pro or Ile
<220> FEATURE:
<221> NAME/KEY: MOD_RES
<222> LOCATION: (50)
<223> OTHER INFORMATION: His, Asn, Arg, Lys, Tyr or Gln
<220> FEATURE:
<221> NAME/KEY: MOD_RES
<222> LOCATION: (51)
<223> OTHER INFORMATION: Phe, Leu, Ser, Asn, Met, Ala, Arg, Glu, Gly or
      Gln
<220> FEATURE:
<221> NAME/KEY: MOD_RES
<222> LOCATION: (52)
<223> OTHER INFORMATION: Ile, Met, Leu, Val, Lys, Gln, Ala or Tyr
<220> FEATURE:
<221> NAME/KEY: MOD_RES
<222> LOCATION: (53)
<223> OTHER INFORMATION: Asn, Phe, Lys, Glu, Asp, Ala, Gln, Gly, Leu or
      Val
<220> FEATURE:
<221> NAME/KEY: MOD_RES
<222> LOCATION: (54)
<223> OTHER INFORMATION: Pro, Asn, Ser, Val or Asp
<220> FEATURE:
<221> NAME/KEY: MOD_RES
<222> LOCATION: (55)
<223> OTHER INFORMATION: Glu, Asp, Asn, Lys, Arg, Ser, Gly, Thr, Gln,
      Pro or His
<220> FEATURE:
<221> NAME/KEY: MOD_RES
<222> LOCATION: (56)
<223> OTHER INFORMATION: Thr, His, Tyr, Ala, Ile, Lys, Asp, Ser, Gly or
      Arg
<220> FEATURE:
<221> NAME/KEY: MOD_RES
```

```
<222> LOCATION: (57)
<223> OTHER INFORMATION: Val, Ile, Thr, Ala, Leu or Ser
<220> FEATURE:
<221> NAME/KEY: MOD_RES
<222> LOCATION: (58)
<223> OTHER INFORMATION: Pro, Gly, Ser, Asp or Ala
<220> FEATURE:
<221> NAME/KEY: MOD_RES
<222> LOCATION: (59)
<223> OTHER INFORMATION: Lys, Leu, Pro, Ala, Ser, Glu, Arg or Gly
<220> FEATURE:
<221> NAME/KEY: MOD_RES
<222> LOCATION: (60)
<223> OTHER INFORMATION: Pro, Ala, Val, Thr or Ser
<220> FEATURE:
<221> NAME/KEY: MOD_RES
<222> LOCATION: (61)
<223> OTHER INFORMATION: Cys, Val or Ser
<220> FEATURE:
<221> NAME/KEY: MOD_RES
<222> LOCATION: (63)
<223> OTHER INFORMATION: Ala, Val or Thr
<220> FEATURE:
<221> NAME/KEY: MOD_RES
<222> LOCATION: (65)
<223> OTHER INFORMATION: Thr, Ala, Glu, Val, Gly, Asp or Tyr
<220> FEATURE:
<221> NAME/KEY: MOD_RES
<222> LOCATION: (66)
<223> OTHER INFORMATION: Gln, Lys, Glu, Arg or Val
<220> FEATURE:
<221> NAME/KEY: MOD_RES
<222> LOCATION: (67)
<223> OTHER INFORMATION: Leu, Met, Thr or Tyr
<220> FEATURE:
<221> NAME/KEY: MOD_RES
<222> LOCATION: (68)
<223> OTHER INFORMATION: Asn, Ser, Gly, Thr, Asp, Glu, Lys or Val
<220> FEATURE:
<221> NAME/KEY: MOD_RES
<222> LOCATION: (69)
<223> OTHER INFORMATION: Ala, Pro, Gly or Ser
<220> FEATURE:
<221> NAME/KEY: MOD_RES
<222> LOCATION: (70)
<223> OTHER INFORMATION: Ile, Thr, Leu or Val
<220> FEATURE:
<221> NAME/KEY: MOD_RES
<222> LOCATION: (71)
<223> OTHER INFORMATION: Ser, Pro, Ala, Thr, Asn or Gly
<220> FEATURE:
<221> NAME/KEY: MOD_RES
<222> LOCATION: (72)
<223> OTHER INFORMATION: Val, Ile, Leu or Met
<220> FEATURE:
<221> NAME/KEY: MOD_RES
<222> LOCATION: (74)
<223> OTHER INFORMATION: Tyr, Phe, Arg, Thr, Tyr or Met
<220> FEATURE:
<221> NAME/KEY: MOD_RES
<222> LOCATION: (75)
<223> OTHER INFORMATION: Phe, Tyr, His, Leu, Ile, Lys, Gln or Val
<220> FEATURE:
<221> NAME/KEY: MOD_RES
<222> LOCATION: (76)
<223> OTHER INFORMATION: Asp, Leu, Asn or Glu
<220> FEATURE:
<221> NAME/KEY: MOD_RES
<222> LOCATION: (77)
<223> OTHER INFORMATION: Asp, Ser, Arg, Asn, Glu, Ala, Lys, Gly or Pro
<220> FEATURE:
<221> NAME/KEY: MOD_RES
<222> LOCATION: (78)
<223> OTHER INFORMATION: Ser, Asn, Asp, Tyr, Ala, Gly, Gln, Met, Glu,
      Asn or Lys
<220> FEATURE:
<221> NAME/KEY: MOD_RES
<222> LOCATION: (79)
<223> OTHER INFORMATION: Ser, Asn, Glu, Asp, Val, Lys, Gly, Gln, or Arg
<220> FEATURE:
```

-continued

```
<221> NAME/KEY: MOD_RES
<222> LOCATION: (80)
<223> OTHER INFORMATION: Asn, Lys, Thr, Pro, Val, Ile, Arg, Ser or Gln
<220> FEATURE:
<221> NAME/KEY: MOD_RES
<222> LOCATION: (81)
<223> OTHER INFORMATION: Val, Ile, Thr or Ala
<220> FEATURE:
<221> NAME/KEY: MOD_RES
<222> LOCATION: (82)
<223> OTHER INFORMATION: Ile, Asn, Val, Leu, Tyr, Asp or Ala
<220> FEATURE:
<221> NAME/KEY: MOD_RES
<222> LOCATION: (83)
<223> OTHER INFORMATION: Leu, Tyr, Lys or Ile
<220> FEATURE:
<221> NAME/KEY: MOD_RES
<222> LOCATION: (84)
<223> OTHER INFORMATION: Lys, Arg, Asn, Tyr, Phe, Thr, Glu or Gly
<220> FEATURE:
<221> NAME/KEY: MOD_RES
<222> LOCATION: (85)
<223> OTHER INFORMATION: Lys, Arg, His, Gln, Asn, Glu or Val
<220> FEATURE:
<221> NAME/KEY: MOD_RES
<222> LOCATION: (86)
<223> OTHER INFORMATION: Tyr, His, Glu or Ile
<220> FEATURE:
<221> NAME/KEY: MOD_RES
<222> LOCATION: (87)
<223> OTHER INFORMATION: Arg, Glu, Gln, Pro or Lys
<220> FEATURE:
<221> NAME/KEY: MOD_RES
<222> LOCATION: (88)
<223> OTHER INFORMATION: Asn, Asp, Ala, Glu, Gly or Lys
<220> FEATURE:
<221> NAME/KEY: MOD_RES
<222> LOCATION: (89)
<223> OTHER INFORMATION: Met or Ala
<220> FEATURE:
<221> NAME/KEY: MOD_RES
<222> LOCATION: (90)
<223> OTHER INFORMATION: Val, Ile, Ala, Thr, Ser or Lys
<220> FEATURE:
<221> NAME/KEY: MOD_RES
<222> LOCATION: (91)
<223> OTHER INFORMATION: Val or Ala
<220> FEATURE:
<221> NAME/KEY: MOD_RES
<222> LOCATION: (92)
<223> OTHER INFORMATION: Arg, Lys, Gln, Asp, Glu, Val, Ala, Ser or Thr
<220> FEATURE:
<221> NAME/KEY: MOD_RES
<222> LOCATION: (93)
<223> OTHER INFORMATION: Ala, Ser, Glu, Gly, Arg or Thr
<220> FEATURE:
<221> NAME/KEY: MOD_RES
<222> LOCATION: (95)
<223> OTHER INFORMATION: Gly, Ala or Thr
<220> FEATURE:
<221> NAME/KEY: MOD_RES
<222> LOCATION: (97)
<223> OTHER INFORMATION: His, Arg, Gly, Leu or Ser

<400> SEQUENCE: 7

Xaa Xaa Xaa Xaa Xaa Xaa Xaa Xaa Xaa Xaa Xaa Xaa Xaa Xaa Xaa Xaa
 1               5                   10                  15

Pro Xaa Xaa Xaa Xaa Xaa Xaa Xaa Cys Xaa Gly Xaa Cys Xaa Xaa Xaa
                20                  25                  30

Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Cys Xaa Pro
     50                  55                  60

Xaa Xaa Xaa Xaa Xaa Xaa Xaa Xaa Leu Xaa Xaa Xaa Xaa Xaa Xaa Xaa
 65                  70                  75                  80
```

```
Xaa Xaa Xaa Xaa Xaa Xaa Xaa Xaa Xaa Xaa Xaa Xaa Xaa Cys Xaa Cys
            85                  90                  95

Xaa

<210> SEQ ID NO 8
<211> LENGTH: 102
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (2)
<223> OTHER INFORMATION: Lys, Arg, Gln, Ser, His, Glu, Ala or Cys
<220> FEATURE:
<221> NAME/KEY: MOD_RES
<222> LOCATION: (3)
<223> OTHER INFORMATION: Lys, Arg, Met, Lys, Thr, Leu, Tyr or Ala
<220> FEATURE:
<221> NAME/KEY: MOD_RES
<222> LOCATION: (4)
<223> OTHER INFORMATION: His, Gln, Arg, Lys, Thr, Leu, Val, Pro or Tyr
<220> FEATURE:
<221> NAME/KEY: MOD_RES
<222> LOCATION: (5)
<223> OTHER INFORMATION: Gln, Thr, His, Arg, Pro, Ser, Ala, Gln, Asn,
      Tyr, Lys, Asp or Leu
<220> FEATURE:
<221> NAME/KEY: MOD_RES
<222> LOCATION: (6)
<223> OTHER INFORMATION: Phe, Leu or Glu
<220> FEATURE:
<221> NAME/KEY: MOD_RES
<222> LOCATION: (7)
<223> OTHER INFORMATION: Tyr, Phe, His, Arg, Thr, Lys, Gln, Val or Glu
<220> FEATURE:
<221> NAME/KEY: MOD_RES
<222> LOCATION: (8)
<223> OTHER INFORMATION: Val, Ile, Leu or Asp
<220> FEATURE:
<221> NAME/KEY: MOD_RES
<222> LOCATION: (9)
<223> OTHER INFORMATION: Ser, Asp, Glu, Asn or Phe
<220> FEATURE:
<221> NAME/KEY: MOD_RES
<222> LOCATION: (10)
<223> OTHER INFORMATION: Phe or Glu
<220> FEATURE:
<221> NAME/KEY: MOD_RES
<222> LOCATION: (11)
<223> OTHER INFORMATION: Arg, Gln, Lys, Ser, Glu, Ala or Asn
<220> FEATURE:
<221> NAME/KEY: MOD_RES
<222> LOCATION: (12)
<223> OTHER INFORMATION: Asp, Glu, Leu, Ala or Gln
<220> FEATURE:
<221> NAME/KEY: MOD_RES
<222> LOCATION: (13)
<223> OTHER INFORMATION: Leu, Val, Met, Ile or Phe
<220> FEATURE:
<221> NAME/KEY: MOD_RES
<222> LOCATION: (14)
<223> OTHER INFORMATION: Gly, His or Lys
<220> FEATURE:
<221> NAME/KEY: MOD_RES
<222> LOCATION: (15)
<223> OTHER INFORMATION: Trp or Met
<220> FEATURE:
<221> NAME/KEY: MOD_RES
<222> LOCATION: (16)
<223> OTHER INFORMATION: Gln, Leu, His, Glu, Asn, Asp, Ser or Gly
<220> FEATURE:
<221> NAME/KEY: MOD_RES
<222> LOCATION: (17)
<223> OTHER INFORMATION: Asp, Asn, Ser, Lys, Arg, Glu or His
<220> FEATURE:
```

-continued

```
<221> NAME/KEY: MOD_RES
<222> LOCATION: (18)
<223> OTHER INFORMATION: Trp or Ser
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (20)
<223> OTHER INFORMATION: Ile or Val
<220> FEATURE:
<221> NAME/KEY: MOD_RES
<222> LOCATION: (21)
<223> OTHER INFORMATION: Ala, Ser, Tyr or Trp
<220> FEATURE:
<221> NAME/KEY: MOD_RES
<222> LOCATION: (23)
<223> OTHER INFORMATION: Glu, Lys, Gln, Met, Pro, Leu, Arg, His or Lys
<220> FEATURE:
<221> NAME/KEY: MOD_RES
<222> LOCATION: (24)
<223> OTHER INFORMATION: Gly, Glu, Asp, Lys, Ser, Gln, Arg or Phe
<220> FEATURE:
<221> NAME/KEY: MOD_RES
<222> LOCATION: (25)
<223> OTHER INFORMATION: Tyr or Phe
<220> FEATURE:
<221> NAME/KEY: MOD_RES
<222> LOCATION: (26)
<223> OTHER INFORMATION: Ala, Ser, Gly, Met, Gln, His, Glu, Asp, Leu,
      Asn, Lys or Thr
<220> FEATURE:
<221> NAME/KEY: MOD_RES
<222> LOCATION: (27)
<223> OTHER INFORMATION: Ala or Pro
<220> FEATURE:
<221> NAME/KEY: MOD_RES
<222> LOCATION: (28)
<223> OTHER INFORMATION: Tyr, Phe, Asn, Ala or Arg
<220> FEATURE:
<221> NAME/KEY: MOD_RES
<222> LOCATION: (29)
<223> OTHER INFORMATION: Tyr, His, Glu, Phe or Arg
<220> FEATURE:
<221> NAME/KEY: MOD_RES
<222> LOCATION: (31)
<223> OTHER INFORMATION: Glu, Asp, Ala, Ser, Tyr, His, Lys, Arg, Gln or
      Gly
<220> FEATURE:
<221> NAME/KEY: MOD_RES
<222> LOCATION: (33)
<223> OTHER INFORMATION: Glu, Asp, Leu, Val, Lys, Gly, Thr, Ala or Gln
<220> FEATURE:
<221> NAME/KEY: MOD_RES
<222> LOCATION: (35)
<223> OTHER INFORMATION: Ala, Ser, Ile, Asn, Pro, Glu, Asp, Phe, Gln or
      Leu
<220> FEATURE:
<221> NAME/KEY: MOD_RES
<222> LOCATION: (36)
<223> OTHER INFORMATION: Phe, Tyr, Leu, Asn, Gly or Arg
<220> FEATURE:
<221> NAME/KEY: MOD_RES
<222> LOCATION: (37)
<223> OTHER INFORMATION: Pro, Ser, Ala or Val
<220> FEATURE:
<221> NAME/KEY: MOD_RES
<222> LOCATION: (38)
<223> OTHER INFORMATION: Leu, Met, Glu, Phe or Val
<220> FEATURE:
<221> NAME/KEY: MOD_RES
<222> LOCATION: (39)
<223> OTHER INFORMATION: Asn, Asp, Thr, Gly, Ala, Arg, Leu or Pro
<220> FEATURE:
<221> NAME/KEY: MOD_RES
<222> LOCATION: (40)
<223> OTHER INFORMATION: Ser, Ala, Glu, Asp, Thr, Leu, Lys, Gln or His
<220> FEATURE:
<221> NAME/KEY: MOD_RES
```

```
<222> LOCATION: (41)
<223> OTHER INFORMATION: Tyr, His, Cys, Ile, Arg, Asp, Asn, Lys, Ser,
      Glu or Gly
<220> FEATURE:
<221> NAME/KEY: MOD_RES
<222> LOCATION: (42)
<223> OTHER INFORMATION: Met, Leu, Phe, Val, Gly or Tyr
<220> FEATURE:
<221> NAME/KEY: MOD_RES
<222> LOCATION: (43)
<223> OTHER INFORMATION: Asn, Glu, Thr, Pro, Lys, His, Gly, Met, Val or
      Arg
<220> FEATURE:
<221> NAME/KEY: MOD_RES
<222> LOCATION: (44)
<223> OTHER INFORMATION: Ala, Ser, Gly, Pro or Phe
<220> FEATURE:
<221> NAME/KEY: MOD_RES
<222> LOCATION: (45)
<223> OTHER INFORMATION: Thr, Ser, Leu, Pro, His or Met
<220> FEATURE:
<221> NAME/KEY: MOD_RES
<222> LOCATION: (46)
<223> OTHER INFORMATION: Asn, Lys, Val, Thr or Gln
<220> FEATURE:
<221> NAME/KEY: MOD_RES
<222> LOCATION: (47)
<223> OTHER INFORMATION: His, Tyr or Lys
<220> FEATURE:
<221> NAME/KEY: MOD_RES
<222> LOCATION: (48)
<223> OTHER INFORMATION: Ala, Thr, Leu or Tyr
<220> FEATURE:
<221> NAME/KEY: MOD_RES
<222> LOCATION: (49)
<223> OTHER INFORMATION: Ile, Thr, Val, Phe, Tyr, Met or Pro
<220> FEATURE:
<221> NAME/KEY: MOD_RES
<222> LOCATION: (50)
<223> OTHER INFORMATION: Val, Leu, Met, Ile or His
<220> FEATURE:
<221> NAME/KEY: MOD_RES
<222> LOCATION: (51)
<223> OTHER INFORMATION: Gln, Arg or Thr
<220> FEATURE:
<221> NAME/KEY: MOD_RES
<222> LOCATION: (52)
<223> OTHER INFORMATION: Thr, Ser, Ala, Asn or His
<220> FEATURE:
<221> NAME/KEY: MOD_RES
<222> LOCATION: (53)
<223> OTHER INFORMATION: Leu, Asn or Ile
<220> FEATURE:
<221> NAME/KEY: MOD_RES
<222> LOCATION: (54)
<223> OTHER INFORMATION: Val, Met, Leu, Pro or Ile
<220> FEATURE:
<221> NAME/KEY: MOD_RES
<222> LOCATION: (55)
<223> OTHER INFORMATION: His, Asn, Arg, Lys, Tyr or Gln
<220> FEATURE:
<221> NAME/KEY: MOD_RES
<222> LOCATION: (56)
<223> OTHER INFORMATION: Phe, Leu, Ser, Asn, Met, Ala, Arg, Glu, Gly or
      Gln
<220> FEATURE:
<221> NAME/KEY: MOD_RES
<222> LOCATION: (57)
<223> OTHER INFORMATION: Ile, Met, Leu, Val, Lys, Gln, Ala or Tyr
<220> FEATURE:
<221> NAME/KEY: MOD_RES
<222> LOCATION: (58)
<223> OTHER INFORMATION: Asn, Phe, Lys, Glu, Asp, Ala, Gln, Gly, Leu or
      Val
<220> FEATURE:
<221> NAME/KEY: MOD_RES
<222> LOCATION: (59)
<223> OTHER INFORMATION: Pro, Asn, Ser, Val or Asp
<220> FEATURE:
<221> NAME/KEY: MOD_RES
```

-continued

```
<222> LOCATION: (60)
<223> OTHER INFORMATION: Glu, Asp, Asn, Lys, Arg, Ser, Gly, Thr, Gln,
      Pro or His
<220> FEATURE:
<221> NAME/KEY: MOD_RES
<222> LOCATION: (61)
<223> OTHER INFORMATION: Thr, His, Tyr, Ala, Ile, Lys, Asp, Ser, Gly or
      Arg
<220> FEATURE:
<221> NAME/KEY: MOD_RES
<222> LOCATION: (62)
<223> OTHER INFORMATION: Val, Ile, Thr, Ala, Leu or Ser
<220> FEATURE:
<221> NAME/KEY: MOD_RES
<222> LOCATION: (63)
<223> OTHER INFORMATION: Pro, Gly, Ser, Asp or Ala
<220> FEATURE:
<221> NAME/KEY: MOD_RES
<222> LOCATION: (64)
<223> OTHER INFORMATION: Lys, Leu, Pro, Ala, Ser, Glu, Arg or Gly
<220> FEATURE:
<221> NAME/KEY: MOD_RES
<222> LOCATION: (65)
<223> OTHER INFORMATION: Pro, Ala, Val, Thr or Ser
<220> FEATURE:
<221> NAME/KEY: MOD_RES
<222> LOCATION: (66)
<223> OTHER INFORMATION: Cys, Val or Ser
<220> FEATURE:
<221> NAME/KEY: MOD_RES
<222> LOCATION: (68)
<223> OTHER INFORMATION: Ala, Val or Thr
<220> FEATURE:
<221> NAME/KEY: MOD_RES
<222> LOCATION: (70)
<223> OTHER INFORMATION: Thr, Ala, Glu, Val, Gly, Asp or Tyr
<220> FEATURE:
<221> NAME/KEY: MOD_RES
<222> LOCATION: (71)
<223> OTHER INFORMATION: Gln, Lys, Glu, Arg or Val
<220> FEATURE:
<221> NAME/KEY: MOD_RES
<222> LOCATION: (72)
<223> OTHER INFORMATION: Leu, Met, Thr or Tyr
<220> FEATURE:
<221> NAME/KEY: MOD_RES
<222> LOCATION: (73)
<223> OTHER INFORMATION: Asn, Ser, Gly, Thr, Asp, Glu, Lys or Val
<220> FEATURE:
<221> NAME/KEY: MOD_RES
<222> LOCATION: (74)
<223> OTHER INFORMATION: Ala, Pro, Gly or Ser
<220> FEATURE:
<221> NAME/KEY: MOD_RES
<222> LOCATION: (75)
<223> OTHER INFORMATION: Ile, Thr, Leu or Val
<220> FEATURE:
<221> NAME/KEY: MOD_RES
<222> LOCATION: (76)
<223> OTHER INFORMATION: Ser, Pro, Ala, Thr, Asn or Gly
<220> FEATURE:
<221> NAME/KEY: MOD_RES
<222> LOCATION: (77)
<223> OTHER INFORMATION: Val, Ile, Leu or Met
<220> FEATURE:
<221> NAME/KEY: MOD_RES
<222> LOCATION: (79)
<223> OTHER INFORMATION: Tyr, Phe, Arg, Thr, Tyr or Met
<220> FEATURE:
<221> NAME/KEY: MOD_RES
<222> LOCATION: (80)
<223> OTHER INFORMATION: Phe, Tyr, His, Leu, Ile, Lys, Gln or Val
<220> FEATURE:
<221> NAME/KEY: MOD_RES
<222> LOCATION: (81)
<223> OTHER INFORMATION: Asp, Leu, Asn or Glu
<220> FEATURE:
<221> NAME/KEY: MOD_RES
<222> LOCATION: (82)
<223> OTHER INFORMATION: Asp, Ser, Arg, Asn, Glu, Ala, Lys, Gly or Pro
```

```
<220> FEATURE:
<221> NAME/KEY: MOD_RES
<222> LOCATION: (83)
<223> OTHER INFORMATION: Ser, Asn, Asp, Tyr, Ala, Gly, Gln, Met, Glu,
      Asn or Lys
<220> FEATURE:
<221> NAME/KEY: MOD_RES
<222> LOCATION: (84)
<223> OTHER INFORMATION: Ser, Asn, Glu, Asp, Val, Lys, Gly, Gln, or Arg
<220> FEATURE:
<221> NAME/KEY: MOD_RES
<222> LOCATION: (85)
<223> OTHER INFORMATION: Asn, Lys, Thr, Pro, Val, Ile, Arg, Ser or Gln
<220> FEATURE:
<221> NAME/KEY: MOD_RES
<222> LOCATION: (86)
<223> OTHER INFORMATION: Val, Ile, Thr or Ala
<220> FEATURE:
<221> NAME/KEY: MOD_RES
<222> LOCATION: (87)
<223> OTHER INFORMATION: Ile, Asn, Val, Leu, Tyr, Asp or Ala
<220> FEATURE:
<221> NAME/KEY: MOD_RES
<222> LOCATION: (88)
<223> OTHER INFORMATION: Leu, Tyr, Lys or Ile
<220> FEATURE:
<221> NAME/KEY: MOD_RES
<222> LOCATION: (89)
<223> OTHER INFORMATION: Lys, Arg, Asn, Tyr, Phe, Thr, Glu or Gly
<220> FEATURE:
<221> NAME/KEY: MOD_RES
<222> LOCATION: (90)
<223> OTHER INFORMATION: Lys, Arg, His, Gln, Asn, Glu or Val
<220> FEATURE:
<221> NAME/KEY: MOD_RES
<222> LOCATION: (91)
<223> OTHER INFORMATION: Tyr, His, Glu or Ile
<220> FEATURE:
<221> NAME/KEY: MOD_RES
<222> LOCATION: (92)
<223> OTHER INFORMATION: Arg, Glu, Gln, Pro or Lys
<220> FEATURE:
<221> NAME/KEY: MOD_RES
<222> LOCATION: (93)
<223> OTHER INFORMATION: Asn, Asp, Ala, Glu, Gly or Lys
<220> FEATURE:
<221> NAME/KEY: MOD_RES
<222> LOCATION: (94)
<223> OTHER INFORMATION: Met or Ala
<220> FEATURE:
<221> NAME/KEY: MOD_RES
<222> LOCATION: (95)
<223> OTHER INFORMATION: Val, Ile, Ala, Thr, Ser or Lys
<220> FEATURE:
<221> NAME/KEY: MOD_RES
<222> LOCATION: (96)
<223> OTHER INFORMATION: Val or Ala
<220> FEATURE:
<221> NAME/KEY: MOD_RES
<222> LOCATION: (97)
<223> OTHER INFORMATION: Arg, Lys, Gln, Asp, Glu, Val, Ala, Ser or Thr
<220> FEATURE:
<221> NAME/KEY: MOD_RES
<222> LOCATION: (98)
<223> OTHER INFORMATION: Ala, Ser, Glu, Gly, Arg or Thr
<220> FEATURE:
<221> NAME/KEY: MOD_RES
<222> LOCATION: (100)
<223> OTHER INFORMATION: Gly, Ala or Thr
<220> FEATURE:
<221> NAME/KEY: MOD_RES
<222> LOCATION: (102)
<223> OTHER INFORMATION: His, Arg, Gly, Leu or Ser

<400> SEQUENCE: 8

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Pro Xaa Xaa Xaa Xaa Xaa Xaa Xaa Cys Xaa Gly
```

```
                    20                  25                  30
Xaa Cys Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Cys Xaa Pro Xaa Xaa Xaa Xaa Xaa Xaa Xaa Leu Xaa Xaa
    65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Cys Xaa Cys Xaa
            100

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      N-term formula peptide fragment
<220> FEATURE:
<221> NAME/KEY: MOD_RES
<222> LOCATION: (2)
<223> OTHER INFORMATION: Lys, Arg, Ala or Gln
<220> FEATURE:
<221> NAME/KEY: MOD_RES
<222> LOCATION: (3)
<223> OTHER INFORMATION: Lys, Arg or Met
<220> FEATURE:
<221> NAME/KEY: MOD_RES
<222> LOCATION: (4)
<223> OTHER INFORMATION: His, Arg or Gln
<220> FEATURE:
<221> NAME/KEY: MOD_RES
<222> LOCATION: (5)
<223> OTHER INFORMATION: Glu, Ser, His, Gly, Arg, Pro, Thr or Tyr

<400> SEQUENCE: 9

Cys Xaa Xaa Xaa Xaa
  1               5

<210> SEQ ID NO 10
<211> LENGTH: 1822
<212> TYPE: DNA
<213> ORGANISM: Homo sapiens
<220> FEATURE:
<221> NAME/KEY: CDS
<222> LOCATION: (49)..(1341)

<400> SEQUENCE: 10
ggtgcgggcc cggagcccgg agcccgggta gcgcgtagag ccggcgcg atg cac gtg      57
                                                   Met His Val
                                                     1 cgc tca ctg cga gct gcg gcg ccg cac agc ttc gtg gcg ctc tgg gca     105
Arg Ser Leu Arg Ala Ala Ala Pro His Ser Phe Val Ala Leu Trp Ala
  5                  10                  15 ccc ctg ttc ctg ctg cgc tcc gcc ctg gcc gac ttc agc ctg gac aac     153
Pro Leu Phe Leu Leu Arg Ser Ala Leu Ala Asp Phe Ser Leu Asp Asn
 20                  25                  30                  35 gag gtg cac tcg agc ttc atc cac cgg cgc ctc cgc agc cag gag cgg     201
Glu Val His Ser Ser Phe Ile His Arg Arg Leu Arg Ser Gln Glu Arg
                 40                  45                  50 cgg gag atg cag cgc gag atc ctc tcc att ttg ggc ttg ccc cac cgc     249
Arg Glu Met Gln Arg Glu Ile Leu Ser Ile Leu Gly Leu Pro His Arg
             55                  60                  65 ccg cgc ccg cac ctc cag ggc aag cac aac tcg gca ccc atg ttc atg     297
Pro Arg Pro His Leu Gln Gly Lys His Asn Ser Ala Pro Met Phe Met
         70                  75                  80
```

```
                    70                  75                  80
ctg gac ctg tac aac gcc atg gcg gtg gag gag ggc ggc ggg ccc ggc     345
Leu Asp Leu Tyr Asn Ala Met Ala Val Glu Glu Gly Gly Gly Pro Gly
             85                  90                  95 ggc cag ggc ttc tcc tac ccc tac aag gcc gtc ttc agt acc cag ggc     393
Gly Gln Gly Phe Ser Tyr Pro Tyr Lys Ala Val Phe Ser Thr Gln Gly
100                 105                 110                 115 ccc cct ctg gcc agc ctg caa gat agc cat ttc ctc acc gac gcc gac     441
Pro Pro Leu Ala Ser Leu Gln Asp Ser His Phe Leu Thr Asp Ala Asp
                    120                 125                 130 atg gtc atg agc ttc gtc aac ctc gtg gaa cat gac aag gaa ttc ttc     489
Met Val Met Ser Phe Val Asn Leu Val Glu His Asp Lys Glu Phe Phe
            135                 140                 145 cac cca cgc tac cac cat cga gag ttc cgg ttt gat ctt tcc aag atc     537
His Pro Arg Tyr His His Arg Glu Phe Arg Phe Asp Leu Ser Lys Ile
        150                 155                 160 cca gaa ggg gaa gct gtc acg gca gcc gaa ttc cgg atc tac aag gac     585
Pro Glu Gly Glu Ala Val Thr Ala Ala Glu Phe Arg Ile Tyr Lys Asp
    165                 170                 175 tac atc cgg gaa cgc ttc gac aat gag acg ttc cgg atc agc gtt tat     633
Tyr Ile Arg Glu Arg Phe Asp Asn Glu Thr Phe Arg Ile Ser Val Tyr
180                 185                 190                 195 cag gtg ctc cag gag cac ttg ggc agg gaa tcg gat ctc ttc ctg ctc     681
Gln Val Leu Gln Glu His Leu Gly Arg Glu Ser Asp Leu Phe Leu Leu
                    200                 205                 210 gac agc cgt acc ctc tgg gcc tcg gag gag ggc tgg ctg gtg ttt gac     729
Asp Ser Arg Thr Leu Trp Ala Ser Glu Glu Gly Trp Leu Val Phe Asp
            215                 220                 225 atc aca gcc acc agc aac cac tgg gtg gtc aat ccg cgg cac aac ctg     777
Ile Thr Ala Thr Ser Asn His Trp Val Val Asn Pro Arg His Asn Leu
        230                 235                 240 ggc ctg cag ctc tcg gtg gag acg ctg gat ggg cag agc atc aac ccc     825
Gly Leu Gln Leu Ser Val Glu Thr Leu Asp Gly Gln Ser Ile Asn Pro
    245                 250                 255 aag ttg gcg ggc ctg att ggg cgg cac ggg ccc cag aac aag cag ccc     873
Lys Leu Ala Gly Leu Ile Gly Arg His Gly Pro Gln Asn Lys Gln Pro
260                 265                 270                 275 ttc atg gtg gct ttc ttc aag gcc acg gag gtc cac ttc cgc agc atc     921
Phe Met Val Ala Phe Phe Lys Ala Thr Glu Val His Phe Arg Ser Ile
                    280                 285                 290 cgg tcc acg ggg agc aaa cag cgc agc cag aac cgc tcc aag acg ccc     969
Arg Ser Thr Gly Ser Lys Gln Arg Ser Gln Asn Arg Ser Lys Thr Pro
            295                 300                 305 aag aac cag gaa gcc ctg cgg atg gcc aac gtg gca gag aac agc agc    1017
Lys Asn Gln Glu Ala Leu Arg Met Ala Asn Val Ala Glu Asn Ser Ser
        310                 315                 320 agc gac cag agg cag gcc tgt aag aag cac gag ctg tat gtc agc ttc    1065
Ser Asp Gln Arg Gln Ala Cys Lys Lys His Glu Leu Tyr Val Ser Phe
    325                 330                 335 cga gac ctg ggc tgg cag gac tgg atc atc gcg cct gaa ggc tac gcc    1113
Arg Asp Leu Gly Trp Gln Asp Trp Ile Ile Ala Pro Glu Gly Tyr Ala
340                 345                 350                 355 gcc tac tac tgt gag ggg gag tgt gcc ttc cct ctg aac tcc tac atg    1161
Ala Tyr Tyr Cys Glu Gly Glu Cys Ala Phe Pro Leu Asn Ser Tyr Met
                    360                 365                 370 aac gcc acc aac cac gcc atc gtg cag acg ctg gtc cac ttc atc aac    1209
Asn Ala Thr Asn His Ala Ile Val Gln Thr Leu Val His Phe Ile Asn
            375                 380                 385 ccg gaa acg gtg ccc aag ccc tgc tgt gcg ccc acg cag ctc aat gcc    1257
Pro Glu Thr Val Pro Lys Pro Cys Cys Ala Pro Thr Gln Leu Asn Ala
```

-continued

```
                            390               395                    400
atc tcc gtc ctc tac ttc gat gac agc tcc aac gtc atc ctg aag aaa    1305
Ile Ser Val Leu Tyr Phe Asp Asp Ser Ser Asn Val Ile Leu Lys Lys
    405                     410                    415 tac aga aac atg gtg gtc cgg gcc tgt ggc tgc cac tagctcctcc         1351
Tyr Arg Asn Met Val Val Arg Ala Cys Gly Cys His
420                 425                 430 gagaattcag acccttggg gccaagtttt tctggatcct ccattgctcg ccttggccag   1411
gaaccagcag accaactgcc ttttgtgaga ccttcccctc cctatcccca actttaaagg  1471
tgtgagagta ttaggaaaca tgagcagcat atggcttttg atcagttttt cagtggcagc  1531
atccaatgaa caagatccta caagctgtgc aggcaaaacc tagcaggaaa aaaaaacaac  1591
gcataaagaa aaatggccgg gccaggtcat tggctgggaa gtctcagcca tgcacggact  1651
cgtttccaga ggtaattatg agcgcctacc agccaggcca cccagccgtg ggaggaaggg  1711
ggcgtggcaa ggggtgggca cattggtgtc tgtgcgaaag gaaaattgac ccggaagttc  1771
ctgtaataaa tgtcacaata aaacgaatga atgaaaaaaa aaaaaaaaa a            1822
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      N-term formula peptide fragment
<220> FEATURE:
<221> NAME/KEY: MOD_RES
<222> LOCATION: (2)
<223> OTHER INFORMATION: Lys, Arg, Gln, Ser, His, Glu, Ala or Cys
<220> FEATURE:
<221> NAME/KEY: MOD_RES
<222> LOCATION: (3)
<223> OTHER INFORMATION: Lys, Arg, Met, Lys, Thr, Leu, Tyr or Ala
<220> FEATURE:
<221> NAME/KEY: MOD_RES
<222> LOCATION: (4)
<223> OTHER INFORMATION: His, Gln, Arg, Lys, Thr, Leu, Val, Pro or Tyr
<220> FEATURE:
<221> NAME/KEY: MOD_RES
<222> LOCATION: (5)
<223> OTHER INFORMATION: Gln, Thr, His, Arg, Pro, Ser, Ala, Gln, Asn,
      Tyr, Lys, Asp or Leu

<400> SEQUENCE: 11

Cys Xaa Xaa Xaa Xaa
1               5